United States Patent
Park et al.

(10) Patent No.: US 11,820,998 B2
(45) Date of Patent: Nov. 21, 2023

(54) PORCINE THY1 GENE PROMOTER SPECIFICALLY EXPRESSED IN NEURONS

(71) Applicant: Jeju National University Industry—Academic Cooperation Foundation, Jeju-si (KR)

(72) Inventors: Se Pill Park, Jeju-si (KR); Young Sok Choi, Seongnam-si (KR); Ok Hee Lee, Seongnam-si (KR); Mi Seon Park, Seoul (KR); Young Ho Kim, Yongin-si (KR); Eun Young Kim, Seoul (KR); Seung Eun Lee, Jeju-si (KR)

(73) Assignee: Jeju National University Industry-Academic Cooperation Foundation, Jeju-si (KR)

( * ) Notice: Subject to any disclaimer, the term of this patent is extended or adjusted under 35 U.S.C. 154(b) by 123 days.

(21) Appl. No.: 17/402,543

(22) Filed: Aug. 15, 2021

(65) Prior Publication Data
US 2021/0371876 A1 Dec. 2, 2021

Related U.S. Application Data

(62) Division of application No. 15/735,185, filed as application No. PCT/KR2017/003750 on Apr. 6, 2017, now Pat. No. 11,118,191.

(30) Foreign Application Priority Data

May 31, 2016 (KR) ........................ 10-2016-0067517

(51) Int. Cl.
*A01K 67/00* (2006.01)
*C12N 15/85* (2006.01)
*C12N 15/86* (2006.01)
*A01K 67/027* (2006.01)

(52) U.S. Cl.
CPC ...... *C12N 15/8509* (2013.01); *A01K 67/0275* (2013.01); *C12N 15/85* (2013.01); *C12N 15/86* (2013.01); *A01K 2227/108* (2013.01); *C12N 2015/8545* (2013.01); *C12N 2740/13043* (2013.01); *C12N 2830/008* (2013.01)

(58) Field of Classification Search
None
See application file for complete search history.

(56) References Cited

U.S. PATENT DOCUMENTS

| | | |
|---|---|---|
| 2001/0016951 A1 | 8/2001 | Sommer et al. |
| 2003/0056231 A1 | 3/2003 | Masliah et al. |
| 2018/0258446 A1 | 9/2018 | Park et al. |

FOREIGN PATENT DOCUMENTS

| | | |
|---|---|---|
| KR | 10-2002-0028904 | 3/2007 |
| KR | 10-2007-0024069 | 1/2008 |
| KR | 10-2010-0003223 | 1/2010 |
| KR | 10-2010-0003224 | 1/2010 |
| KR | 10-2014-0020651 | 2/2014 |
| KR | 10-2015-0145201 | 12/2015 |

OTHER PUBLICATIONS

Advisory Action dated Aug. 13, 2020 from the US Patent and Trademark Office Re. U.S. Appl. No. 15/735,185. (3 pages).
Final Official Action dated May 22, 2020 from the US Patent and Trademark Office Re. U.S. Appl. No. 15/735,185. (17 pages).
International Search Report and the Written Opinion dated Jul. 10, 2017 From the Korean Intellectual Property Office Re. Application No. PCT/KR2017/003750. (9 Pages).
Notice of Allowance dated May 19, 2021 with Interview Summary From the US Patent and Trademark Office Re. U.S. Appl. No. 15/735,185. (7 Pages).
Official Action dated Feb. 3, 2020 From the US Patent and Trademark Office Re. U.S. Appl. No. 15/735,185. (22 pages).
Official Action dated Dec. 9, 2020 from the US Patent and Trademark Office Re. U.S. Appl. No. 15/735,185. (11 pages).
Restriction Official Action dated Nov. 20, 2019 From the US Patent and Trademark Office Re. U.S. Appl. No. 15/735,185. (9 pages).
Translation of International Search Report and the Written Opinion dated Jul. 10, 2017 From the Korean Intellectual Property Office Re. Application No. PCT/KR2017/003750. (8 Pages).
Dolatshad et al. "A Versatile Transgenic Allele for Mouse Overexpression Studies", Mammalian Genome, 26(11-12):598-608, Dec. 1, 2015.
Naito et al. "Expression of Exogenous DNA in the Gonads of Chimaeric Chicken Embryos Produced by Transfer of Primordial Germ Cells Transfected in Vitro and Subsequent Fate of the Introduced DNA", Journal of Reproduction, 113(1): 137-143, May 1, 1998.
Raina et al. "Testis Mediated Gene Transfer: In Vitro Transfection in Goat Testis by Electroporation", Gene 554(1): 96-100, Jan. 1, 2015.

*Primary Examiner* — Marcia S Noble

(57) ABSTRACT

A Thy1 gene promoter specifically expressed in neurons and a recombinant vector including the Thy1 gene promoter are provided. The Thy1 gene promoter may be utilized to regulate an expression of a target gene in preparation of an animal model similar to a human.

2 Claims, 22 Drawing Sheets

Specification includes a Sequence Listing.

FIG. 5

-Preparation of -4858/-2279_Luc Primer

| | | |
|---|---|---|
| F : 5' -(Sac I) GAGCTC TCTAGATGGGGCAACTGGAG - 3' | SEQ ID NO: 15 |
| R : 5' -(Nhe I) GCTAGC GGCCAATCAGAGGCTGAG - 3' | SEQ ID NO: 16 |

-Preparation of -2578/-40_Luc Primer

| | | |
|---|---|---|
| F : 5' -(Kpn1) GGTACC AACCTCCATCCTCCATTCCT - 3' | SEQ ID NO: 17 |
| R : 5' -(Xho1) CTCGAG GGTGGGAATCAGCCAAGAG - 3' | SEQ ID NO: 18 |

-4858/-2279-Luc

-2578/-40-Luc

PC12

NIH3T3

293T

SEQUENCE LISTING

<160> NUMBER OF SEQ ID NOS: 20

<210> SEQ ID NO 1
<211> LENGTH: 500
<212> TYPE: DNA
<213> ORGANISM: Porcine
<220> FEATURE:
<221> NAME/KEY: promoter
<222> LOCATION: (1)..(500)
<223> OTHER INFORMATION: Thy-1 promoter (-3380/-2880) sequences

<400> SEQUENCE: 1

```
gaagccacaa ggatgcaaat caatcaaata aacctttgtt caaaaaaatt tatctcacct      60
gtgagtggga gagacaagtc accccagggc ttctggtgac ttcaaattga tagggagaaa     120
atggttgccc caggggatta aaagcttggt atctgctact cctttagagt tggcctgtct     180
cctccacttt cccacaattc caccatttcc ccctcccact gggctgggat gcagctgtgg     240
agtggctcag ctccaaggac tagggctccc acagcccagg tccggcggcc agccctccca     300
cttccagcct ggaagtggga tggggagtgg gatgagatga acccggcaga ttgtagccac     360
agatgtggat gtgcagggtc cagcacaggg cttgggtgag gagggcggca ccccatccct     420
tgtctgaaga ccaagcagac agtactcagg acttgggagg gggttggggg aggaggagtg     480
catgaaactg agaagaacct                                                 500
```

<210> SEQ ID NO 2
<211> LENGTH: 20
<212> TYPE: DNA
<213> ORGANISM: Artificial Sequence
<220> FEATURE:
<223> OTHER INFORMATION: forward primer for amplifying Thy-1 promoter
      (500bp)

<400> SEQUENCE: 2

```
gaagccacaa ggatgcaaat                                                  20
```

<210> SEQ ID NO 3
<211> LENGTH: 20
<212> TYPE: DNA
<213> ORGANISM: Artificial Sequence
<220> FEATURE:
<223> OTHER INFORMATION: reverse primer for amplifying Thy-1 promoter
      (500bp)

<400> SEQUENCE: 3

```
aggttcttct cagtttcatg                                                  20
```

<210> SEQ ID NO 4
<211> LENGTH: 2579
<212> TYPE: DNA
<213> ORGANISM: Porcine
<220> FEATURE:
<221> NAME/KEY: promoter
<222> LOCATION: (1)..(2579)
<223> OTHER INFORMATION: Thy-1 promoter (-4858/-2279) sequences

<400> SEQUENCE: 4

```
tctagatggg gcaactggag atgatgggag aagaaagcct aagggactaa gaggaaagcc      60
acaatctgtc ggtaaatcct gccttgggta gaatcttcta aacctttccc gctttcagca     120
ctcttatcct gtcccacagg caaagggggag ttttaaatc tcctctccat caccatcttg     180
tgttccgccc tggttcctaa ttgtcttact tgagccattc actccatcca gccgagacct     240
tgttttagca gacacacaac tgcctagagt ctacacgccc ctcccttccc caaactaaag     300
```

```
tgcttaggga cccagaaaat aggccaggtc ctcgtaacct tatcgaaata gcacagctag      360
gccttccacc caacaacact cagagactgg gccatagggt aggaaacagc atccagagtc      420
ttgtccagac agagcccaga catcttctgt agttaagagc cctctgggta ttctcacgtc      480
ctgccccaaa aaaggaacc aagcttatct gggggcggtg gggagaaggg ggtgtaagcc       540
aaagctaaag caactaaagc aactgtgttc tgataggaaa gatccctgga ctgagaacaa      600
gaaagctgtt ccgcaggaaa gaacacactg cgtggagtgt cagggaggag ccagcacct      660 ctggaatgcg gcaggaagat gaatgggaaa gatgaggtgg tggtggaggg cagcagccag     720
ggccttcaaa atcatcctcc agacaatgac aagcccggtc acctgatctg tgaagaggga     780
tggtctgcaa tctccaggcc ctcgagcctg tgcaaagggc aggctcaggc agctctgctg     840
ctagactaag gacatcccag gtgggcacgg agagctgcat ttctcgtaaa gcgccctagg     900
agcttctgtt gttcaccaga accacgagcc cctggactgg accgttcaca aggctcgttc     960
cagttagaaa attccatcac tctaagagct gggaggcacc taacctccaa gggagggaga    1020
gggaagtgga tctcccactt gccagcccag ggatgacttc caacagtgcc attacagtaa    1080
tggaaactgc agtgaaggtg ccagggctga cttctgtgaa gaaagaggag gacaggagtt    1140
cccctagtgg ctcatcagaa atgaatctga ctagcatcca tgaggatgca ggttcaatcc    1200
ctggcctcat tcagtggctt aaggatccag cgttgccgag agctgtgatg taggtcacag    1260
acgcggctca gatcccgtgt tgctgttgct gtggctgtgg cataggtcag aagcgacagc    1320
tctgatttga cccctaacct gggaacctcc atatcccgct agtgcggccc ttaaaagaca    1380 aaagaagga aaagagaaga aaagacatag gcgaacagaa aggcagatga cagggtggca    1440
gggccagcct acacgatggc ccgaccagaa ttcacaaaga agccacaagg atgcaaatca    1500
atcaaataaa cctttgttca aaaaaattta tctcacctgt gagtgggaga gacaagtcac    1560
cccagggctt ctggtgactt caaattgata gggagaaaat ggttgcccca ggggattaaa    1620
agcttggtat ctgctactcc tttagagttg gcctgtctcc tccactttcc cacaattcca    1680
ccatttcccc ctcccactgg gctgggatgc agctgtggag tggctcagct ccaaggacta    1740
ggggctccac agcccaggtc cggcggccag ccctcccact tccagcctgg aagtgggatg    1800
gggagtggga tgagatgaac ccggcagatt gtagccacag atgtggatgt gcagggtcca    1860
gcacagggct tgggtgagga gggcggcacc ccatcccttg tctgaagacc aagcagacag    1920
tactcaggac ttgggagggg gttggggag gaggagtgca tgaaactgag aagaaccttc     1980
tagctgcctg cgccaggagg tacccggag ctgaaggaga tggagtgccc cagagcagaa     2040
agcccctgca ggtctggatg ttctaggctg gatgaggggg cgaggcaggc ctggggacct    2100
gggaagacca ggcgcagtac ctgccttgct tctgaaaatg ctgctccaac gtggaaaaac    2160
actcccacca tctttctttg gagaaagcct gtaatattcc aacaccaaaa cctctcacta    2220
gaggttcccg tggagatggg ttccagatga aagggaagg aggaggcatg ggcgctgcct     2280
aacctccatc ctccattcct tacccctctc ccaccggctt ctgaagccgg ggtcagaaga    2340
aagggttaaa gccttaaaag gggaccgatt ttgcggggct ctgggggtcg gctggcacac    2400
cctgagcggc cccgcccttc tctctagtgt ccagaaccct ccctgccctg cccaggccta    2460
acggccacag ggggagggcc cccctttact gcagaccgcc actctcccac accaatatcg    2520
gaccgcctcc tcctccctct gccacccctt ctcgctcccc actcagcctc tgattggcc     2579
```

<210> SEQ ID NO 5

```
<211> LENGTH: 20
<212> TYPE: DNA
<213> ORGANISM: Artificial Sequence
<220> FEATURE:
<223> OTHER INFORMATION: forward primer for amplifying Thy-1 promoter
      (2579bp)

<400> SEQUENCE: 5
tctagatggg gcaactggag                                                  20

<210> SEQ ID NO 6
<211> LENGTH: 20
<212> TYPE: DNA
<213> ORGANISM: Artificial Sequence
<220> FEATURE:
<223> OTHER INFORMATION: reverse primer for amplifying Thy-1 promoter
      (2579bp)

<400> SEQUENCE: 6
ggccaatcag aggctgagtg                                                  20

<210> SEQ ID NO 7
<211> LENGTH: 2579
<212> TYPE: DNA
<213> ORGANISM: Porcine
<220> FEATURE:
<221> NAME/KEY: promoter
<222> LOCATION: (1)..(2579)
<223> OTHER INFORMATION: Thy-1 promoter (-4858/-2279) sequences (2579
      bp)

<400> SEQUENCE: 7
tctagatggg gcaactggag atgatgggag aagaaagcct aagggactaa gaggaaagcc      60
acaatctgtc ggtaaatcct gccttgggta gaatcttcta aacctttccc gctttcagca    120
ctcttatcct gtcccacagg caaggggag tttttaaatc tcctctccat caccatcttg     180
tgttccgccc tggttcctaa ttgtcttact tgagccattc actccatcca gccgagacct    240
tgttttagca gacacacaac tgcctagagt ctacacgccc ctcccttcc caaactaaag    300 tgcttaggga cccagaaaat aggccaggtc ctcgtaacct tatcgaaata gcacagctag    360
gccttccacc caacaacact cagagactgg gccatagggt aggaaacagc atccagagtc    420
ttgtccagac agagcccaga catcttctgt agttaagagc cctctgggta ttctcacgtc    480
ctgccccaaa aaaggaacc aagcttatct ggggcggtg gggagaaggg ggtgtaagcc     540
aaagctaaag caactaaagc aactgtgttc tgataggaaa gatccctgga ctgagaacaa    600
gaaagctgtt ccgcaggaaa gaacacactg cgtggagtgt cagggaggag gccagcacct    660
ctggaatgcg gcaggaagat gaatgggaaa gatgaggtgg tggtggaggg cagcagccag    720
ggccttcaaa atcatcctcc agacaatgac aagcccggtc acctgatctg tgaagaggga    780
tggtctgcaa tctccaggcc ctcgagcctg tgcaagggc aggctcaggc agctctgctg     840
ctagactaag gacatcccag gtgggcacgg agagctgcat ttctcgtaaa gcgccctagg    900
agcttctgtt gttcaccaga accacgagcc cctggactgg accgttcaca aggctcgttc    960
cagttagaaa attccatcac tctaagagct gggaggcacc taacctccaa gggagggaga   1020
gggaagtgga tctcccactt gccagcccag ggatgacttc caacagtgcc attacagtaa   1080
tggaaactgc agtgaaggtg ccagggctga cttctgtgaa gaaagaggag gacaggagtt   1140
cccctagtgg ctcatcagaa atgaatctga ctagcatcca tgaggatgca ggttcaatcc   1200
ctggcctcat tcagtggctt aaggatccag cgttgccgag agctgtgatg taggtcacag   1260
```

-continued

```
acgcggctca gatcccgtgt tgctgttgct gtggctgtgg cataggtcag aagcgacagc    1320
tctgatttga cccctaacct gggaacctcc atatcccgct agtgcggccc ttaaaagaca    1380
aaagaagga aaagagaaga aaagacatag gcgaacagaa aggcagatga cagggtggca    1440
gggccagcct acacgatggc ccgaccagaa ttcacaaaga agccacaagg atgcaaatca    1500
atcaaataaa cctttgttca aaaaaattta tctcacctgt gagtgggaga gacaagtcac    1560
cccagggctt ctggtgactt caaattgata gggagaaaat ggttgcccca ggggattaaa    1620
agcttggtat ctgctactcc tttagagttg gcctgtctcc tccactttcc cacaattcca    1680
ccatttcccc ctcccactgg gctgggatgc agctgtggag tggctcagct ccaaggacta    1740
ggggctccac agcccaggtc cggcggccag ccctcccact tccagcctgg aagtgggatg    1800
gggagtggga tgagatgaac ccggcagatt gtagccacag atgtggatgt gcagggtcca    1860
gcacagggct tgggtgagga gggcggcacc ccatcccttg tctgaagacc aagcagacag    1920
tactcaggac ttgggagggg gttggggag gaggagtgca tgaaactgag aagaaccttc    1980
tagctgcctg cgccaggagg tacccgggag ctgaaggaga tggagtgccc cagagcagaa    2040
agcccctgca ggtctggatg ttctaggctg gatgagggg cgaggcaggc ctggggacct    2100
gggaagacca ggcgcagtac ctgccttgct tctgaaaatg ctgctccaac gtggaaaaac    2160
actcccacca tctttctttg gagaaagcct gtaatattcc aacaccaaaa cctctcacta    2220
gaggttcccg tggagatggg ttccagatga aagggaagg aggaggcatg ggcgctgcct    2280
aacctccatc ctccattcct taccctctc ccaccggctt ctgaagccgg ggtcagaaga    2340
aagggttaaa gccttaaaag gggaccgatt ttgcggggct ctggggtcg gctggcacac    2400
cctgagcggc cccgcccttc tctctagtgt ccagaaccct ccctgccctg ccaggccta    2460
acggccacag ggggagggcc cccctttact gcagaccgcc actctcccac accaatatcg    2520
gaccgcctcc tcctccctct gccacccctt ctcgctcccc actcagcctc tgattggcc    2579
```

<210> SEQ ID NO 8
<211> LENGTH: 2538
<212> TYPE: DNA
<213> ORGANISM: Porcine
<220> FEATURE:
<221> NAME/KEY: promoter
<222> LOCATION: (1)..(2538)
<223> OTHER INFORMATION: Thy-1 promoter (-2578/-40) sequences (2538 bp)

<400> SEQUENCE: 8

```
aacctccatc ctccattcct taccctctc ccaccggctt ctgaagccgg ggtcagaaga      60
aagggttaaa gccttaaaag gggaccgatt ttgcggggct ctggggtcg gctggcacac     120
cctgagcggc cccgcccttc tctctagtgt ccagaaccct ccctgccctg ccaggccta     180
acggccacag ggggagggcc cccctttact gcagaccgcc actctcccac accaatatcg    240
gaccgcctcc tcctccctct gccacccctt ctcgctcccc actcagcctc tgattggccg    300
agcccccggg tcctccccgc ccctcctctc ccacccttgg tgaaaactgc gggtgccggg    360
cagggtgcag caactggagg cggcggcgtg tccggagcag tctgcggcgg cgagggaccg    420
gaacccaggt gggaactgga gcagggcgg ggcccggagc gccctcggtg cccctgcaag    480
ctctccagac cccaagcttc agaaaaccat ccgagggcgc tcaggaagg agcagtgcag    540
ggcctgggga ggggtctgct tcccaggcag gggcgggagc cggacgccaa ggctgcaggc    600
cgggggccgc aacgcatctt tcgccgcctc ggaggacgtt tgcctgggc gggggcgctg    660
gaggagaact gggaggaagg gcgccaagga cagttttggg ttctgctcgc cacccacaca    720
```

```
tccccaagcc ccgcttgcaa agacagggc ggggggcgac gaaactcggg ggagagaacc      780
gaggacccca aactagaggg aatctctgcc ctccgacctc gcgacaggct gggtgcgggg      840
catccaagga acgggaaacc gcagtgccgc gggcggggac tgggaggaag gcaggcagac      900
gggggaggcg agaactggaa aaggatgaga gaggggaag ggggacttca attgggaatg      960
gaggagattg aatggggag acggaataag ggtggggtta gtcgaacgcg tgctgagagg     1020
gagggaacgc aaagcttctg cgggttctga gctgcgggga cccaggaaac gaaaacagac     1080
tgcgcctccc ctaccagctg tctacccctc cctttggctc tccatcccct gccagcccca     1140
gccccgtttc ttccttttcta ccccttcctc tcctggatcc cgagctcaca ctcctcctct     1200
gtaactcagc gtccgctaat caaaaccaga tgtcagtccc cctttcttcc ccagcagcac     1260
ctccgggtcc ctctcggcag gggtctggga aggagttgac tgcgtccgcg ggcgccgcag     1320
taccccagcc tcgcccctcc ctccccacct ctgggagctg ggctgaacgc ctgggaccct     1380
ggaagccgcg agtcgcgcgc cctgcgcacc cggccgaccc cctcctgtg gcctctccct     1440 ggagaactcc gctgcggaca ggctaggcta cctgctctgt gtctccttgc cagaatattg     1500
attcagccta ggctgcaaaa ataagacagg gcagagaacc taggcaggga ggctatggaa     1560
gccaaactgg aaaactgcaa gcccaagaat tcctcctgga gagctagaga attggaaagg     1620
tcttggttcc aaggcagaga acacatgcac gcatttgcaa taggacagca ctgccgtttt     1680
cctcacaccc ttcgctgtgg gccaagtaca atcctacctg ggccccaca catacctgac     1740 gtcatccctg gccacacagt catctaagag aaaggaaatt aatgtttgtg gatcacttac     1800
ttacagtgcc aaatgtttgt cattttctt aatctccatc acggcccgt gttatgtatc     1860 taaagcccag tttcgttcag tatcttcag gcatctgtta tctgccagaa aggtctggcc     1920
atcggggatt ttcttctgaa tacgaaatag gaagtctttg tttaacaggt agagcgtttt     1980
agttttgcag gatgtcaaga gttctggaaa ttggttgcac cacaatgtaa atgaacttaa     2040
cacttctgaa ctgtacactt aaaaatggtt taggagagga gttccctggt ggcctgggag     2100
ttaagaacta ggcattgtca ctgctgtggc tcaggttga ccctggctgg ggaaattctg     2160
catgccacag gcacagcccc gccaaaaatg gttataataa taaatgttat gttctgcgaa     2220
ttttactaaa aaataggaag tccctatctt cctgaaggga agaggaagtg gtaatttcaa     2280
gacacttact caaagtcacc caactagtaa gcattcagca cagatacccca ccaccaaagg     2340 gtatgttctc catccctctt gctttctctg actgggaaga gccgagtgtc tgtcacattc     2400
actgagaggt gggaggggag agggctacag agaggggctt ggatgccccc catggccatt     2460
atggcatgtc tcccagggc ccccaggcct ggcagtaaat gtgggcacac ctgccccgcc     2520
tcttggctga ttcccacc                                                    2538
```

<210> SEQ ID NO 9
<211> LENGTH: 4242
<212> TYPE: DNA
<213> ORGANISM: Artificial Sequence
<220> FEATURE:
<223> OTHER INFORMATION: Sequence of pGL4.10[luc2] vector (4242 bp)

<400> SEQUENCE: 9

```
ggcctaactg gccggtacct gagctcgcta gcctcgagga tatcaagatc tggcctcggc       60
ggccaagctt ggcaatccgg tactgttggt aaagccacca tggaagatgc caaaaacatt      120
aagaagggcc cagcgccatt ctacccactc gaagacggga ccgccggcga gcagctgcac      180
```

-continued

```
aaagccatga agcgctacgc cctggtgccc ggcaccatcg cctttaccga cgcacatatc      240
gaggtggaca ttacctacgc cgagtacttc gagatgagcg ttcggctggc agaagctatg      300
aagcgctatg ggctgaatac aaaccatcgg atcgtggtgt gcagcgagaa tagcttgcag      360
ttcttcatgc ccgtgttggg tgccctgttc atcggtgtgg ctgtggcccc agctaacgac      420
atctacaacg agcgcgagct gctgaacagc atgggcatca gccagcccac cgtcgtattc      480
gtgagcaaga aagggctgca aaagatcctc aacgtgcaaa agaagctacc gatcatacaa      540
aagatcatca tcatggatag caagaccgac taccagggct tccaaagcat gtacaccttc      600
gtgacttccc atttgccacc cggcttcaac gagtacgact cgtgcccga gagcttcgac       660 cgggacaaaa ccatcgccct gatcatgaac agtagtggca gtaccggatt gcccaagggc      720
gtagccctac cgcaccgcac cgcttgtgtc cgattcagtc atgcccgcga ccccatcttc      780
ggcaaccaga tcatccccga caccgctatc ctcagcgtgg tgccatttca ccacggcttc      840
ggcatgttca ccacgctggg ctacttgatc tgcggctttc gggtcgtgct catgtaccgc      900
ttcgaggagg agctattctt gcgcagcttg caagactata agattcaatc tgccctgctg      960
gtgcccacac tatttagctt cttcgctaag agcactctca tcgacaagta cgacctaagc     1020
aacttgcacg agatcgccag cggcggggcg ccgctcagca aggaggtagg tgaggccgtg     1080
gccaaacgct tccacctacc aggcatccgc cagggctacg gcctgacaga aacaaccagc     1140
gccattctga tcaccccga aggggacgac aagcctggcg cagtaggcaa ggtggtgccc      1200
ttcttcgagg ctaaggtggt ggacttggac accggtaaga cactgggtgt gaaccagcgc     1260
ggcgagctgt gcgtccgtgg ccccatgatc atgagcggct acgttaacaa ccccgaggct     1320
acaaacgctc tcatcgacaa ggacggctgg ctgcacagcg gcgacatcgc ctactgggac     1380
gaggacgagc acttcttcat cgtggaccgg ctgaagagcc tgatcaaata caagggctac     1440
caggtagccc cagccgaact ggagagcatc ctgctgcaac accccaacat cttcgacgcc     1500
ggggtcgccg gcctgcccga cgacgatgcc ggcgagctgc cgccgcagt cgtcgtgctg      1560 gaacacggta aaaccatgac cgagaaggag atcgtggact atgtggccag ccaggttaca     1620
accgccaaga gctgcgcgg tggtgttgtg ttcgtggacg aggtgcctaa aggactgacc      1680
ggcaagttgg acgcccgcaa gatccgcgag attctcatta aggccaagaa gggcggcaag     1740
atcgccgtgt aataattcta gagtcggggc ggccggccgc ttcgagcaga catgataaga     1800
tacattgatg agtttggaca aaccacaact agaatgcagt gaaaaaaatg ctttatttgt     1860
gaaatttgtg atgctattgc tttatttgta accattataa gctgcaataa acaagttaac     1920
aacaacaatt gcattcattt tatgtttcag gttcaggggg aggtgtggga ggttttttaa     1980
agcaagtaaa acctctacaa atgtggtaaa atcgataagg atccgtcgac cgatgccctt     2040
gagagccttc aacccagtca gctccttccg gtgggcgcgg ggcatgacta tcgtcgccgc     2100
acttatgact gtcttcttta tcatgcaact cgtaggacag gtgccggcag cgctcttccg     2160
cttcctcgct cactgactcg ctgcgctcgg tcgttcggct gcggcgagcg gtatcagctc     2220
actcaaaggc ggtaatacgg ttatccacag aatcagggga taacgcagga agaacatgt      2280 gagcaaaagg ccagcaaaag gccaggaacc gtaaaaaggc cgcgttgctg gcgttttttcc    2340 ataggctccg cccccctgac gagcatcaca aaaatcgacg ctcaagtcag aggtggcgaa     2400
acccgacagg actataaaga taccaggcgt ttccccctgg aagctccctc gtgcgctctc     2460
ctgttccgac cctgccgctt accggatacc tgtccgcctt ctcccttcg ggaagcgtgg      2520 cgctttctca tagctcacgc tgtaggtatc tcagttcggt gtaggtcgtt cgctccaagc     2580
```

| | |
|---|---|
| tgggctgtgt gcacgaaccc cccgttcagc ccgaccgctg cgccttatcc ggtaactatc | 2640 |
| gtcttgagtc caacccggta agacacgact tatcgccact ggcagcagcc actggtaaca | 2700 |
| ggattagcag agcgaggtat gtaggcggtg ctacagagtt cttgaagtgg tggcctaact | 2760 |
| acggctacac tagaagaaca gtatttggta tctgcgctct gctgaagcca gttaccttcg | 2820 |
| gaaaaagagt tggtagctct tgatccggca acaaaccac cgctggtagc ggtggttttt | 2880 |
| ttgtttgcaa gcagcagatt acgcgcagaa aaaaggatc tcaagaagat cctttgatct | 2940 |
| tttctacggg gtctgacgct cagtggaacg aaaactcacg ttaagggatt ttggtcatga | 3000 |
| gattatcaaa aaggatcttc acctagatcc ttttaaatta aaaatgaagt tttaaatcaa | 3060 |
| tctaaagtat atatgagtaa acttggtctg acagcggccg caaatgctaa accactgcag | 3120 |
| tggttaccag tgcttgatca gtgaggcacc gatctcagcg atctgcctat ttcgttcgtc | 3180 |
| catagtggcc tgactccccg tcgtgtagat cactacgatt cgtgagggct taccatcagg | 3240 |
| ccccagcgca gcaatgatgc cgcgagagcc gcgttcaccg gccccgatt tgtcagcaat | 3300 |
| gaaccagcca gcagggaggg ccgagcgaag aagtggtcct gctactttgt ccgcctccat | 3360 |
| ccagtctatg agctgctgtc gtgatgctag agtaagaagt tcgccagtga gtagtttccg | 3420 |
| aagagttgtg gccattgcta ctggcatcgt ggtatcacgc tcgtcgttcg gtatggcttc | 3480 |
| gttcaactct ggttcccagc ggtcaagccg ggtcacatga tcacccatat tatgaagaaa | 3540 |
| tgcagtcagc tccttagggc ctccgatcgt tgtcagaagt aagttggccg cggtgttgtc | 3600 |
| gctcatggta atggcagcac tacacaattc tcttaccgtc atgccatccg taagatgctt | 3660 |
| ttccgtgacc ggcgagtact caaccaagtc gttttgtgag tagtgtatac ggcgaccaag | 3720 |
| ctgctcttgc ccggcgtcta tacgggacaa caccgcgcca catagcagta ctttgaaagt | 3780 |
| gctcatcatc gggaatcgtt cttcggggcg aaagactca aggatcttgc cgctattgag | 3840 |
| atccagttcg atatagccca ctcttgcacc cagttgatct tcagcatctt ttactttcac | 3900 |
| cagcgtttcg gggtgtgcaa aaacaggcaa gcaaatgcc gcaaagaagg gaatgagtgc | 3960 |
| gacacgaaaa tgttggatgc tcatactcgt ccttttcaa tattattgaa gcatttatca | 4020 |
| gggttactag tacgtctctc aaggataagt aagtaatatt aaggtacggg aggtattgga | 4080 |
| caggccgcaa taaatatct ttatttcat tacatctgtg tgttggtttt ttgtgtgaat | 4140 |
| cgatagtact aacatacgct ctccatcaaa acaaaacgaa acaaaacaaa ctagcaaaat | 4200 |
| aggctgtccc cagtgcaagt gcaggtgcca gaacatttct ct | 4242 |

<210> SEQ ID NO 10
<211> LENGTH: 4733
<212> TYPE: DNA
<213> ORGANISM: Artificial Sequence
<220> FEATURE:
<223> OTHER INFORMATION: Sequence of pEGFP-N1 vector (4733 bp)

<400> SEQUENCE: 10

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |

```
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatccaccgg tcgccaccat ggtgagcaag ggcgaggagc tgttcaccgg ggtggtgccc    720
atcctggtcg agctggacgg cgacgtaaac ggccacaagt tcagcgtgtc cggcgagggc    780
gagggcgatg ccacctacgg caagctgacc ctgaagttca tctgcaccac cggcaagctg    840
cccgtgccct ggcccaccct cgtgaccacc ctgacctacg gcgtgcagtg cttcagccgc    900
taccccgacc acatgaagca gcacgacttc ttcaagtccg ccatgcccga aggctacgtc    960
caggagcgca ccatcttctt caaggacgac ggcaactaca agacccgcgc cgaggtgaag   1020
ttcgagggcg acaccctggt gaaccgcatc gagctgaagg gcatcgactt caaggaggac   1080
ggcaacatcc tggggcacaa gctggagtac aactacaaca gccacaacgt ctatatcatg   1140
gccgacaagc agaagaacgg catcaaggtg aacttcaaga tccgccacaa catcgaggac   1200
ggcagcgtgc agctcgccga ccactaccag cagaacaccc catcggcga cggccccgtg   1260 ctgctgcccg acaaccacta cctgagcacc cagtccgccc tgagcaaaga ccccaacgag   1320
aagcgcgatc acatggtcct gctggagttc gtgaccgccg ccgggatcac tctcggcatg   1380
gacgagctgt acaagtaaag cggccgcgac tctagatcat aatcagccat accacatttg   1440
tagaggtttt acttgcttta aaaaacctcc cacacctccc cctgaacctg aaacataaaa   1500
tgaatgcaat tgttgttgtt aacttgttta ttgcagctta taatggttac aaataaagca   1560
atagcatcac aaatttcaca aataaagcat ttttttcact gcattctagt tgtggtttgt   1620
ccaaactcat caatgtatct taaggcgtaa attgtaagcg ttaatatttt gttaaaattc   1680
gcgttaaatt tttgttaaat cagctcattt tttaaccaat aggccgaaat cggcaaaatc   1740
ccttataaat caaaagaata gaccgagata gggttgagtg ttgttccagt ttggaacaag   1800
agtccactat taagaacgt ggactccaac gtcaaagggc gaaaaaccgt ctatcagggc   1860
gatggcccac tacgtgaacc atcaccctaa tcaagttttt tggggtcgag gtgccgtaaa   1920
gcactaaatc ggaaccctaa agggagcccc cgatttagag cttgacgggg aaagccggcg   1980
aacgtggcga gaaaggaagg gaagaaagcg aaaggagcgg cgctagggc gctggcaagt   2040 gtagcggtca cgctgcgcgt aaccaccaca cccgccgcgc ttaatgcgcc gctacagggc   2100
gcgtcaggtg gcacttttcg gggaaatgtg cgcggaaccc ctatttgttt attttctaa   2160 atacattcaa atatgtatcc gctcatgaga caataaccct gataaatgct tcaataatat   2220
tgaaaaagga agagtcctga gcggaaaga accagctgtg aatgtgtgt cagttagggt   2280 gtggaaagtc cccaggctcc ccagcaggca gaagtatgca aagcatgcat ctcaattagt   2340
cagcaaccag gtgtggaaag tccccaggct cccccagcagg cagaagtatg caaagcatgc   2400
atctcaatta gtcagcaacc atagtcccgc ccctaactcc gcccatcccg ccctaactc   2460 cgcccagttc cgcccattct ccgccccatg gctgactaat ttttttttatt tatgcagagg   2520 ccgaggccgc ctcggcctct gagctattcc agaagtagtg aggaggcttt tttggaggcc   2580
taggcttttg caaagatcga tcaagagaca ggatgaggat cgtttcgcat gattgaacaa   2640
gatggattgc acgcaggttc tccggccgct tgggtggaga ggctattcgg ctatgactgg   2700
gcacaacaga caatcggctg ctctgatgcc gccgtgttcc ggctgtcagc gcaggggcgc   2760
```

```
ccggttctttt tgtcaagac cgacctgtcc ggtgccctga atgaactgca agacgaggca    2820
gcgcggctat cgtggctggc cacgacgggc gttccttgcg cagctgtgct cgacgttgtc    2880
actgaagcgg gaagggactg gctgctattg ggcgaagtgc ggggcagga tctcctgtca    2940 tctcaccttg ctcctgccga aaagtatcc atcatggctg atgcaatgcg gcggctgcat    3000
acgcttgatc cggctacctg cccattcgac caccaagcga acatcgcat cgagcgagca    3060 cgtactcgga tggaagccgg tcttgtcgat caggatgatc tggacgaaga gcatcagggg    3120
ctcgcgccag ccgaactgtt cgccaggctc aaggcgagca tgcccgacgg cgaggatctc    3180
gtcgtgaccc atggcgatgc ctgcttgccg aatatcatgg tggaaaatgg ccgcttttct    3240
ggattcatcg actgtggccg gctgggtgtg gcggaccgct atcaggacat agcgttggct    3300
acccgtgata ttgctgaaga gcttggcggc gaatgggctg accgcttcct cgtgctttac    3360
ggtatcgccg ctcccgattc gcagcgcatc gccttctatc gccttcttga cgagttcttc    3420
tgagcgggac tctggggttc gaaatgaccg accaagcgac gcccaacctg ccatcacgag    3480
atttcgattc caccgccgcc ttctatgaaa ggttgggctt cggaatcgtt ttccgggacg    3540
ccggctggat gatcctccag cgcggggatc tcatgctgga gttcttcgcc caccctaggg    3600
ggaggctaac tgaaacacgg aaggagacaa taccggaagg aacccgcgct atgacggcaa    3660
taaaaagaca gaataaaacg cacggtgttg ggtcgtttgt tcataaacgc ggggttcggt    3720
cccagggctg gcactctgtc gataccccac cgagacccca ttggggccaa tacgcccgcg    3780
tttcttcctt ttccccaccc cacccccaa gttcgggtga aggcccaggg ctcgcagcca    3840 acgtcgggc ggcaggccct gccatagcct caggttactc atatatactt tagattgatt    3900
taaaacttca ttttttaattt aaaaggatct aggtgaagat cctttttgat aatctcatga    3960
ccaaaatccc ttaacgtgag ttttcgttcc actgagcgtc agaccccgta gaaaagatca    4020
aaggatcttc ttgagatcct ttttttctgc gcgtaatctg ctgcttgcaa acaaaaaaac    4080
caccgctacc agcggtggtt tgtttgccgg atcaagagct accaactctt tttccgaagg    4140
taactggctt cagcagagcg cagataccaa atactgtcct tctagtgtag ccgtagttag    4200
gccaccactt caagaactct gtagcaccgc ctacatacct cgctctgcta atcctgttac    4260
cagtggctgc tgccagtggc gataagtcgt gtcttaccgg gttggactca agacgatagt    4320
taccggataa ggcgcagcgg tcgggctgaa cggggggttc gtgcacacag cccagcttgg    4380
agcgaacgac ctacaccgaa ctgagatacc tacagcgtga gctatgagaa agcgccacgc    4440
ttcccgaagg gagaaaggcg gacaggtatc cggtaagcgg cagggtcgga acaggagagc    4500
gcacgaggga gcttccaggg ggaaacgcct ggtatcttta tagtcctgtc gggtttcgcc    4560
acctctgact tgagcgtcga ttttgtgat gctcgtcagg ggggcggagc ctatggaaaa    4620
acgccagcaa cgcggccttt ttacggttcc tggccttttg ctggccttt gctcacatgt    4680 tctttcctgc gttatcccct gattctgtgg ataaccgtat taccgccatg cat    4733
```

<210> SEQ ID NO 11
<211> LENGTH: 2579
<212> TYPE: DNA
<213> ORGANISM: Artificial Sequence
<220> FEATURE:
<223> OTHER INFORMATION: Sequence of pDsRed2-N1 vector (4689 bp)

<400> SEQUENCE: 11

```
tctagatggg gcaactggag atgatgggag aagaaagcct aagggactaa gaggaaagcc      60
```

```
acaatctgtc ggtaaatcct gccttgggta gaatcttcta aacctttccc gctttcagca      120
ctcttatcct gtcccacagg caaaggggag ttttaaaatc tcctctccat caccatcttg      180
tgttccgccc tggttcctaa ttgtcttact tgagccattc actccatcca gccgagacct      240
tgttttagca gacacacaac tgcctagagt ctacacgccc ctcccttccc caaactaaag      300
tgcttaggga cccagaaaat aggccaggtc ctcgtaacct tatcgaaata gcacagctag      360
gccttccacc caacaacact cagagactgg gccatagggt aggaaacagc atccagagtc      420
ttgtccagac agagcccaga catcttctgt agttaagagc cctctgggta ttctcacgtc      480
ctgccccaaa aaaggaacc aagcttatct ggggcggtg gggagaaggg ggtgtaagcc        540
aaagctaaag caactaaagc aactgtgttc tgataggaaa gatccctgga ctgagaacaa      600
gaaagctgtt ccgcaggaaa gaacacactg cgtggagtgt cagggaggag gccagcacct      660
ctggaatgcg gcaggaagat gaatgggaaa gatgaggtgg tggtggaggg cagcagccag      720
ggccttcaaa atcatcctcc agacaatgac aagcccggtc acctgatctg tgaagaggga      780
tggtctgcaa tctccaggcc ctcgagcctg tgcaaagggc aggctcaggc agctctgctg      840
ctagactaag gacatcccag gtgggcacgg agagctgcat ttctcgtaaa gcgccctagg      900
agcttctgtt gttcaccaga accacgagcc cctggactgg accgttcaca aggctcgttc      960
cagttagaaa attccatcac tctaagagct gggaggcacc taacctccaa gggagggaga     1020
gggaagtgga tctcccactt gccagcccag ggatgacttc caacagtgcc attacagtaa     1080
tggaaactgc agtgaaggtg ccagggctga cttctgtgaa gaaagaggag gacaggagtt     1140
cccctagtgg ctcatcagaa atgaatctga ctagcatcca tgaggatgca ggttcaatcc     1200
ctggcctcat tcagtggctt aaggatccag cgttgccgag agctgtgatg taggtcacag     1260
acgcggctca gatcccgtgt tgctgttgct gtggctgtgg cataggtcag aagcgacagc     1320
tctgatttga cccctaacct gggaacctcc atatcccgct agtgcggccc ttaaaagaca     1380
aaaagaagga aaagagaaga aaagacatag gcgaacagaa aggcagatga cagggtggca     1440
gggccagcct acacgatggc ccgaccagaa ttcacaaaga agccacaagg atgcaaatca     1500
atcaaataaa cctttgttca aaaaaattta tctcacctgt gagtgggaga gacaagtcac     1560
cccagggctt ctggtgactt caaattgata gggagaaaat ggttgcccca ggggattaaa     1620
agcttggtat ctgctactcc tttagagttg gcctgtctcc tccactttcc cacaattcca     1680
ccatttcccc ctcccactgg gctgggatgc agctgtggag tggctcagct ccaaggacta     1740
ggggctccac agcccaggtc cggcggccag ccctcccact tccagcctgg aagtgggatg     1800
gggagtggga tgagatgaac ccggcagatt gtagccacag atgtggatgt gcagggtcca     1860
gcacagggct tgggtgagga gggcggcacc ccatcccttg tctgaagacc aagcagacag     1920
tactcaggac ttgggagggg gttggggag gaggagtgca tgaaactgag aagaaccttc      1980
tagctgcctg cgccaggagg tacccggag ctgaaggaga tggagtgccc cagagcagaa      2040
agcccctgca ggtctggatg ttctaggctg gatgaggggg cgaggcaggc ctggggacct     2100
gggaagacca ggcgcagtac ctgccttgct tctgaaaatg ctgctccaac gtggaaaaac     2160
actcccacca tctttctttg gagaaagcct gtaatattcc aacaccaaaa cctctcacta     2220
gaggttcccg tggagatggg ttccagatga aaagggaagg aggaggcatg ggcgctgcct     2280
aacctccatc ctcccattcct tacccctctc ccaccggctt ctgaagccgg gtcagaaga    2340 aagggttaaa gccttaaaag gggaccgatt ttgcggggct ctgggggtcg gctgcacac     2400 cctgagcggc cccgcccttc tctctagtgt ccagaaccct ccctgccctg cccaggccta    2460
```

-continued

```
acggccacag ggggagggcc cccctttact gcagaccgcc actctcccac accaatatcg      2520
gaccgcctcc tcctccctct gccaccccct ctcgctcccc actcagcctc tgattggcc       2579

<210> SEQ ID NO 12
<211> LENGTH: 13874
<212> TYPE: DNA
<213> ORGANISM: Artificial Sequence
<220> FEATURE:
<223> OTHER INFORMATION: multicistronic vector of pTet retrovirus

<400> SEQUENCE: 12
tttgaaagac cccacccgta ggtggcaagc tagcttaagt aacgccactt tgcaaggcat         60
ggaaaaatac ataactgaga atagaaaagt tcagatcaag gtcaggaaca agaaacagc        120 tgaataccaa acaggatatc tgtggtaagc ggttcctgcc ccggctcagg gccaagaaca       180
gatgagacag ctgagtgatg ggccaaacag gatatctgtg gtaagcagtt cctgccccgg       240
ctcggggcca agaacagatg gtccccagat gcggtccagc cctcagcagt ttctagtgaa       300
tcatcagatg tttccagggt gccccaagga cctgaaaatg accctgtacc ttatttgaac      360
taaccaatca gttcgcttct cgcttctgtt cgcgcgcttc cgctctccga gctcaataaa       420
agagcccaca acccctcact cggcgcgcca gtcttccgat agactgcgtc gcccgggtac       480
ccgtattccc aataaagcct cttgctgttt gcatccgaat cgtggtctcg ctgttccttg       540
ggagggtctc ctctgagtga ttgactaccc acgacggggg tctttcattt gggggctcgt      600 ccggatttg gagaccccctg cccagggacc accgacccac caccgggagg taagctggcc       660
agcaacttat ctgtgtctgt ccgattgtct agtgtctatg tttgatgtta tgcgcctgcg       720
tctgtactag ttagctaact agctctgtat ctggcggacc cgtggtggaa ctgacgagtt       780
ctgaacaccc ggccgcaacc ctgggagacg tcccaggggac tttggggggcc gttttttgtgg     840 cccgacctga ggaagggagt cgatgtgaaa tccgaccccg tcaggatatg tggttctggt       900
aggagacgag aacctaaaac agttcccgcc tccgtctgaa ttttttgcttt cggtttggaa      960 ccgaagccgc gcgtcttgtc tgctgcagcc ctgcagcatc gttctgtgtt gtctctgtct      1020
gactgtgttt ctgtatttgt ctgaaaatta gggccagact gttaccactc ccttaagttt      1080
gaccttaggt cactgaaaag atgtcgagcg gatcgctcac aaccagtcgg tagatgtcaa      1140
gaagagacgt tgggttacct tctgctctgc agaatggcca acctttaacg tcggatggcc      1200
gcgagacggc acctttaacc gagacctcat cacccaggtt aagatcaagg tcttttcacc      1260
tggcccgcat ggacacccag accaggtccc ctacatcgtg acctgggaag ccttggcttt     1320
tgacccccct ccctgggtca agcccttttgt acaccctaag cctccgcctc ctcttcctcc      1380
atccgccccg tctctccccc ttgaacctcc tcgttcgacc ccgcctcgat cctcccttta      1440
tccagccctc actccttctc taggcgccgg aattccgatc tgatagcttg ccacaacccg       1500
taccaaagat ggatagatcc ggaaagcctg aactcaccgc gacgtctgtc gagaagtttc      1560
tgatcgaaaa gttcgacagc gtctccgacc tgatgcagct ctcggagggc gaagaatctc      1620
gtgctttcag cttcgatgta ggagggcgtg gatatgtcct gcgggtaaat agctgcgccg      1680
atggtttcta caaagatcgt tatgtttatc ggcactttgc atcggccgcg ctcccgattc      1740
cggaagtgct tgacattggg gaattcagcg agagcctgac ctattgcatc tcccgccgtg      1800
cacagggtgt cacgttgcaa gacctgcctg aaaccgaact gcccgctgtt ctgcagccgg      1860
tcgcggaggc catggatgcg atcgctgcgg ccgatcttag ccagacgagc gggttcggcc      1920
```

-continued

```
cattcggacc gcaaggaatc ggtcaataca ctacatggcg tgatttcata tgcgcgattg    1980
ctgatcccca tgtgtatcac tggcaaactg tgatggacga caccgtcagt gcgtccgtcg    2040
cgcaggctct cgatgagctg atgctttggg ccgaggactg ccccgaagtc cggcacctcg    2100
tgcacgcgga tttcggctcc aacaatgtcc tgacggacaa tggccgcata acagcggtca    2160
ttgactggag cgaggcgatg ttcggggatt cccaatacga ggtcgccaac atcttcttct    2220
ggaggccgtg gttggcttgt atggagcagc agacgcgcta cttcgagcgg aggcatccgg    2280
agcttgcagg atcgccgcgg ctccgggcgt atatgctccg cattggtctt gaccaactct    2340
atcagagctt ggttgacggc aatttcgatg atgcagcttg ggcgcagggt cgatgcgacg    2400
caatcgtccg atccggagcc gggactgtcg ggcgtacaca aatcgcccgc agaagcgcgg    2460
ccgtctggac cgatggctgt gtagaagtac tcgccgatag tggaaaccga cgccccagca    2520
ctcgtccgag ggcaaaggaa tagagtagat gccgaccgaa caagagctga tttcgagaac    2580
gcctcagcca gcaactcgcg cgagcctagc aaggcaaatg cgagagaacg gccttacgct    2640
tggtggcaca gttctcgtcc acagttcgct aagctcgctc ggctgggtcg cgggagggcc    2700
ggtcgcagtg attcaggccc ttctggattg tgttggtccc cagggcacga ttgtcatgcc    2760
cacgcactcg ggtgatctga ctgatcccgc agattggaga tcgccgcccg tgcctgccga    2820
ttgggtgcag atctatttaa atatcaaata aacctttgtt caaaaaaatt tatctcacct    2880
gtgagtggga gagacaagtc accccagggc ttctggtgac ttcaaattga tagggagaaa    2940
atggttgccc caggggatta aaagcttggt atctgctact cctttagagt tggcctgtct    3000
cctccacttt cccacaattc caccatttcc ccctcccact gggctgggat gcagctgtgg    3060
agtggctcag ctccaaggac taggggctcc acagcccagg tccggcggcc agccctccca    3120
cttcagcct ggaagtggga tggggagtgg atgagatga accggcaga ttgtagccac    3180
agatgtggat gtgcagggtc cagcacaggg cttgggtgag gagggcggca ccccatccct    3240
tgtctgaaga ccaagcagac agtactcagg acttgggagg gggttggggg aggaggagtg    3300
catgaaactg agaagaacct tctagctgcc tgcgccagga ggtacccggg agctgaagga    3360
gatggagtgc cccagagcag aaagcccctg caggtctgga tgttctaggc tggatgaggg    3420
ggcgaggcag gcctggggac ctgggaagac caggcgcagt acctgccttg cttctgaaaa    3480
tgctgctcca acgtggaaaa acactcccac catctttctt tggagaaagc ctgtaatatt    3540
ccaacaccaa aacctctcac tagaggttcc cgtggagatg ggttccagat gaaaagggaa    3600
ggaggaggca tgggcgctgc ctaacctcca tcctccattc cttacccctc tcccaccggc    3660
ttctgaagcc ggggtcagaa gaaagggtta aagccttaaa aggggaccga ttttgcgggg    3720
ctctgggggt cggctggcac accctgagcg gccccgccct tctctctagt gtccagaacc    3780
ctccctgccc tgcccaggcc taacggccac aggggagggg ccccccttta ctgcagaccg    3840
ccactctccc acaccaatat cggaccgcct cctcctccct ctgccacccc ttctcgctcc    3900
ccactcagcc tctgattggc catcgatatg ctgcccggtt tggcactgct cctgctggcc    3960
gcctggacgg ctcgggcgct ggaggtaccc actgatggta atgctggcct gctggctgaa    4020
ccccagattg ccatgttctg tggcagactg aacatgcaca tgaatgtcca gaatgggaag    4080
tgggattcag atccatcagg gaccaaaacc tgcattgata ccaaggaagg catcctgcag    4140
tattgccaag aagtctaccc tgaactgcag atcaccaatg tggtagaagc caaccaacca    4200
gtgaccatcc agaactggtg caagcggggc cgcaagcagt gcaagaccca tcccactttt    4260
gtgattccct accgctgctt agttggtgag tttgtaagtg atgcccttct cgttcctgac    4320
```

-continued

```
aagtgcaaat tcttacacca ggagaggatg gatgtttgcg aaactcatct tcactggcac    4380
accgtcgcca aagagacatg cagtgagaag agtaccaact tgcatgacta cggcatgttg    4440
ctgccctgcg gaattgacaa gttccgaggg gtagagtttg tgtgttgccc actggctgaa    4500
gaaagtgaca atgtggattc tgctgatgcg gaggaggatg actcggatgt ctggtggggc    4560
ggagcagaca cagactatgc agatgggagt gaagacaaag tagtagaagt agcagaggag    4620
gaagaagtgg ctgaggtgga agaagaagaa gccgatgatg acgaggacga tgaggatggt    4680
gatgaggtag aggaagaggc tgaggaaccc tacgaagaag ccacagagag aaccaccagc    4740
attgccacca ccaccaccac caccacagag tctgtggaag aggtggttcg agttcctaca    4800
acagcagcca gtacccctga tgccgttgac aagtatctcg agacacctgg ggatgagaat    4860
gaacatgccc atttccagaa agccaaagag aggcttgagg ccaagcaccg agagagaatg    4920
tcccaggtca tgagagaatg ggaagaggca gaacgtcaag caaagaactt gcctaaagct    4980
gataagaagg cagttatcca gcatttccag gagaaagtgg aatctttgga acaggaagca    5040
gccaacgaga gacagcagct ggtggagaca cacatggcca gagtggaagc catgctcaat    5100
gaccgccgcc gcctggccct ggagaactac atcaccgctc tgcaggctgt tcctcctcgg    5160
cctcgtcacg tgttcaatat gctaaagaag tatgtccgcg cagaacagaa ggacagacag    5220
cacacccta agcatttcga gcatgtgcgc atggtggatc ccaagaaagc cgctcagatc    5280
cggtcccagg ttatgacaca cctccgtgtg atttatgagc gcatgaatca gtctctctcc    5340
ctgctctaca acgtgcctgc agtggccgag gagattcagg atgaagttga tgagctgctt    5400
cagaaagagc aaaactattc agatgacgtc ttggccaaca tgattagtga accaaggatc    5460
agttacggaa acgatgctct catgccatct ttgaccgaaa cgaaaaccac cgtggagctc    5520
cttcccgtga atggagagtt cagcctggac gatctccagc cgtggcattc tttgggggct    5580
gactctgtgc cagccaacac agaaaacgaa gttgagcctg ttgatgcccg ccctgctgcc    5640
gaccgaggac tgaccactcg accaggttct ggggttgacaa atatcaagac ggaggagatc    5700
tctgaagtga atctggatgc agaattccga catgactcag gatatgaagt tcatcatcaa    5760
aaattggtgt tctttgcaga agatgtgggt tcaaacaaag gtgcaatcat ggactcatg    5820
gtgggcggtg ttgtcatagc gacagtggtc atcatcacct tggtgatgct gaagaagaaa    5880
cagtacacat ccattcatca tggtgtggtg gaggttgacg ccgctgtcac cccagaggag    5940
cgccacctgt ccaatctgca gcagaacggc tacgaaaatc caacctacaa gttctttgag    6000
cagatgcaga acttaattaa ggcatgcgga agcggagcta ctaacttcag cctgctgaag    6060
caggctggag acgtggagga gaaccctgga cctagatcta tggctgagcc ccgccaggag    6120
ttcgaagtga tggaagatca cgctgggacg tacgggttgg gggacaggaa agatcagggg    6180
ggctacacca tgcaccaaga ccaagagggt gacacggacg ctggcctgaa agctgaagaa    6240
gcaggcattg agacacccc cagcctggaa gacgaagctg ctggtcacgt gacccaagct    6300
cgcatggtca gtaaaagcaa agacgggact ggaagcgatg acaaaaaagc caggggggct    6360
gatggtaaaa cgaagatcgc cacaccgcgg ggagcagccc ctccaggcca gaagggccag    6420
gccaacgcca ccaggattcc agcaaaaacc ccgcccgctc aaagacacc cccagctct    6480
ggtgaacctc caaaatcagg ggatcgcagc ggctacagca gccccggctc cccaggcact    6540
cccggcagcc gctcccgcac cccgtcccctt ccaaccccac ccaccgggga gcccaagaag    6600
gtggcagtgg tccgtactcc acccaagtcg ccgtcttccg ccaagagccg cctgcagaca    6660
```

```
gccccgtgc ccatgccaga cctgaagaat gtcaagtcca agatcggctc cactgagaac    6720
ctgaagcacc agccgggagg cgggaaggtg cagataatta ataagaagct ggatcttagc    6780
aacgtccagt ccaagtgtgg ctcaaaggat aatatcaaac acgtcctggg aggcggcagt    6840
gtgcaaatag tctacaaacc agttgacctg agcaaggtga cctccaagtg tggctcatta    6900
ggcaacatcc atcataaacc aggaggtggc caggtggaag taaaatctga gaagcttgac    6960
ttcaaggaca gagtccagtc gaagattggg tccctggaca atatcaccca cgtccctggc    7020
ggaggaaata aaaagattga aacccacaag ctgaccttcc gcgagaacgc caaagccaag    7080
acagaccacg gggcggagat cgtgtacaag tcgccagtgg tgtctgggga cacgtctcca    7140
cggcatctca gcaatgtctc ctccaccggc agcatcgaca tggtagactc gccccagctc    7200
gccacgctag ctgacgaggt gtctgcctcc ctggccaagc agggtttgga attcggaagc    7260
ggagctacta acttcagcct gctgaagcag gctggagacg tggaggagaa ccctggacct    7320
ctcgagatga cagagttacc tgcaccgttg tcctacttcc agaatgcaca gatgtctgag    7380
gacaaccacc tgagcaatac tgtacgtagc cagaatgaca atagagaacg gcaggagcac    7440
aacgacagac ggagccttgg ccaccctgag ccattatcta atggacgacc ccagggtaac    7500
tcccggcagg tggtggagca agatgaggaa gaagatgagg agctgacatt gaaatatggc    7560
gccaagcatg tgatcatgct ctttgtccct gtgactctct gcatggtggt ggtcgtggct    7620
accattaagt cagtcagctt ttatacccgg aaggatgggc agctaatcta taccccattc    7680
acagaagata ccgagactgt gggccagaga gccctgcact caattctgaa tgctgccatc    7740
atgatcagtc tcattgttgt cctgactatc ctcctggtgg ttctgtataa atacaggtgc    7800
tataaggtca tccatgcctg gcttattata tcatctctat tgttgctgtt ctttttttca    7860
ttcatttact tggggaagt gtttaaaacc tataacgttg ctgtggacta cattactgtt    7920
gcactcctga tctggaattt tggtgtggtg ggaatgattt ccattcactg gaaaggtcca    7980
cttcgactcc agcaggcata tctcattatg attagtgccc tcatggccct ggtgtttatc    8040
aagtacctcc ctgaatggac tgcgtggctc atcttggctg tgatttcagt atatgattta    8100
gtggctgttt tgtgtccgaa aggtccactt cgtatgctgg ttgaaacagc tcaggagaga    8160
aatgaaacgc tttttccagc tgtcatttac tcctcaacaa tggtgtggtt ggtgaatatg    8220
gcagaaggag acccggaagc tcaaaggaga gtatccaaaa attccaagta taatgcagaa    8280
agcacagaaa gggagtcaca agacactgtt gcagagaatg atgatggcgg gttcagtgag    8340
gaatgggaag cccagaggga cagtcatcta gggcctcatc gctctacacc tgagtcacga    8400
gctgctgtcc aggaactttc cagcagtatc ctcgctggtg aagacccaga ggaaagggga    8460
gtaaaacttg gattgggaga tttcattttc tacagtgttc tggttggtaa agcctcagca    8520
acagccagtg gagactggaa cacaaccata gcctgtttcg tagccatatt aattggtttg    8580
tgccttacat tattactcct tgccattttc aagaaagcat tgccagctct tccaatctcc    8640
atcacctttg ggcttgtttt ctactttgcc acagattatc ttgtacagcc ttttatggac    8700
caattagcat tccatcaatt ttatatctag cctgcaggtc tagatagcta gcctccctat    8760
agtgagtcgt attacgtaga tccagacatg ataagataca ttgatgagtt tggacaaacc    8820
acaactagaa tgcagtgaaa aaaatgcttt atttgtgaaa tttgtgatgc tattgcttta    8880
tttgtaacca ttataagctg caataaacaa gttaacaaca acaattgcat tcattttatg    8940
tttcaggttc aggggaggt gtgggaggtt ttttaattcg cggccgcctc gagagatccc    9000
ctcaggatat agtagtttcg cttttgcata gggagggggga aatgtagtct tatgcaatac    9060
```

```
tcttgtagtc ttgcaacatg gtaacgatga gttagcaaca tgccttacaa ggagagaaaa    9120
agcaccgtgc atgccgattg gtggaagtaa ggtggtacga tcgtgcctta ttaggaaggc    9180
aacagacggg tctgacatgg attggacgaa ccactgaatt ccgcattgca gagatattgt    9240
atttaagtgc ctagctcgat acagcaaacg ccatttgacc attcaccaca ttggtgtgca    9300
cctccaagct tgttaattca ccatgtctag actggacaag agcaaagtca taaacggcgc    9360
tctggaatta ctcaatggag tcggtatcga aggcctgacg acaaggaaac tcgctcaaaa    9420
gctgggagtt gagcagccta ccctgtactg gcacgtgaag aacaagcggg ccctgctcga    9480
tgccctgcca atcgagatgc tggacaggca tcatacccac ttctgccccc tggaaggcga    9540
gtcatggcaa gactttctgc ggaacaacgc caagtcattc cgctgtgctc tcctctcaca    9600
tcgcgacggg gctaaagtgc atctcggcac ccgcccaaca gagaaacagt acgaaaccct    9660
ggaaaatcag ctcgcgttcc tgtgtcagca aggcttctcc ctggagaacg cactgtacgc    9720
tctgtccgcc gtgggccact ttacactggg ctgcgtattg gaggaacagg agcatcaagt    9780
agcaaaagag gaaagagaga cacctaccac cgattctatg cccccacttc tgagacaagc    9840
aattgagctg ttcgaccggc agggagccga acctgccttc cttttcggcc tggaactaat    9900
catatgtggc ctggagaaac agctaaagtg cgaaagcggc gggccggccg acgcccttga    9960
cgattttgac ttagacatgc tcccagccga tgcccttgac gactttgacc ttgatatgct    10020
gcctgctgac gctcttgacg attttgacct tgacatgctc cccgggtaac taagtaagga    10080
tcaacatcga attcgatttc tgttcctgtt aatcaacctc tggattacaa aatttgtgaa    10140
agattgactg gtattcttaa ctatgttgct ccttttacgc tatgtggata cgctgcttta    10200
atgcctttgt atcatgctat tgcttcccgt atggctttca ttttctcctc cttgtataaa    10260
tcctggttgc tgtctcttta tgaggagttg tggcccgttg tcaggcaacg tggcgtggtg    10320
tgcactgtgt ttgctgacgc aacccccact ggttggggca ttgccaccac ctgtcagctc    10380 cttttccggga ctttcgcttt cccctccct attgccacgg cggaactcat cgccgcctgc    10440
cttgcccgct gctggacagg ggctcggctg ttgggcactg acaattccgt ggtgttgtcg    10500
gggaagctga cgtcctttcc atggctgctc gcctgtgttg ccacctggat tctgcgcggg    10560
acgtccttct gctacgtccc ttcggccctc aatccagcgg accttccttc ccgcggcctg    10620
ctgccggctc tgcggcctct tccgcgtctt cgccttcgcc ctcagacgag tcggatctcc    10680
ctttgggccg cctccccgcc tgtttcgcct cgggctcaat cactagtgaa ttcgataaaa    10740
taaaagattt tatttagtct ccagaaaaag ggggaatga aagaccccac ctgtaggttt    10800
ggcaagctag cttaagtaac gccatttttgc aaggcatgga aaatacata actgagaata    10860 gagaagttca gatcaaggtc aggaacagat ggaacagctg aatatgggcc aaacaggata    10920
tctgtggtaa gcagttcctg ccccggctca gggccaagaa cagatggaac agctgaatat    10980
gggccaaaca ggatatctgt ggtaagcagt tcctgccccg gctcagggcc aagaacagat    11040
ggtccccaga tgcggtccag ccctcagcag tttctagaga accatcagat gtttccaggg    11100
tgccccaagg acctgaaatg accctgtgcc ttatttgaac taaccaatca gttcgcttct    11160
cgcttctgtt cgcgcgcttc tgctccccga gctcaataaa agagcccaca ccccctcact    11220
cggggcgcca gtcctccgat tgactgagtc gcccgggtac ccgtgtatcc aataaaccct    11280
cttgcagttg catccgactt gtggtctcgc tgttccttgg gagggtctcc tctgagtgat    11340
tgactacccg tcagcggggg tctttcattt gggggctcgt ccgggatcgg gagacccctg    11400
```

```
cccagggacc accgacccac caccgggagg taagctggct gcctcgcgcg tttcggtgat    11460
gacggtgaaa acctctgaca catgcagctc ccggagacgg tcacagcttg tctgtaagcg    11520
gatgccggga gcagacaagc ccgtcagggc gcgtcagcgg gtgttggcgg gtgtcgggc    11580 gcagccatga cccagtcacg tagcgatagc ggagtgtata ctggcttaac tatgcggcat    11640
cagagcagat tgtactgaga gtgcaccata tgcggtgtga aataccgcac agatgcgtaa    11700
ggagaaaata ccgcatcagg cgctcttccg cttcctcgct cactgactcg ctgcgctcgg    11760
tcgttcggct gcggcgagcg gtatcagctc actcaaaggc ggtaatacgg ttatccacag    11820
aatcagggga taacgcagga agaacatgt gagcaaaagg ccagcaaaag gccaggaacc    11880
gtaaaaaggc cgcgttgctg gcgttttcc ataggctccg ccccctgac gagcatcaca    11940 aaaatcgacg ctcaagtcag aggtggcgaa acccgacagg actataaaga taccaggcgt    12000
ttccccctgg aagctccctc gtgcgctctc ctgttccgac cctgccgctt accggatacc    12060
tgtccgcctt tctcccttcg ggaagcgtgg cgctttctca tagctcacgc tgtaggtatc    12120
tcagttcggt gtaggtcgtt cgctccaagc tgggctgtgt gcacgaaccc cccgttcagc    12180
ccgaccgctg cgccttatcc ggtaactatc gtcttgagtc caacccggta agacacgact    12240
tatcgccact ggcagcagcc actggtaaca ggattagcag agcgaggtat gtaggcggtg    12300
ctacagagtt cttgaagtgg tggcctaact acggctacac tagaaggaca gtatttggta    12360
tctgcgctct gctgaagcca gttaccttcg gaaaaagagt tggtagctct tgatccggca    12420
aacaaaccac cgctggtagc ggtggttttt ttgtttgcaa gcagcagatt acgcgcagaa    12480
aaaaaggatc tcaagaagat cctttgatct tttctacggg gtctgacgct cagtggaacg    12540
aaaactcacg ttaagggatt ttggtcatga gattatcaaa aaggatcttc acctagatcc    12600
ttttaaatta aaaatgaagt tttaaatcaa tctaaagtat atatgagtaa acttggtctg    12660
acagttacca atgcttaatc agtgaggcac ctatctcagc gatctgtcta tttcgttcat    12720
ccatagttgc ctgactcccc gtcgtgtaga taactacgat acgggagggc ttaccatctg    12780
gccccagtgc tgcaatgata ccgcgagacc cacgctcacc ggctccagat ttatcagcaa    12840
taaaccagcc agccggaagg gccgagcgca gaagtggtcc tgcaacttta tccgcctcca    12900
tccagtctat taattgttgc cgggaagcta gagtaagtag ttcgccagtt aatagtttgc    12960
gcaacgttgt tgccattgct gcaggcatcg tggtgtcacg ctcgtcgttt ggtatggctt    13020
cattcagctc cggttcccaa cgatcaaggc gagttacatg atcccccatg ttgtgcaaaa    13080
aagcggttag ctccttcggt cctccgatcg ttgtcagaag taagttggcc gcagtgttat    13140
cactcatggt tatggcagca ctgcataatt ctcttactgt catgccatcc gtaagatgct    13200
tttctgtgac tggtgagtac tcaaccaagt cattctgaga atagtgtatg cggcgaccga    13260
gttgctcttg cccggcgtca acacgggata ataccgcgcc acatagcaga actttaaaag    13320
tgctcatcat tggaaaacgt tcttcggggc gaaaactctc aaggatctta ccgctgttga    13380
gatccagttc gatgtaaccc actcgtgcac ccaactgatc ttcagcatct tttactttca    13440
ccagcgtttc tgggtgagca aaaacaggaa ggcaaaatgc cgcaaaaaag gaataagggc    13500 gacacggaa atgttgaata ctcatactct ccttttttca atattattga agcatttatc    13560
agggttattg tctcatgagc ggatacatat ttgaatgtat ttagaaaaat aaacaaatag    13620
gggttccgcg cacatttccc cgaaaagtgc cacctgacgt ctaagaaacc attattatca    13680
tgacattaac ctataaaaat aggcgtatca cgaggccctt tcgtcttcaa gaattcatac    13740
cagatcaccg aaaactgtcc tccaaatgtg tcccctcac actcccaaat tcgcgggctt    13800
```

```
ctgcctctta gaccactcta ccctattccc cacactcacc ggagccaaag ccgcggccct    13860
tccgtttctt tgct                                                     13874

<210> SEQ ID NO 13
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 13
attaattcta gatggggcaa ctggag                                        26

<210> SEQ ID NO 14
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 14
gctagcggcc aatcagaggc tgag                                          24

<210> SEQ ID NO 15
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 15
gagctctcta gatggggcaa ctggag                                        26

<210> SEQ ID NO 16
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 16
gctagcggcc aatcagaggc tgag                                          24

<210> SEQ ID NO 17
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 17
ggtaccaacc tccatcctcc attcct                                        26

<210> SEQ ID NO 18
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 18
ctcgagggtg ggaatcagcc aagag                                         25

<210> SEQ ID NO 19
```

<211> LENGTH: 2085
<212> TYPE: DNA
<213> ORGANISM: Artificial Sequence
<220> FEATURE:
<223> OTHER INFORMATION: APP cDNA

<400> SEQUENCE: 19

| | |
|---|---:|
| atgctgcccg gtttggcact gctcctgctg ccgcctgga cggctcgggc gctggaggta | 60 |
| cccactgatg gtaatgctgg cctgctggct gaacccaga ttgccatgtt ctgtggcaga | 120 |
| ctgaacatgc acatgaatgt ccagaatggg aagtgggatt cagatccatc agggaccaaa | 180 |
| acctgcattg ataccaagga aggcatcctg cagtattgcc aagaagtcta ccctgaactg | 240 |
| cagatcacca atgtggtaga agccaaccaa ccagtgacca tccagaactg gtgcaagcgg | 300 |
| ggccgcaagc agtgcaagac ccatccccac tttgtgattc cctaccgctg cttagttggt | 360 |
| gagtttgtaa gtgatgccct ctcgttcct gacaagtgca aattcttaca ccaggagagg | 420 |
| atggatgttt gcgaaactca tcttcactgg cacaccgtcg ccaaagagac atgcagtgag | 480 |
| aagagtacca acttgcatga ctacggcatg ttgctgccct gcggaattga caagttccga | 540 |
| ggggtagagt ttgtgtgttg cccactggct gaagaaagtg acaatgtgga ttctgctgat | 600 |
| gcggaggagg atgactcgga tgtctggtgg ggcggagcag acacagacta tgcagatggg | 660 |
| agtgaagaca aagtagtaga agtagcagag gaggaagaag tggctgaggt ggaagaagaa | 720 |
| gaagccgatg atgacgagga cgatgaggat ggtgatgagg tagaggaaga ggctgaggaa | 780 |
| ccctacgaag aagccacaga gagaaccacc agcattgcca ccaccaccac caccaccaca | 840 |
| gagtctgtgg aagaggtggt tcgagttcct acaacagcag ccagtaccc tgatgccgtt | 900 |
| gacaagtatc tcgagacacc tggggatgag aatgaacatg cccatttcca gaaagccaaa | 960 |
| gagaggcttg aggccaagca ccgagagaga atgtcccagg tcatgagaga atgggaagag | 1020 |
| gcagaacgtc aagcaaagaa cttgcctaaa gctgataaga aggcagttat ccagcatttc | 1080 |
| caggagaaag tggaatcttt ggaacaggaa gcagccaacg agagacagca gctggtggag | 1140 |
| acacacatgg ccagagtgga agccatgctc aatgaccgcc gccgcctggc cctggagaac | 1200 |
| tacatcaccg ctctgcaggc tgttcctcct cggcctcgtc acgtgttcaa tatgctaaag | 1260 |
| aagtatgtcc gcgcagaaca gaaggacaga cagcacaccc taaagcattt cgagcatgtg | 1320 |
| cgcatggtgg atcccaagaa agccgctcag atccggtccc aggttatgac acacctccgt | 1380 |
| gtgatttatg agcgcatgaa tcagtctctc tccctgctct acaacgtgcc tgcagtggcc | 1440 |
| gaggagattc aggatgaagt tgatgagctg cttcagaaag gcaaaacta ttcagatgac | 1500 |
| gtcttggcca acatgattag tgaaccaagg atcagttacg aaacgatgc tctcatgcca | 1560 |
| tctttgaccg aaacgaaaac caccgtggag ctccttcccg tgaatggaga gttcagcctg | 1620 |
| gacgatctcc agccgtggca ttcttttggg gctgactctg tgccagccaa cacagaaaac | 1680 |
| gaagttgagc ctgttgatgc ccgccctgct gccgaccgag actgaccac tcgaccaggt | 1740 |
| tctgggttga caaatatcaa gacggaggag atctctgaag tgaatctgga tgcagaattc | 1800 |
| cgacatgact caggatatga agttcatcat caaaaattgg tgttctttgc agaagatgtg | 1860 |
| ggttcaaaca aaggtgcaat cattggactc atggtgggcg tgttgtcat agcgacagtg | 1920 |
| gtcatcatca ccttggtgat gctgaagaag aaacagtaca catccattca tcatggtgtg | 1980 |
| gtggaggttg acgccgctgt cacccagag gagcgccacc tgtccaatct gcagcagaac | 2040 |
| ggctacgaaa atccaaccta caagttcttt gagcagatgc agaac | 2085 |

```
<210> SEQ ID NO 20
<211> LENGTH: 1404
<212> TYPE: DNA
<213> ORGANISM: Artificial Sequence
<220> FEATURE:
<223> OTHER INFORMATION: PS1 cDNA

<400> SEQUENCE: 20
atgacagagt tacctgcacc gttgtcctac ttccagaatg cacagatgtc tgaggacaac        60
cacctgagca atactgtacg tagccagaat gacaatagag aacggcagga gcacaacgac       120
agacggagcc ttggccaccc tgagccatta tctaatggac gacccaggg taactcccgg       180 caggtggtgg agcaagatga ggaagaagat gaggagctga cattgaaata tggcgccaag       240
catgtgatca tgctctttgt ccctgtgact ctctgcatgg tggtggtcgt ggctaccatt       300
aagtcagtca gcttttatac ccggaaggat gggcagctaa tctataccc attcacagaa       360 gataccgaga ctgtgggcca gagagccctg cactcaattc tgaatgctgc catcatgatc       420
agtgtcattg ttgtcctgac tatcctcctg gtggttctgt ataaatacag gtgctataag       480
gtcatccatg cctggcttat tatatcatct ctattgttgc tgttctttt tcattcatt        540 tacttgggg aagtgtttaa aacctataac gttgctgtgg actacattac tgttgcactc       600
ctgatctgga attttggtgt ggtgggaatg atttccattc actggaaagg tccacttcga       660
ctccagcagg catatctcat tatgattagt gccctcatgg ccctggtgtt tatcaagtac       720
ctccctgaat ggactgcgtg gctcatcttg gctgtgattt cagtatatga tttagtggct       780
gttttgtgtc cgaaaggtcc acttcgtatg ctggttgaaa cagctcagga gagaaatgaa       840
acgctttttc cagctgtcat ttactcctca acaatggtgt ggttggtgaa tatggcagaa       900
ggagacccgg aagctcaaag gagagtatcc aaaaattcca agtataatgc agaaagcaca       960
gaaagggagt cacaagacac tgttgcagag aatgatgatg gcgggttcag tgaggaatgg      1020
gaagcccaga gggacagtca tctagggcct catcgctcta cacctgagtc acgagctgct      1080
gtccaggaac tttccagcag tatcctcgct ggtgaagacc cagaggaaag gggagtaaaa      1140
cttggattgg gagattttcat tttctacagt gttctggttg gtaaagcctc agcaacagcc      1200
agtggagact ggaacacaac catagcctgt ttcgtagcca tattaattgg tttgtgcctt      1260
acattattac tccttgccat tttcaagaaa gcattgccag ctcttccaat ctccatcacc      1320
tttgggcttg ttttctactt tgccacagat tatcttgtac agccttttat ggaccaatta      1380
gcattccatc aatttatat ctag                                             1404
```

PORCINE THY1 GENE PROMOTER SPECIFICALLY EXPRESSED IN NEURONS

RELATED APPLICATIONS

This application is a Division of U.S. patent application Ser. No. 15/735,185 filed on Dec. 10, 2017, which is a National Phase of PCT Patent Application No. PCT/KR2017/003750 having International filing date of Apr. 6, 2017, which claims the benefit of priority of Korean Patent Application No. 10-2016-0067517 filed on May 31, 2016. The contents of the above applications are all incorporated by reference as if fully set forth herein in their entirety.

SEQUENCE LISTING STATEMENT

The ASCII file, entitled 89076SequenceListing.txt, created on Aug. 11, 2021, comprising 52,387 bytes, submitted concurrently with the filing of this application is incorporated herein by reference. The sequence listing submitted herewith is identical to the sequence listing forming part of the international application.

FIELD AND BACKGROUND OF THE INVENTION

The following description relates to a neuronal-specific expression porcine Thy1 gene promotor.

Using animal models to find new therapies for brain diseases is an essential element in finding new therapeutic targets and performing drug testing at preclinical stages. Studies of these animal models may play an important role in accurately detecting abnormal brain cell spatio-temporal change processes and brain dysfunction mechanisms, and verifying the effectiveness of various new therapeutic targets and new therapies. Until now, most of the disease models for drug therapy or mechanism studies of degenerative brain diseases have been mostly using rodents, but the pathological patterns and symptoms of animal disease models are much different from those observed in humans. Thus, there have been many problems in a case where clinical trials are performed based on results from rodent disease models. Accordingly, it has become very important to make disease models that may be used in research for pathological mechanism and treatment of various diseases using animals having a high similarity to humans. However, since primates are so scarce that it is difficult and costly to manage the breeding, they may be used for disease research only in extremely limited fields. Therefore, attempts have been continuously made to utilize pigs that may conduct more accurate disease research as new model animals at relatively low cost and facilities.

When it is intended to produce pigs as brain disease models, it is very important that the gene related to brain diseases is specifically expressed in the pig brain or nerve. It is a promoter that regulates such tissue-specific expression. The promoter is a genomic region linked to the upper side of a structural gene, and plays a role of regulating transcription of the structural gene linked to mRNA. Promoters are activated by the binding of several common transcription factors, and they have a base sequence such as TATA box and CAT box, etc. that regulate gene expression in general. Since the proteins required for basic metabolism in a living body must maintain a constant concentration in the cells, the promoter linked to these genes is always activated by the action of common transcription factors alone. On the contrary, proteins that do not have a role in normal times and function only under specific circumstances are linked to an inducible promoter which induces the expression of the corresponding structural gene. Inducible promoters are activated by the binding of specific transcription factors activated by external stimuli that come from environmental factors from the surroundings during the development of an organism. That is, when a model pig for a brain disease is prepared, a gene expression system may work well if a disease-related gene is introduced together with a promoter capable of inducing specific expression in a porcine brain or nerve cell.

SUMMARY OF INVENTION

Example embodiments provide a Thy1 gene promoter specifically expressed in neurons and a recombinant vector including the same.

Example embodiments provide a transformed cell line using a Thy1 gene promoter specifically expressed in neurons and a recombinant vector including the same.

However, the subject matters to be solved by the disclosure are not limited to the above-mentioned subject matters, and the other subject matters that are not mentioned may be clearly understood by those skilled in the art from the following descriptions.

According to an example embodiment, there is provided a Thy1 gene promoter specifically expressed in neurons, including the base sequence of SEQ ID NO: 1.

According to an example embodiment, there is provided a Thy1 gene promoter specifically expressed in neurons, including the base sequence of SEQ ID NO: 4.

According to one aspect, the promoter may include a binding site of a PBX and a CREB transcription factor.

According to an example embodiment, there is provided a primer set including the sequence of SEQ ID NO: 2 and SEQ ID NO: 3 and for amplifying the promoter of claim 1.

According to an example embodiment, there is provided a primer set including the sequence of SEQ ID NO: 5 and SEQ ID NO: 6 and for amplifying the promoter of claim 2.

According to an example embodiment, there is provided a recombinant expression vector including a Thy1 gene promoter having the base sequence of SEQ ID NO: 1 or SEQ ID NO: 4 and a gene related to Alzheimer's disease.

According to one aspect, the Alzheimer's disease-related gene may be an APP mutant gene, a Tau mutant gene, or a PS1 mutant gene.

According to an example embodiment, there is provided a somatic cell of a mammal transformed by introducing the recombinant expression vector.

According to an example embodiment, there is provided a mammalian embryo in which the recombinant expression vector is injected.

According to an example embodiment, there is provided a transgenic mammal obtained by implanting the embryo in a uterus of a surrogate mother.

According to an example embodiment, there is provided a method of preparing a recombinant expression vector, in which the method includes: constructing a first vector including a restriction enzyme site and removing the promoter and gene cluster; preparing a recombinant second vector by inserting the promoter, APP gene, PS1 gene. Tau gene and the promoter of claim 1 into a second vector, respectively; inducing a mutation in each of APP gene. PS1 gene and Tau gene on the recombinant second vector; and inserting the recombinant second vector into the first vector.

According to an example embodiment, there is provided a method of preparing a transgenic pig, in which the method includes: preparing the recombinant expression vector; separating somatic cells from the pig; introducing the expression vector into the somatic cells; selecting and culturing clone somatic cells into which the expression vector is introduced; removing the nucleus of the oocyte harvested from a surrogate mother and fusing the cloned somatic cells; and transplanting the fused clone into a surrogate mother.

According to example embodiments, a promoter specifically expressed in neurons is derived from a pig, and has high activity in brain cells or neurons, and thus may be used for controlling the expression of a target gene. In particular, as compared with rodent mice, pigs are highly similar to human genes and have many similarities in terms of metabolism. Therefore, pigs may be transformed into recombinant vectors and used as disease models, so that the promoter may also be utilized in the preparation of such disease models.

BRIEF DESCRIPTION OF THE SEVERAL VIEWS OF THE DRAWINGS

FIG. 5 illustrates a primer for preparing a luciferase reporter vector.

DESCRIPTION OF SPECIFIC EMBODIMENTS OF THE INVENTION

Figure 1:
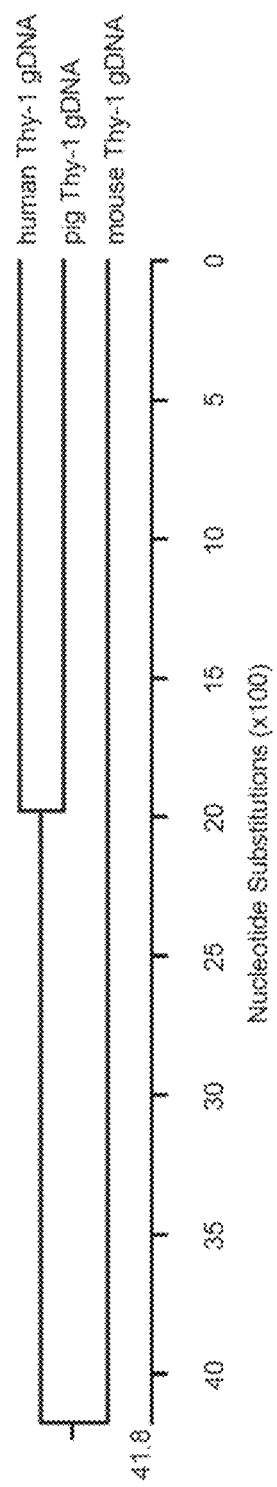
FIG. 1 illustrates the phylogenetic similarity of the Thy-1 gene through the ClustalV method.

The following detailed description is provided in order to explain the example embodiments by referring to the figures.

Various modifications may be made to example embodiments. However, it should be understood that these embodiments are not construed as limited to the illustrated forms and include all changes, equivalents or alternatives within the idea and the technical scope of this disclosure.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in describing of example embodiments, detailed description of well-known related structures or functions will be omitted when it is deemed that such description will cause ambiguous interpretation of the present disclosure.

The term "recombinant" refers to a cell in which a cell replicates a heterologous nucleic acid, expresses the nucleic acid, or expresses a protein encoded by a peptide, a heterologous peptide or a heterologous nucleic acid. Recombinant cells may express genes or gene segments that are not found in the native form of the cells, either in sense or antisense form. In addition, recombinant cells may express a gene found in a cell in a natural state, but the gene has been reintroduced intracellularly by artificial means as modified.

The term "vector" is used to refer to a DNA fragment (s), nucleic acid molecule, which is delivered into a cell. The vector replicates the DNA and may be independently regenerated in the host cell. The term "carrier" is often used interchangeably with "vector." The term "expression vector" means a recombinant DNA molecule including a desired coding sequence and a suitable nucleic acid sequence necessary for expressing a coding sequence operably linked in a particular host organism. Promoters, enhancers, termination signals and polyadenylation signals available in eukaryotic cells are known.

The mouse Thy1 promoter, which has been conventionally used mainly, has a remarkably low similarity of the Thy1 promoter of the pigs or humans, whereas the Thy1 promoter of the pig and the human Thy1 promoter are very similar to each other (see Example 1). For example, in producing a pig model of a brain disease or neurological disease, it is very important to produce a promoter capable of ensuring specific expression of brain cells or neurons, and in particular, a promoter fragment with high activity having the size that may be used for a recombinant expression vector is essential.

According to an example embodiment, there is provided a Thy1 gene promoter that specifically expresses in a neuron, including the base sequence of SEQ ID NO: 1. The base sequence of SEQ ID NO: 1 has a size of 500 bp, but any base sequence including the same may be used without limitation. Preferably, a promoter having a base sequence of a size of 500 bp to 2579 bp may be used. In an example embodiment, SEQ ID NO: 4 exhibits the base sequence of a promoter having a size of 2579 bp at positions −4858 to −2279. With reference to SEQ ID NO: 1 and SEQ ID NO: 4, a promoter having a base sequence ranging from 500 bp to 2579 bp may be used.

Also, the variome of the promoter sequence is included within the scope of the disclosure. The variome is a base sequence having a functional characteristic similar to that of the base sequence of SEQ ID NO: 1 although the base sequence thereof is changed. Specifically, the promoter may include a base sequence having 70% or more, 80% or more, 90% or more, or 95% or more of sequence homology with the base sequence of SEQ ID NO: 1, respectively. "% of sequence homology" to polynucleotides is determined by comparing the comparison region with two optimally aligned sequences, and a portion of the polynucleotide sequence in the comparison region may be added or deleted (i.e., gap), as compared to the reference sequence (which does not include an addition or deletion).

According to one aspect, the promoter may include a binding site of a PBX and a CREB transcription factor. The PBX and CREB transcription factors are transcription factors known to be associated with brain diseases.

According to an example embodiment, there is provided a primer set consisting of the sequences of SEQ ID NO: 2 and SEQ ID NO: 3 and for amplifying the promoter of claim 1.

In addition, according to one aspect, there is provided a primer set consisting of the sequences of SEQ ID NO: 5 and SEQ ID NO: 6 and for amplifying the promoter of SEQ ID NO: 4.

According to an example embodiment, there is provided a recombinant expression vector including a Thy1 gene promoter having a base sequence of SEQ ID NO: 1 and an Alzheimer-related gene.

According to one aspect of the disclosure, the expression vector may be used without limitation as long as it may be used to efficiently induce the expression of the Alzheimer-related protein specifically in the neuron. Preferably, however, the retroviral vector may be used. For example, pTet-CKOS may be used. In addition, the expression vector may further include an enhancer to further improve the expression of the gene, for example, a CMV (cytomegalo virus) enhancer.

According to one aspect, the Alzheimer's disease-related gene may be an APP mutant gene, a Tau mutant gene, or a PS1 mutant gene. It is known that APP, Tau, and PS1, which are known to be typical genes causing Alzheimer's disease, contribute to overexpression of β-amyloid, which is a pathogenesis of Alzheimer's disease, and aggregation of Tau protein. β-amyloid is produced from amyloid precursor protein (APP) through a proteolysis process. APP, which is a precursor protein, is a protein with a transmembrane domain and is expressed in several isotypes by alternative splicing and is known to undergo two metabolic pathways within the cell. Mutations in this APP protein are found in patients with familial Alzheimer's disease. The mutations discovered so far include APP670/671 (Swedish). APP672 (Flemish). APP716 (Florida), APP717 (London), and these mutations have been shown to increase the formation of β-amyloid. Another gene that shows a mutation that causes familial Alzheimer's disease is presenilin 1 (PS1). PS1 is a protein with eight transmembrane domains and plays an important role in a process of generation and is known to act as a member of γ-secretase itself or a complex. PS1 has been reported to have 45 mutations or more that cause familial Alzheimer's disease throughout the protein, and these mutations have also been shown to increase the amount of β-amyloid formation. It is known that the onset of Alzheimer's disease caused by the generated β-amyloid is accompanied by a process of neuronal damage by hyperphosphorylation of Tau protein, and several phosphorylases are involved in hyperphosphorylation of such Tau protein. In addition to hyperphosphorylation of Tau, tangle formation of Tau has also been shown to play a role in neuronal damage and a mutation of Tau in which the tangle is well formed has been found.

The recombinant expression vector may further include a 2A sequence between the APP mutant gene, the Tau mutant gene and the PS1 mutant gene, respectively. In an example embodiment, a 2A sequence is further included between the APP mutant gene and the tau mutant gene, and a 2A gene may be further included between the tau mutant gene and the PS1 mutant gene.

The 2A gene sequence encodes 18 to 22 amino acids, and among them, the four amino acids Asparagine (N), Proline (P), Glycine (G) and Proline (P) located at the terminal are important amino acids conserved between the species. Such sequences tend to self-cleavage when synthesized into peptides. Due to this property, when a ribosome reaches a genetic code that encodes N, P, G located at the 2A sequence terminal when protein transcription proceeds. NPG is sequentially recognized to make a peptide bond, and then instead of bringing a prolyl-tRNA with Proline linked to the amino acid proline encoding code, it brings a releasing factor (RF). After the binding of the RF factors, the previously formed peptides are no longer able to bind peptide and are released from ribosomes. After the 2A sequence, the encoded code works normally and the next protein transcription proceeds. In conclusion, by inserting the 2A sequence, many genes may be expressed using one promoter. The recombinant expression vector of the disclosure may simultaneously express these genes by inserting these 2A sequences into each of the three genes.

The APP mutant gene may be one in which amino acid 595, amino acid 596, or both of them are mutated, and in which amino acid 641, amino acid 642 or both of them are mutated. In an exemplary embodiment, the APP mutant gene is a gene in which the 595 is mutated to Asn, the 596 amino acid is mutated to Lys, the 641 amino acid is mutated to Val and the 642 amino acid is mutated to Ile. In one embodiment, the mutant APP gene is as set forth in SEQ ID NO: 19. The TAU mutant gene may be one in which amino acid 243 is mutated. In addition, the PS1 mutant gene may be one in which amino acid 146, amino acid 286, or both of them are mutated. The PS1 mutant gene may also be a gene in which the 146 amino acid Met is mutated to Leu and the 286 amino acid Pro is mutated to Leu. In one embodiment, the PS1 mutant is encoded by the nucleic acid sequence of SEQ ID NO: 20.

According to an example embodiment, there is provided a somatic cell of a mammal transformed by introducing the recombinant expression vector. The cell may be used without limitation except for humans if it originates from a mammal. However, in the case of a mouse, which is mainly used conventionally, metabolism is very fast, and since the lifetime change is very different from that of the humans, it is difficult to use it as an accurate disease model. Therefore, an animal having a size similar to a human body and having a similar shape in terms of metabolism is preferable, and a pig is most preferable among them. According to an example embodiment, there is provided a mammalian embryo in which the recombinant expression vector is injected. According to an example embodiment, there is provided a transgenic mammal obtained by implanting the embryo in a uterus of a surrogate mother.

According to an example embodiment, there is provided a method of preparing a recombinant expression vector, in which the method includes: constructing a first vector including a restriction enzyme site and removing a promoter and gene cluster, preparing a recombinant second vector by inserting the promoter, APP gene, PS1 gene and Tau gene of claim 1 into a second vector, respectively; inducing a mutation in each of APP gene, PS1 gene and Tau gene on the recombinant second vector; and inserting the recombinant second vector into the first vector.

According to an example embodiment, there is provided a method of preparing a transgenic pig, in which the method includes: preparing the recombinant expression vector; separating somatic cells from the pig; introducing the expression vector into the somatic cells; selecting and culturing clone somatic cells into which the expression vector is introduced; removing the nucleus of the oocyte harvested from a surrogate mother and fusing the cloned somatic cells; and transplanting the fused clone into a surrogate mother.

Hereinafter, the disclosure will be described in more detail with reference to examples. The following examples are given for the purpose of illustrating the disclosure, and the scope of the present disclosure is not limited thereto.

Example 1: Investigation of Thy1 Gene Similarity Between Humans, Mice and Pigs Using Phylogenetic Analysis and zPicture Analysis In order to analyze the sequences of Thy1 genes, the global genes of the humans (GeneID: 7070), mouse (GeneID: 21838), pigs (GeneID: 100109488) and the promoter (about 2.2 to 2.6 kb forward from the first exon) DNA sequence were downloaded from National Center for Biotechnology Information (NCBI). The phylogenetic similarity of each DNA sequence was investigated using DNASTAR Lasergene Megalign software. The Align method was used as the Clustal V method.

FIG. 1 illustrates the phylogenetic similarity of the Thy-1 gene through the ClustalV method.

Referring to FIG. 1, it may be understood that the Thy1 gene of humans and pigs is located very close compared to the Thy 1 gene of a mouse.

The similarity of the Thy1 gene in human-to-pig or pig-to-mouse was compared with each other in order to investigate the similarity of the interspecific genes of Thy1 and determine the promoter range and the candidate sequence of porcine Thy1 by locating promoters with high similarity. The comparison tool was a zPicture analysis tool based on a pairwise sequence aligner. The Thy1 gene in humans, pigs, and mice consists of four exons, and the ATG codon that initiates protein expression is located in the second exon. A of ATG is named as +1 position. The nucleotide located at the front is named as "− number" and the back of A is named as "+ number". In humans, the gene sequence that regulates the expression of Thy1 gene specifically in brain tissue is important from the front of the first exon to the front of the second exon (−3463 to −1).

Figure 2:
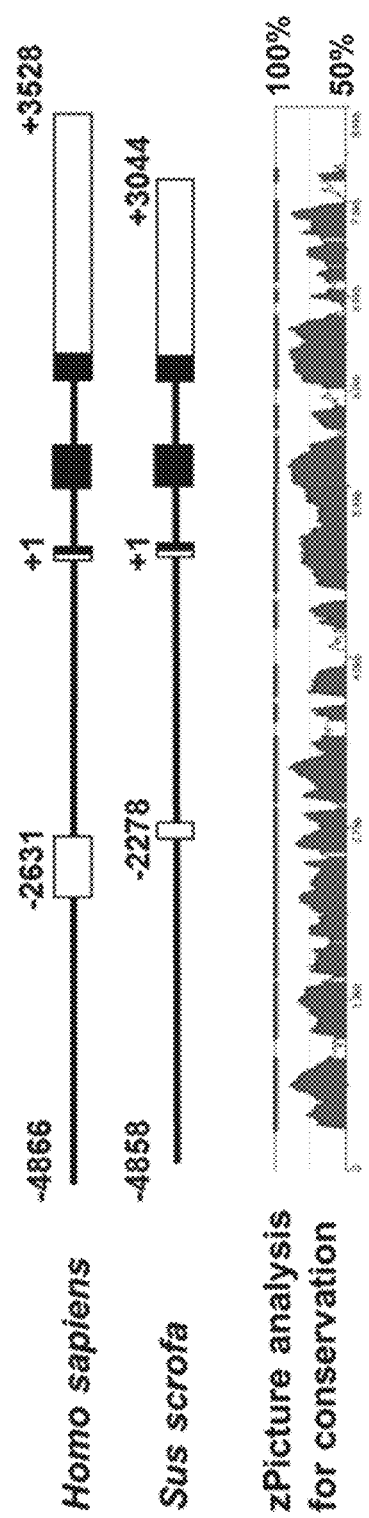
FIG. 2 is an analysis of the Thy-1 gene similarity between humans and pigs using zPicture.
Figure 3:
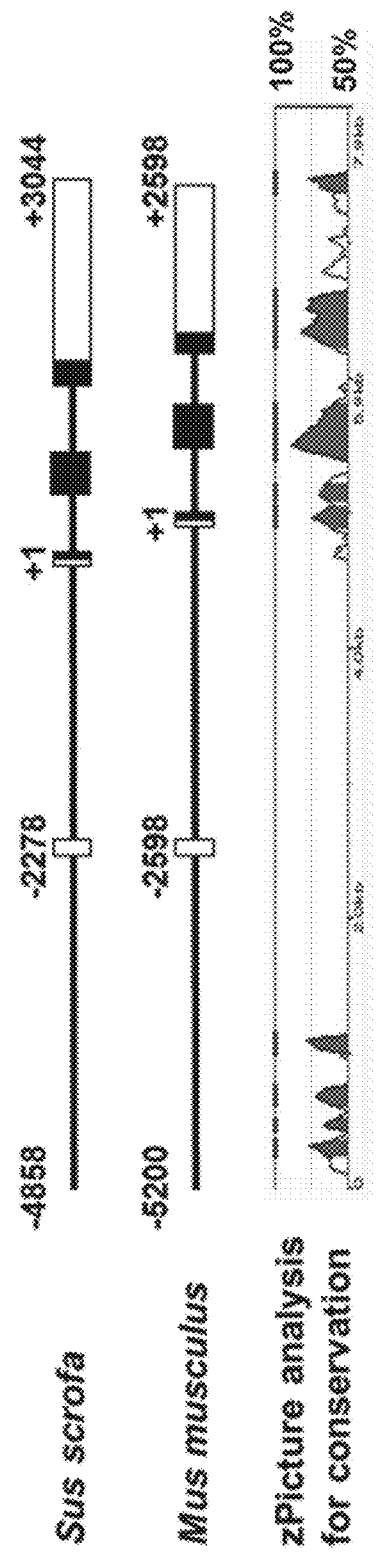
FIG. 3 is an analysis of the Thy-1 gene similarity between pigs and mice using zPicture.

FIG. 2 is an analysis of the Thy-1 gene similarity between humans and pigs using zPicture. FIG. 3 is an analysis of Thy-1 gene similarity between pigs and mice using zPicture.

Referring to FIG. 2, when the Thy1 gene similarity between pigs and humans is analyzed, the DNA sequence similarity is high in front of the first exon and the first intro sequence is less similar. On the other hand, referring to FIG. 3, when DNA sequences of pigs and mice are compared, except for the coding sequence expressing the protein and the front of the first exon, the overall DNA sequence similarity is poor. That is, the similarity of the Thy1 gene in pigs and humans is very high. Among them, the gene sequence located at −4858 to −2278 of Thy1 is highly likely to be involved in the regulation of Thy1 expression.

Example 2: List of Predicted Transcriptional Regulatory Factors Binding to a Human and Porcine Thy1 Gene Promoter rVista 2.0 was used as an analytical tool to investigate the predicted transcriptional regulatory factors binding to the human and porcine Thy1 gene promoters.

Table 1 below shows the transcriptional regulatory factors binding to the Thy1 gene promoter.

TABLE 1

| −4858 to −3858 | −3858 to −2858 | −2858 to −1858 |
|---|---|---|
| SMAD4 | NKX25B | EGR2 |
| MAZR | TBX5 | EGR3 |
| SP1 | ARP1 | SRF |
| MAZ | CDP | LRF |
| RORA | CLOX | NFY |
| HTF | PBX | CAAT |
| ER | NFY | ZIC3 |
| XBP1 | AREB6 | CHCH |
| RUSH1 | AP2A | MTF |
| LFA1 | AP2G | ETF |
| ELK1 | CREB | |
| TEF1 | HNF4 | |
| RBPJK | SZF11 | |
| | STAF | |
| | E2F1 | |
| | HSF1 | |
| | HSF2 | |
| | SMAD4 | |
| | EGR1 | |

Figure 4:
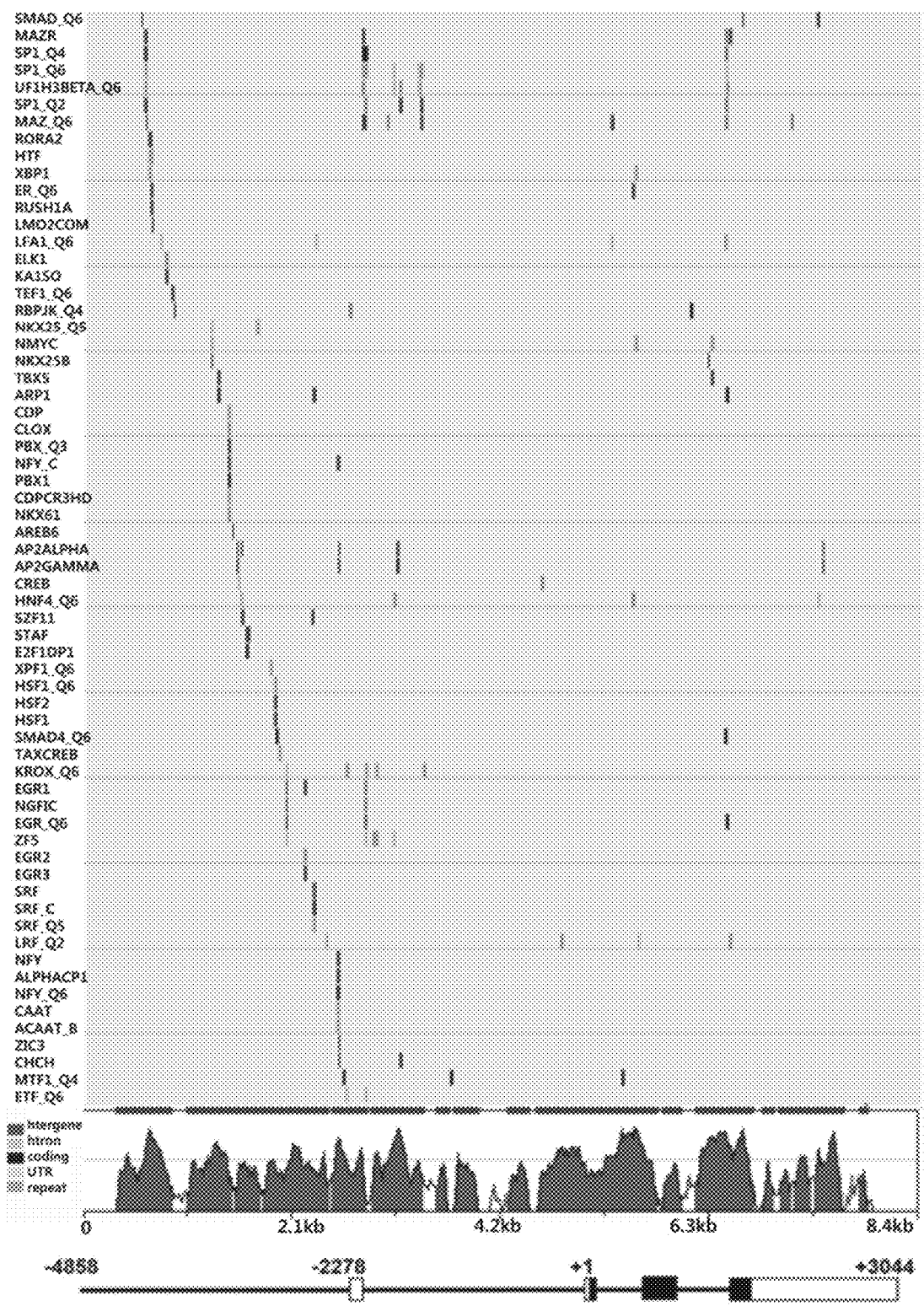
FIG. 4 illustrates the location of a transcriptional regulator binding to the Thy1 gene promoter.

FIG. 4 illustrates the location of the transcriptional regulatory factors binding to the Thy1 gene promoter.

Referring to Table 1 and FIG. 4, there exists a DNA sequence capable of binding transcriptional regulator factors such as TBX5, PBX, CREB, AREB6, AP2, EMF, HSF1, SMAD4, EGR1, EGR2, EGR3, etc. in about 1 kb upstream toward the front of the first exon of the porcine Thy1 gene. Among them, in particular. PBX and CREB transcriptional regulatory factors are known to be related to brain diseases.

Therefore, the promoter region of the porcine Thy1 of −3858 to −2858, particularly −3380 to −2880, is important for the expression of brain tissue-specific Thy1.

Example 3: Analysis of Luciferase Reporter Vector and Luciferase for Measuring the Activity of Porcine Thy1 Promoter Based on the analysis of Examples 1 and 2, a luciferase reporter vector was produced to find the Thy1 promoter DNA sequence of a pig inducing tissue-specific expression in actual cells. The primers were designed to make the −4858/−2279_Luc vector in which the Thy1 gene −4858 to −2279 was inserted in front of the luciferase cDNA and the −2578/−40_Luc vector in which −2578 to −40 was inserted.

SEQ ID NO: 7 exhibits the base sequence (2579 bp) of the Thy1 promoter −4858 to −2279 location and SEQ ID NO: 8 exhibits the base sequence (2538 bp) of the Thy1 promoter −2578 to −40 location.

FIG. 5 illustrates a primer for producing a luciferase reporter vector.

After isolating the chromosomes from the pigs, a Thy1 promoter DNA having a base sequence of −4858 to −2279 and a base sequence of −2578 to −40 was synthesized by PCR using a pig chromosome as a template using the above primer, and TA was cloned in a pTOP TA V2 vector. The synthesized DNA sequence was confirmed to be accurately synthesized by sequencing.

Figure 6A:
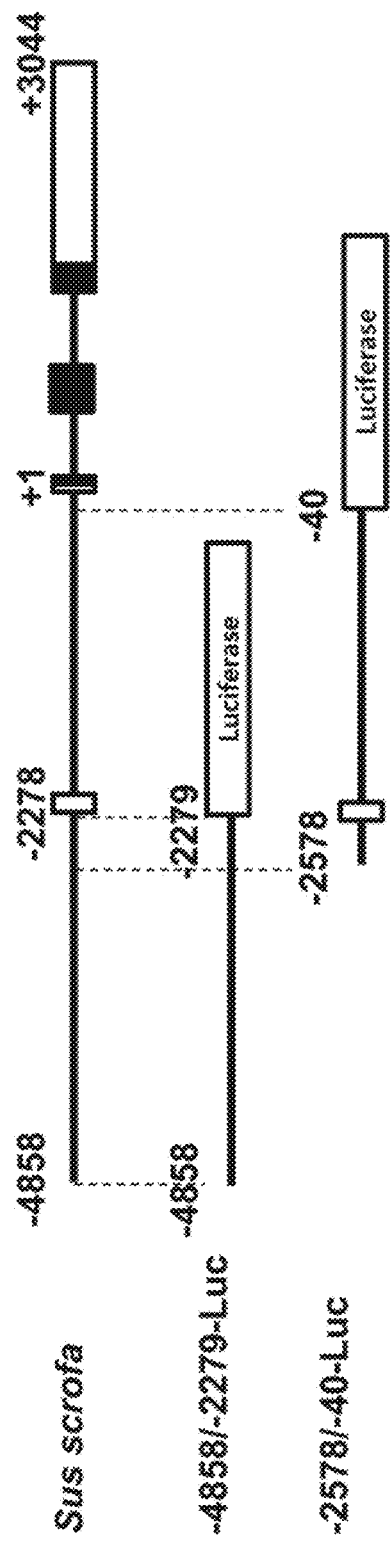
FIG. 6A illustrates a location of a Thy1 promoter DNA inserted into the luciferase reporter vector.

Referring to FIG. 6A, the location of the Thy1 promoter DNA inserted into the luciferase reporter vector may be roughly known. Each Thy1 promoter was cut from pTOP and inserted into the pGL4.10 [luc2] vector using the SacI/NheI restriction enzyme to clone the −4858/−2279_Luc vector and the KpnI/XhoI restriction enzyme to the −2578/−40_Luc vector. SEQ ID NO: 9 exhibits the base sequence (4242 bp) of the pGL4.10 [luc2] vector.

Figure 6B:
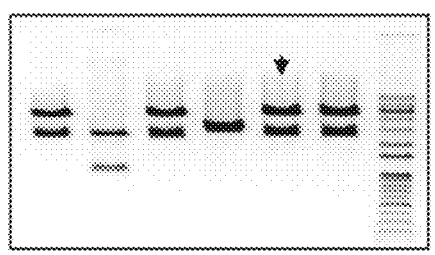
FIG. 6B is a schematic diagram of a luciferase reporter vector for measuring the activity of the Thy1 promoter.
Figure 6B:
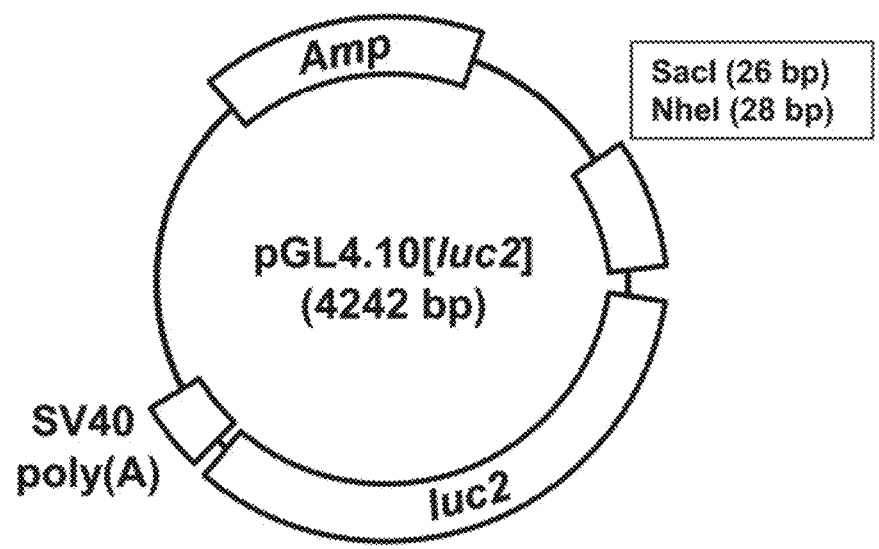
Figure 6C:
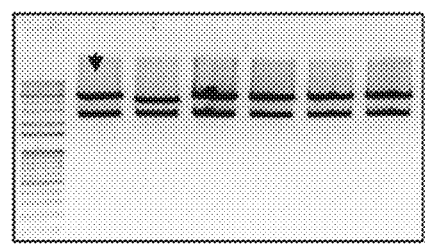
FIG. 6C is a schematic diagram of a luciferase reporter vector for measuring the activity of the Thy1 promoter.
Figure 6C:
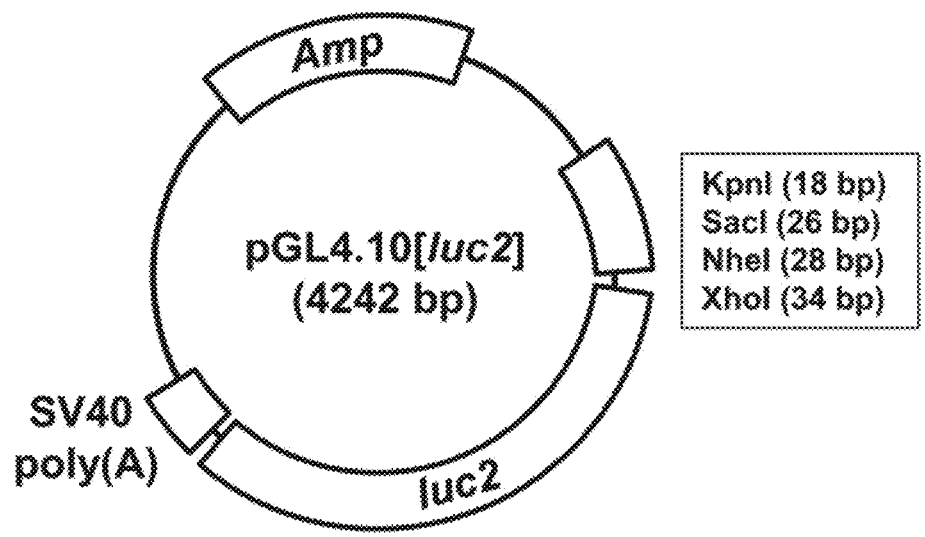

FIGS. 6B and 6C are schematic diagrams illustrating each respective vector and used restriction enzymes.

A luciferase assay was performed to investigate whether the two synthesized Thy1 promoters exhibited actual neuronal-specific expression patterns. 500 ng of −4858/−2279_Luc or −2578/−40_Luc vectors were transfected with 50 ng of pRL-TK vector using Lipofectamine 2000 in representative neuronal cell lines SH-SY5Y and PC12. As a control group, 500 ng of the basic pGL4.10 [luc2] was transfected. In addition, 293T cells were used as a negative control group cell line for neurons to investigate the activity of the promoter.

Figure 7:
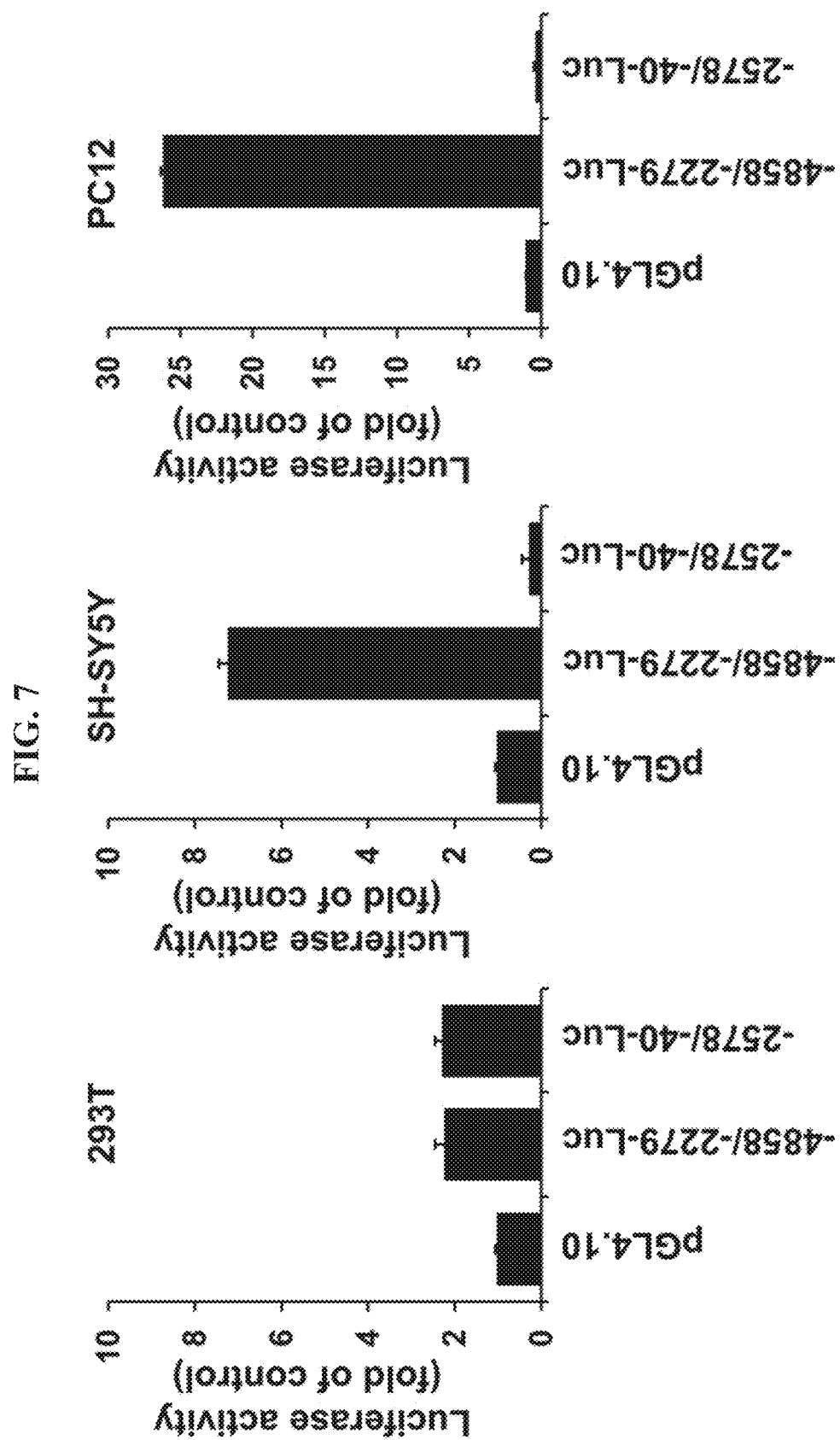
FIG. 7 is a graph illustrating brain cell-specific activity of the Thy1 promoter of pigs measured by luciferase assay.

FIG. 7 is a graph illustrating brain cell-specific activity of the Thy1 promoter of pigs measured by luciferase assay.

Referring to FIG. 7, the activity of the two Thy1 promoters was low in the non-neuronal 293T cell, whereas the promoter activity of −4858/−2279_Luc in the SH-SY5Y and PC12 neuronal cell lines was very high. In the case of −2578/−40_Luc, the promoter activity is not specifically observed in the neuronal cell line. Therefore, the DNA sequence present in the −4858 to −2279 site of the Thy1 promoter is important for neuron-specific Thy1 expression.

Example 4: Fluorescence Reporter Vector and Fluorescence Analysis for Measuring the Activity of Thy1 Promoter of Intracellular Porcine In order to measure the activity of Thy1 promoter through image analysis, EGFP expression vector and DsRed2 expression vector under transcriptional regulation of Thy1 promoter −4858/−2279 were prepared.

Figure 8A:
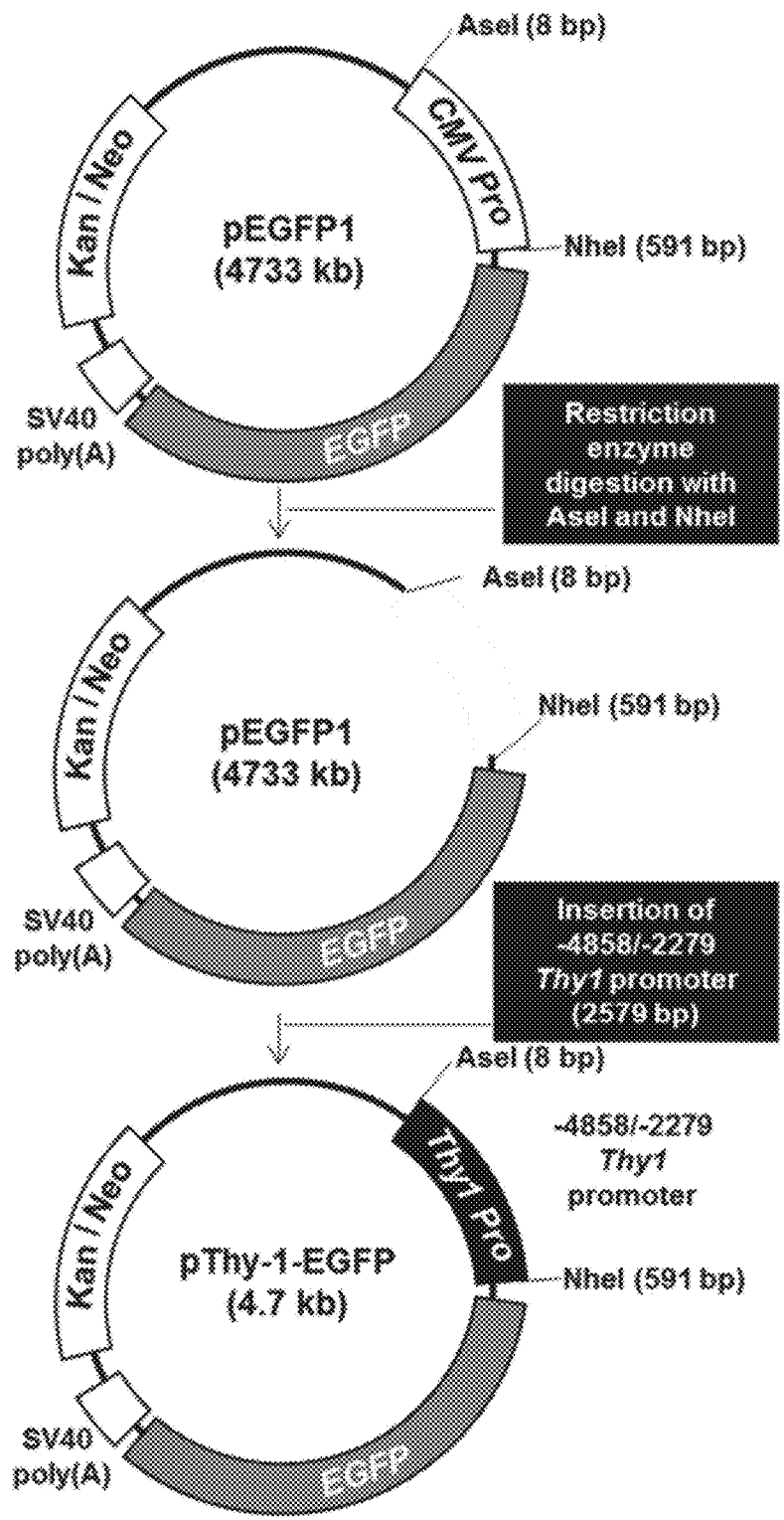
FIG. 8A is a schematic diagram of a reporter vector (pThy1-EGFP vector) for measuring the activity of the Thy1 promoter.
Figure 8B:
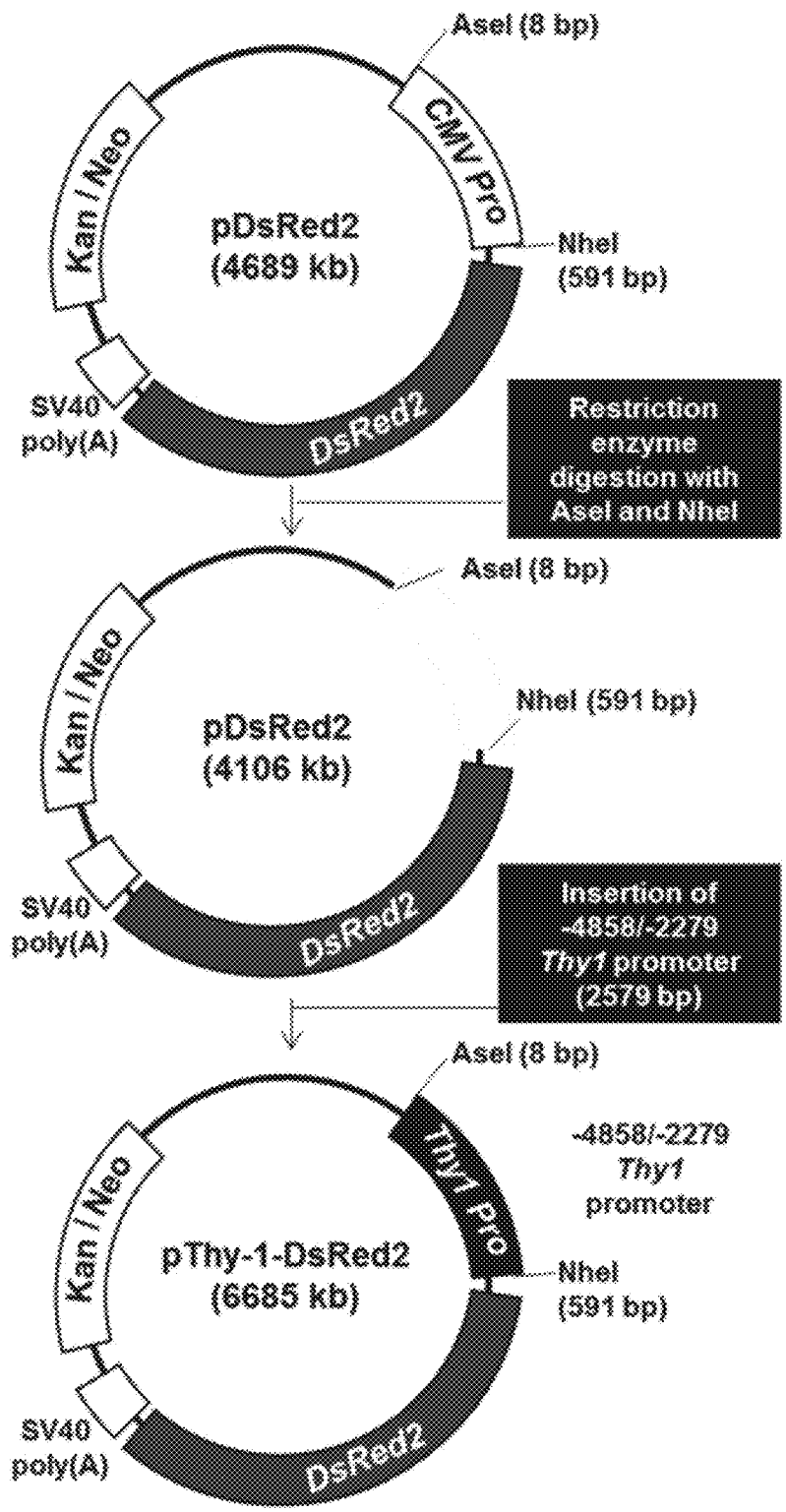
FIG. 8B is a schematic diagram of a reporter vector (pThy1-EGFP vector) for measuring the activity of the Thy1 promoter.

FIGS. 8A and 8B are schematic diagrams of a reporter vector for measuring the activity of the Thy1 promoter.

Referring to FIG. 8, a Thy1 promoter of −4858 to −2279 was synthesized by plasmid PCR using −4858/−2279_Luc as a template. The CMV promoter of pEGFP1 and pDsRed2 was removed with AseI and NheI restriction enzyme, and then the pThy1-EGFP vector (FIG. 8A) and the pThy1-DsRed2 vector (FIG. 8B) were prepared by inserting the Thy1 promoter of −4858 to −2279.

SEQ ID NO: 10 exhibits the base sequence (4733 bp) of the pThy1-EGFP vector and SEQ ID NO: 11 exhibits the base sequence (4689 bp) of the pThy1-DsRed2 vector.

The primers used for preparing the EGFP expression vector and the DsRed2 expression vector are as follows.

```
F:
                                    (SEQ ID NO: 13)
5'-(Ase I) ATTAAT TCTAGATGGGGCAACTGGAG-3'

R:
                                    (SEQ ID NO: 14)
5'-(Nhe I) GCTAGC GGCCAATCAGAGGCTGAG-3'
```

In 293T cells, each vector was transfected with pEGFP1, pThy1-EGFP, pDsRed2, and pThy1-DsRed2, respectively, using Lipofectamin 2000 and observed with fluorescence microscope two days later.

Figure 9:
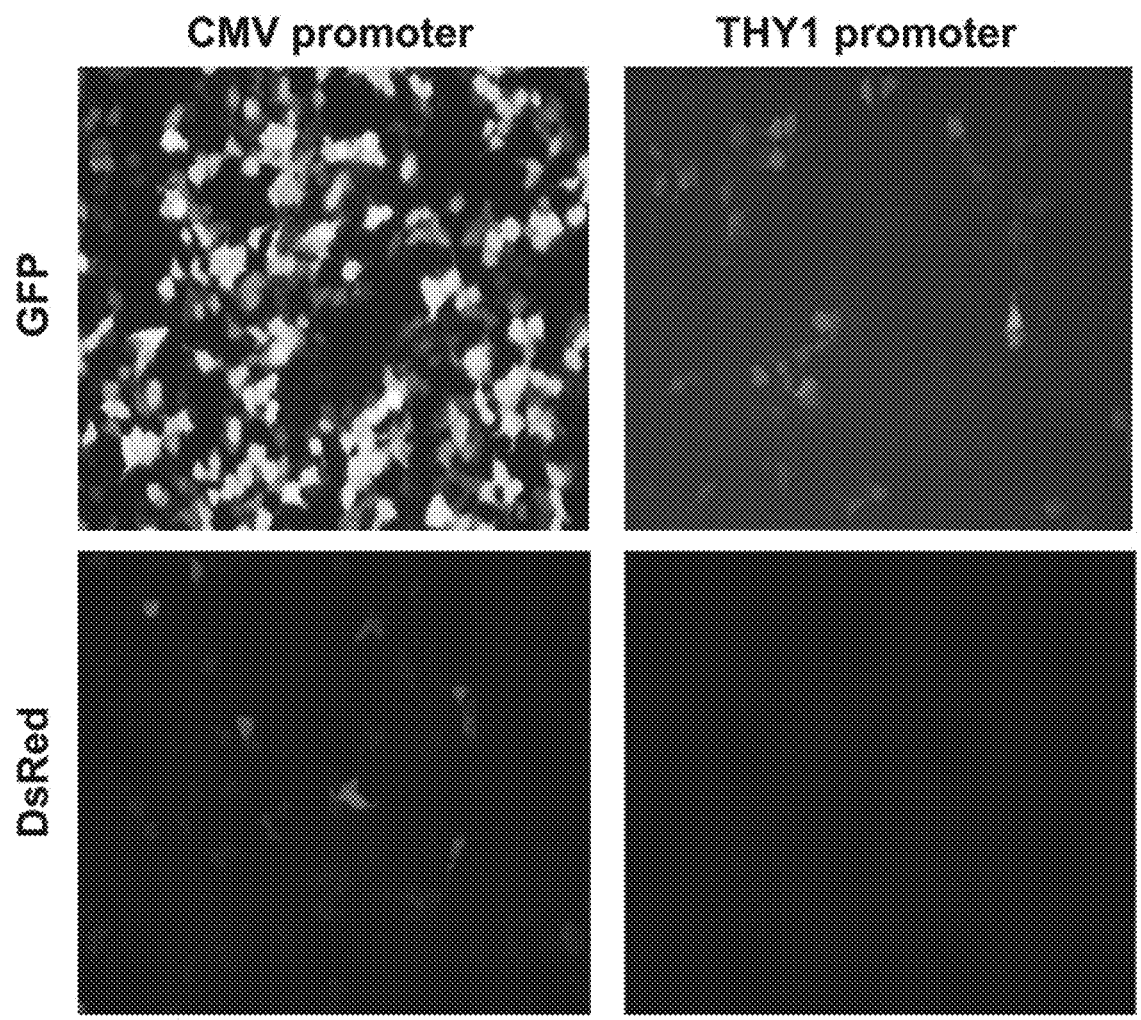
FIG. 9 is a fluorescence microscope photograph illustrating the intracellular Thy1 promoter and CMV promoter activity.

FIG. 9 is a fluorescence microscope photograph illustrating the intracellular Thy1 promoter and CMV promoter activity.

Referring to FIG. 9, the expression of GFP and DsRed proteins under the control of the CMV promoter was very high in 293T cells, whereas the expression of GFP and DsRed proteins under the influence of the Thy1 promoter was relatively low. This is because 293T cells, which are a lack of Thy1 expression, lack a transcriptional regulatory factor to activate the Thy1 promoter.

Example 5: FACS Analysis of the Degree of Thy1 Expression Existing in Various Cells In order to observe the degree of the Thy1 protein basically expressing in 293T embryonic kidney cells. NIH3T3 fibroblasts, and PC12 neuronal cell lines, the cultured cells were treated with 0.25% trypsin-EDTA and removed with a single cell. Then, the primary antibody against Thy1 (produced in mice) was reacted in the cells. FITC-conjugated anti-mouse antibody was reacted and flow cytometry analysis was performed.

Figure 10A:
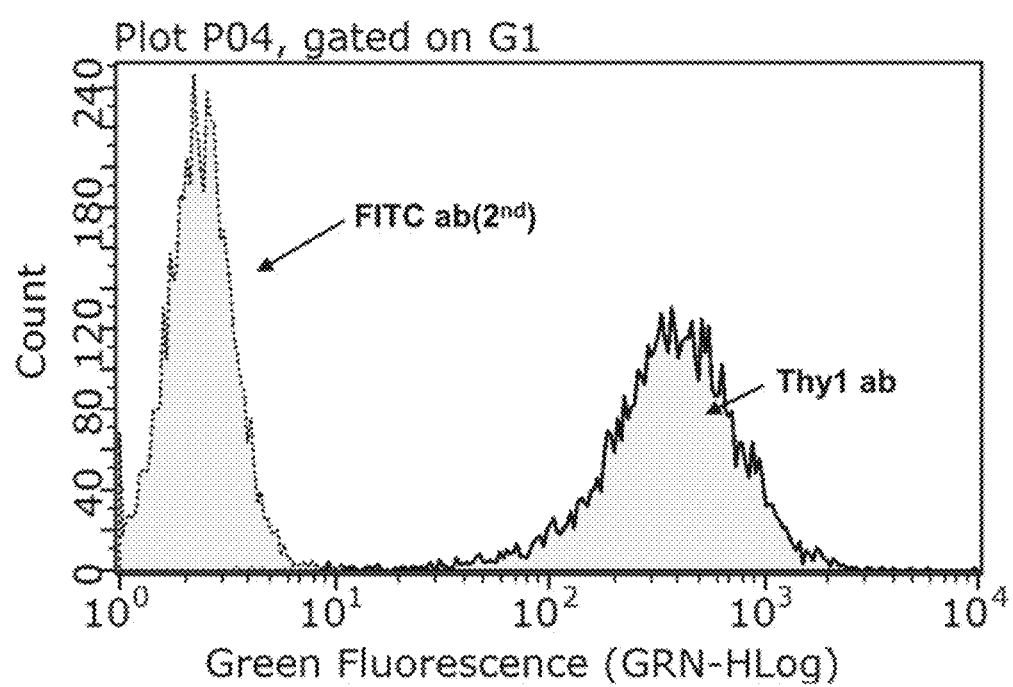
FIG. 10A is a graph illustrating the degree of Thy1 expression in the PC12 neuron cell line.
Figure 10B:
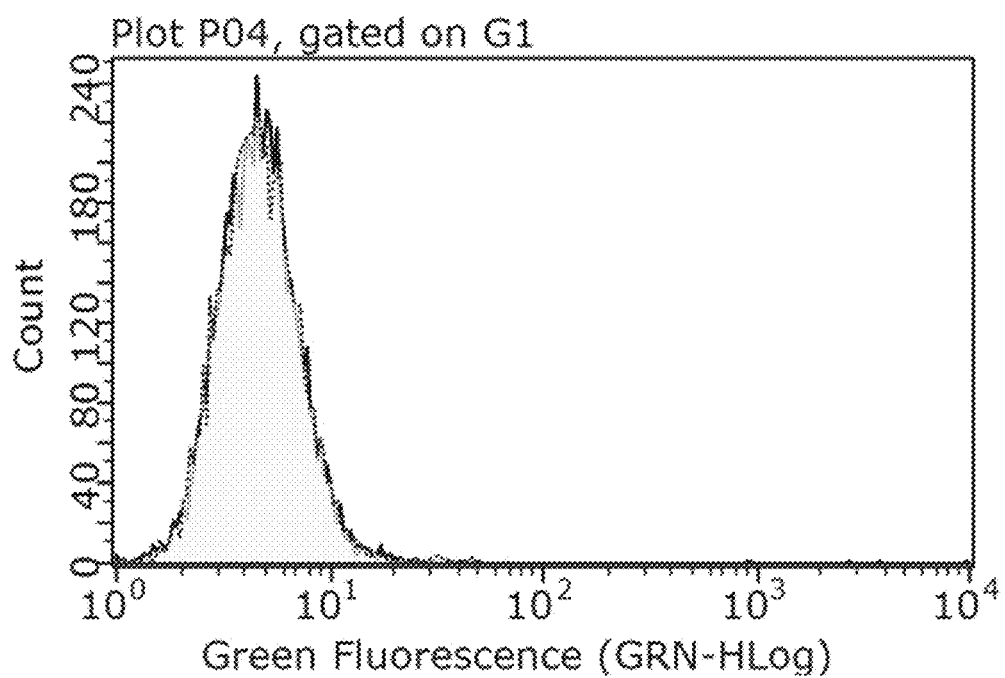
FIG. 10B is a graph illustrating the degree of Thy1 expression in NIH3T3 fibroblast.

FIG. 10A is a graph illustrating the degree of Thy1 expression in the PC12 neuronal cell lines. FIG. 10B is a graph illustrating the degree of Thy1 expression in NIH3T3 fibroblast, and FIG. 10C is a graph illustrating the degree of Thy1 expression in 293T embryonic kidney cells.

Figure 10C:
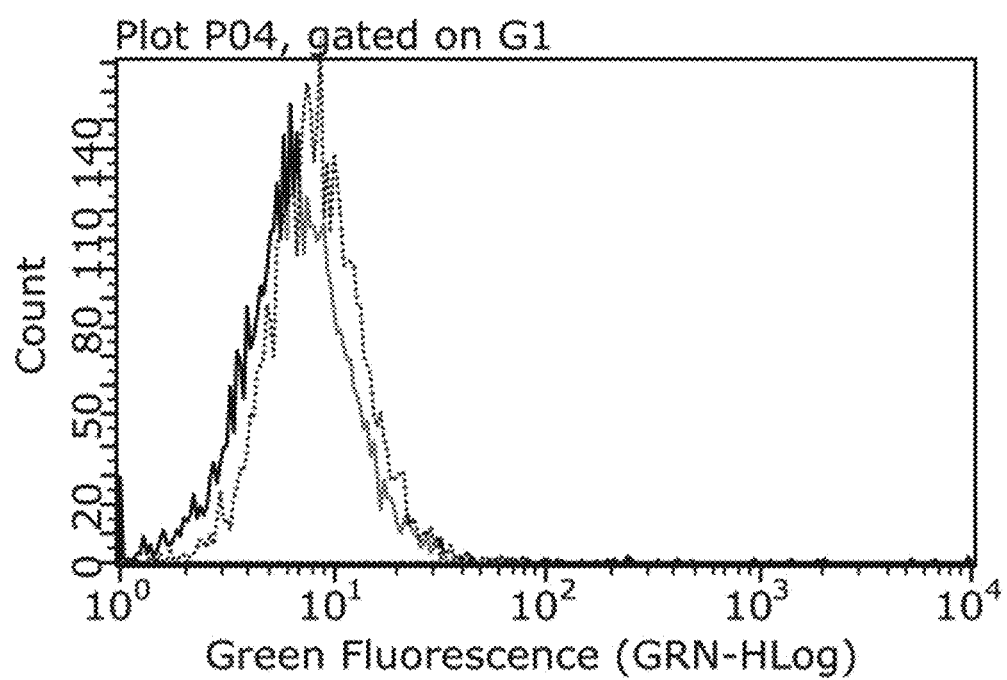
FIG. 10C is a graph illustrating the degree of Thy1 expression in 293T embryonic kidney cells.

Referring to FIGS. 10B and 10C, there was almost no expression of Thy1 protein in NIH3T3 and 293T, but the expression of Thy1 in PC12 neurons of FIG. 10A was very high. That is, it is considered that the activity of the transcriptional regulatory factors for Thy1 expression is high in PC12 cells, indicating that the promoter of the disclosure plays a very large role in neuronal-specific expression.

Example 6: Expression Analysis after Transfection of a Vector Binding Thy1 Promoter and EGFP to PC12 Cells Stable cells were prepared by transfection of pEGFP1 (cmv promoter) and pThy1-EGFP (Thy1 promoter) into PC12 cells rich in transcriptional regulatory factors for Thy1 protein expression and treatment with 400 µg/ml of G418 for about 3 weeks. The expression of GFP in PC12 cells was investigated by flow cytometry and fluorescence microscopy.

Figure 11A:
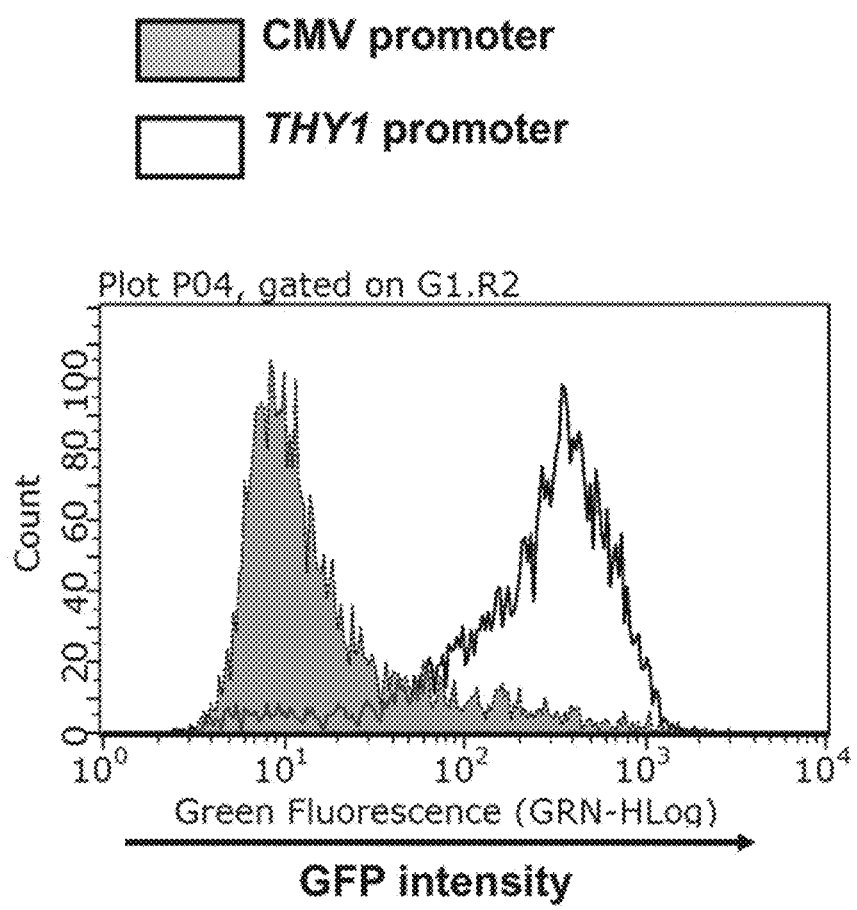
FIG. 11A is a graph in which the degree of expression of GFP in PC12 cells was analyzed.
Figure 11B:
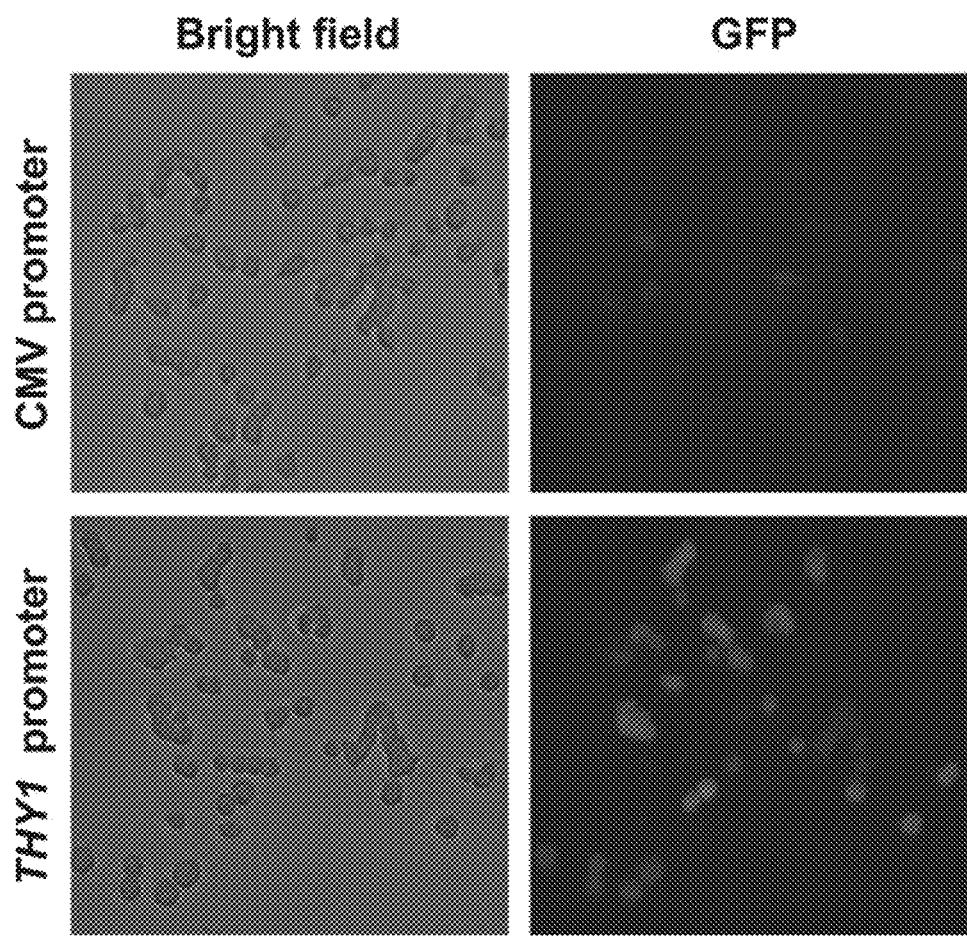
FIG. 11B is a photograph illustrating the degree of expression of GFP in PC12 cells.

FIG. 11A is a graph in which the degree of expression of GFP in PC12 cells was analyzed, and FIG. 11B is a photograph illustrating the degree of expression of GFP in PC12 cells.

Referring to FIG. 11A, the expression of GFP under the control of the Thy1 promoter is markedly higher than the expression of GFP under the control of the CMV promoter.

Example 7: Luciferase Reporter Analysis for Analysis of Important Sites in the Activity of the Thy1 Promoter In order to investigate the location of sequence inducing neuronal-specific expression in the sequence of the −4858 to −2279 Thy1 promoter, a region close to −4858 was excised to PCR-synthesize −3880/−2279, −3380/−2279, −2880/−2279 Thy1 promoter site. After cutting it with SacI/NheI restriction enzyme, it was cloned into pGL4.10[luc2].

Figure 12:
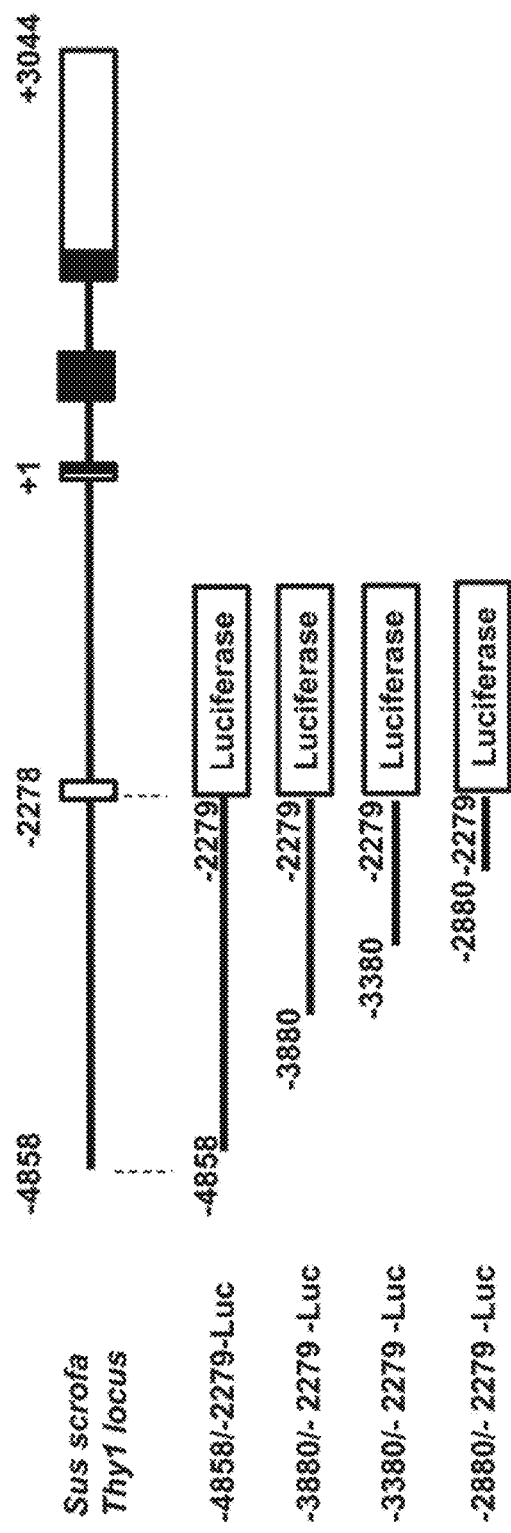
FIG. 12 illustrates the Thy1 promoter region of the luciferase reporter vector.

FIG. 12 illustrates the Thy1 promoter site of a luciferase reporter vector.

After luciferase reporter vector (500 ng) and pRL-TK (50 ng) were transfected with lipofectamin 2000 in 293T and PC12 cells, luciferase assay was performed.

Figure 13:
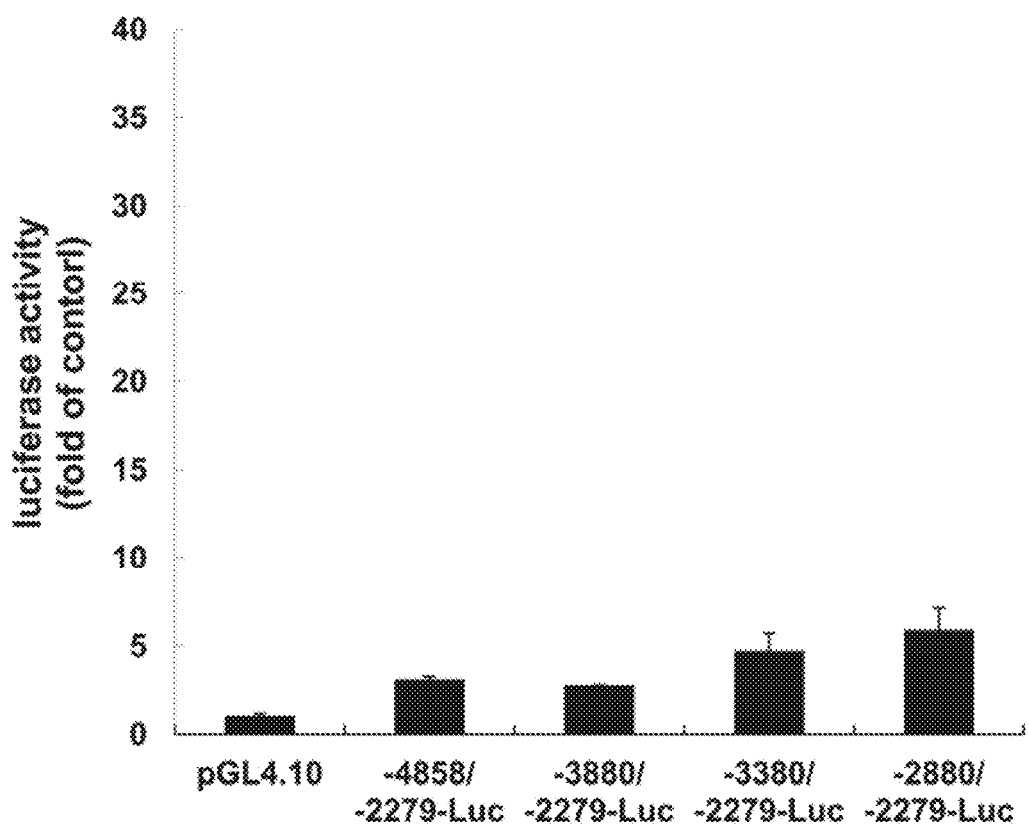
FIG. 13 is a graph illustrating the activity after transfection of each vector into 293T cells.
Figure 14:
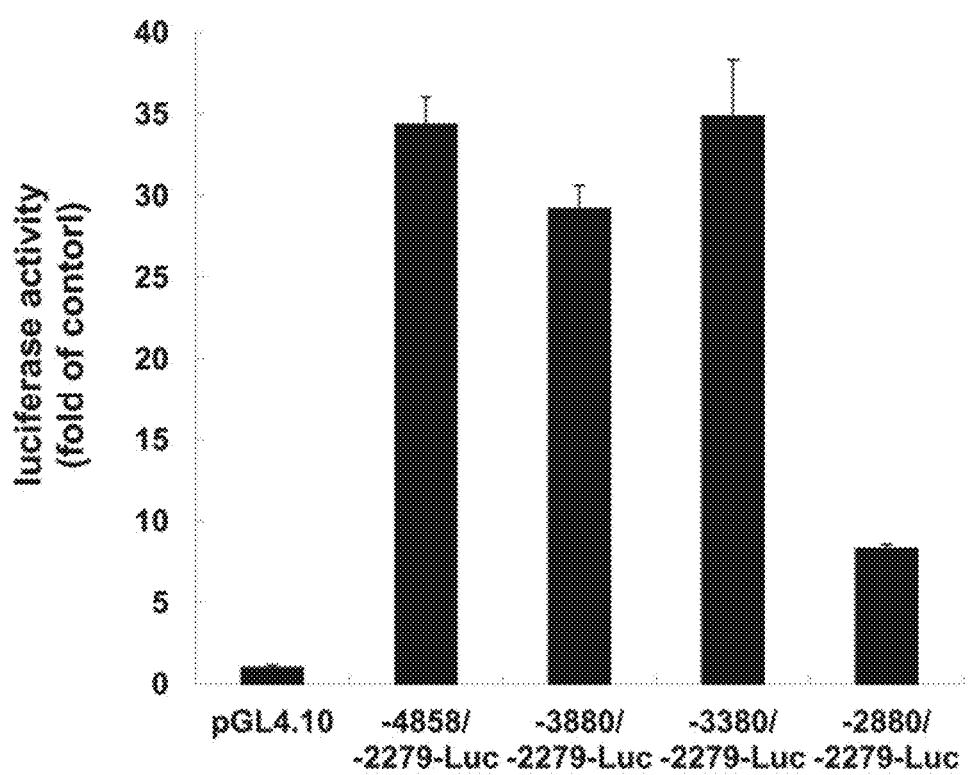
FIG. 14 is a graph illustrating the activity after transfection of each vector into PC12 cells.

FIG. 13 is a graph illustrating the activity after transfection of each vector into 293T cells, and FIG. 14 is a graph illustrating the activity after transfection of each vector into PC12 cells.

Referring to FIG. 13, it was analyzed that the activity of a promoter was low in 293T cells. On the contrary, referring to FIG. 14, the activity of the Thy1 promoter was very high in the case of −4858/−2279-Luc, −3880/−2279-Luc and −3380/−2279-Luc in the PC12 neuronal cell line; however, in the case of −2880/−2279-Luc, the activity of a promoter was remarkably decreased. That is, it indicates that the DNA sequence of about 500 bp from −3380 to −2880 of the Thy1 promoter inducing neuronal-specific expression is important.

Example 8: Completion of pTet Retrovirus Multi-Systronic Vector into which Alzheimer's Disease Gene is Introduced The retroviral vector pTet-CKOS was used to remove the TRE minimal CMV promoter and CKOS gene cluster present in this vector. It was modified to a vector having restriction enzyme sites such as SwaI, ClaI, PacI, and NotI so as to be advantageous for gene cloning.

In order to induce amino acid mutations of the precursor protein (APP) gene (NM_201414.2), the precenillin (PS-1) gene (NM_000021.3) and the Tau gene (NM_016834.4) of the Alzheimer's disease mutant gene β-amyloid, a site-directed mutagenesis kit (Stratagene) was used. In the case of APP, APP695 type gene expressed in brain cells was used and two double mutations were introduced at 595 and 596 in which a familial mutation of the gene of Alzheimer's disease was found. These mutations are known to produce more β-amyloid 42 forms. The amino acid mutations were named K595N and N596M, respectively. Two amino acid mutations were also introduced in the presenilin. Mutations of amino acids 146 and 286 were introduced and named as M146L and P286L, respectively. In the case of Tau, only one amino acid at the 243th position was mutated and named P243L.

The three genes were transcribed into a single mRNA and then linked to each other in a 2A sequence so that they were separated into independent peptides when translated into proteins, respectively.

Finally, a 1079 bp-sized Thy1 promoter was inserted into the retroviral vector using two of SwaI and ClaI restriction enzymes, followed by completion of a final recombinant expression vector, pTet-porcine TYH1 pro-APPsw-2A-TAU-2A-PS1-SV40 pA, in which three mutant genes were linked in a tandem. The complete recombinant expression vector was confirmed to have a total DNA sequence of 13,874 bp after base sequencing.

SEQ ID NO: 12 exhibits the base sequence (13,874 bp) of the above-mentioned complete recombinant expression vector.

Figure 15:
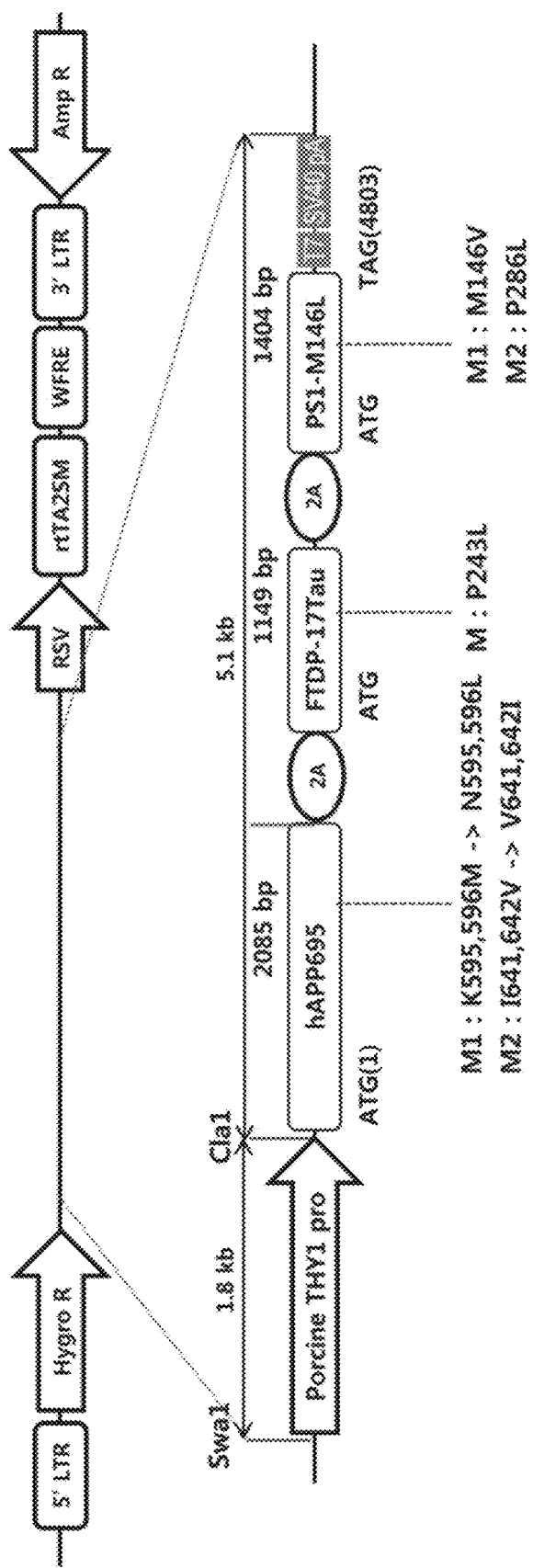
FIG. 15 is a schematic diagram illustrating a one-dimensional structure of a multi-systolic vector of pTet retrovirus prepared so that hAPP, hTau and PSEN1 genes are expressed using a Thy1 promoter.
Figure 16:
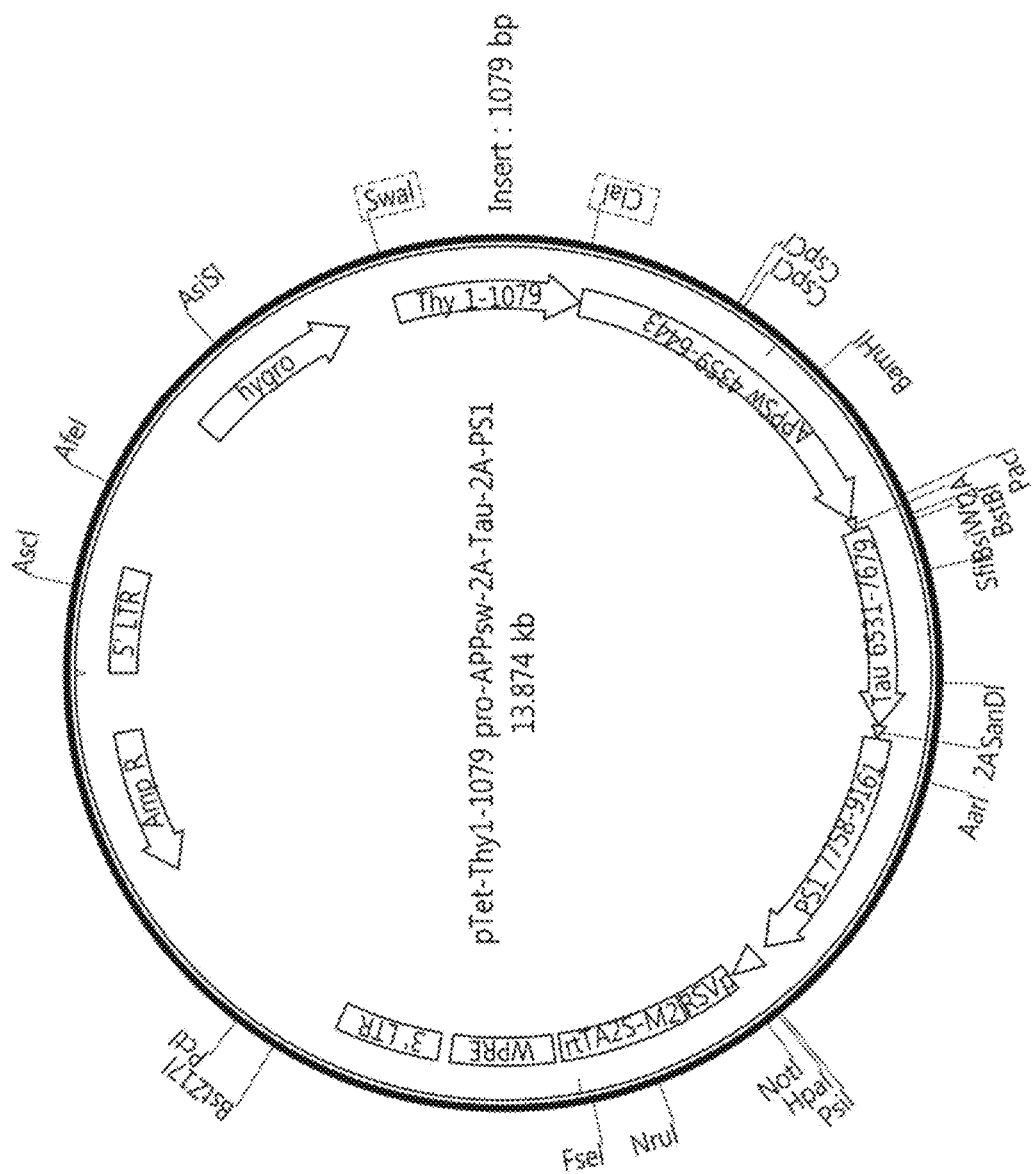
FIG. 16 is a schematic diagram illustrating a cyclic structure of a multi-systolic vector of pTet retrovirus prepared so that hAPP, hTau and PSEN1 gene are expressed using a Thy1 promoter.

FIG. 15 illustrates a one-dimensional structure of a multi-systolic vector of pTet retrovirus prepared to express hAPP, hTau and PSEN1 genes using a Thy1 promoter, and FIG. 16 illustrates a cyclic structure thereof.

While the examples as above have been described with reference to the limited examples and drawings, it will be understood by a person having ordinary skill in the pertinent technical field that various changes and modifications may be made. For example, suitable results may be achieved if the described techniques are performed in a different order than the described methods, and/or if the described constituents are linked or combined in other ways than the described methods, or are replaced or substituted by other constituents or their equivalents.

Therefore, other implementations, other embodiments, and other equivalents are also within the scope of the following claims.

Seqyebce list Free Text

SEQ ID NO: 1

```
gaagccacaa ggatgcaaat caatcaaata aacctttgtt caaaaaaatt tatctcacct    60
gtgagtggga gagacaagtc accccagggc ttctggtgac ttcaaattga tagggagaaa   120
atggttgccc caggggatta aaagcttggt atctgctact cctttagagt tggcctgtct   180
cctccacttt cccacaattc caccatttcc ccctcccact gggctgggat gcagctgtgg   240
agtggctcag ctccaaggac tagggctcc acagcccagg tccggcggcc agccctccca   300
cttccagcct ggaagtggga tggggagtgg gatgagatga acccggcaga ttgtagccac   360
agatgtggat gtgcagggtc cagcacaggg cttgggtgag gagggcggca ccccatccct   420
tgtctgaaga ccaagcagac agtactcagg acttgggagg gggttggggg aggaggagtg   480
```

-continued catgaaactg agaagaacct

SEQ ID NO: 2
gaagccacaa ggatgcaaat

SEQ ID NO: 3
aggttcttct cagtttcatg

SEQ ID NO: 4
tctagatggg gcaactggag atgatgggag aagaaagcct aagggactaa gaggaaagcc    60
acaatctgtc ggtaaatcct gccttgggta gaatcttcta aacctttccc gctttcagca   120
ctcttatcct gtcccacagg caaaggggag tttttaaatc tcctctccat caccatcttg   180
tgttccgccc tggttcctaa ttgtcttact tgagccattc actccatcca gccgagacct   240
tgttttagca gacacacaac tgcctagagt ctacacgccc ctccctttcc caaactaaag   300
tgcttaggga cccagaaaat aggccaggtc ctcgtaacct tatcgaaata gcacagctag   360
gccttccacc caacaacact cagagactgg gccatagggt aggaaacagc atccagagtc   420
ttgtccagac agagcccaga catcttctgt agttaagagc cctctgggta ttctcacgtc   480
ctgccccaaa aaaggaacc aagcttatct gggggcggtg gggagaaggg ggtgtaagcc   540
aaagctaaag caactaaagc aactgtgttc tgataggaaa gatccctgga ctgagaacaa   600
gaaagctgtt ccgcaggaaa gaacacactg cgtggagtgt cagggaggag gccagcacct   660
ctggaatgcg gcaggaagat gaatgggaaa gatgaggtgg tggtggaggg cagcagccag   720
ggccttcaaa atcatcctcc agacaatgac aagcccggtc acctgatctg tgaagaggga   780
tggtctgcaa tctccaggcc ctcgagcctg tgcaaaggc aggctcaggc agctctgctg   840
ctagactaag gacatcccag gtgggcacgg agagctgcat ttctcgtaaa gcgccctagg   900
agcttctgtt gttcaccaga accacgagcc cctggactgg accgttcaca aggctcgttc   960
cagttagaaa attccatcac tctaagagct gggaggcacc taacctccaa gggagggaga  1020
gggaagtgga tctcccactt gccagcccag ggatgacttc caacagtgcc attacagtaa  1080
tggaaactgc agtgaaggtg ccagggctga cttctgtgaa gaaagaggag acaggagtt  1140 cccctagtgg ctcatcagaa atgaatctga ctagcatcca tgaggatgca ggttcaatcc  1200
ctggcctcat tcagtggctt aaggatccag cgttgccgag agctgtgatg taggtcacag  1260
acgcggctca gatcccgtgt tgctgttgct gtggctgtgg cataggtcag aagcgacagc  1320
tctgatttga cccctaacct gggaacctcc atatcccgct agtgcggccc ttaaaagaca  1380
aaaagaagga aaagagaaga aaagacatag gcgaacagaa aggcagatga cagggtggca  1440
gggccagcct acacgatggc ccgaccagaa ttcacaaaga agccacaagg atgcaaatca  1500
atcaaataaa cctttgttca aaaaaattta tctcacctgt gagtgggaga gacaagtcac  1560
cccagggctt ctggtgactt caaattgata gggagaaaat ggttgcccca ggggattaaa  1620
agcttggtat ctgctactcc tttagagttg gcctgtctcc tccactttcc cacaattcca  1680
ccatttcccc ctcccactgg gctgggatgc agctgtggag tggctcagct ccaaggacta  1740
ggggctccac agcccaggtc cggcggccag ccctcccact tccagcctgg aagtgggatg  1800
gggagtggga tgagatgaac ccggcagatt gtagccacag atgtggatgt gcagggtcca  1860
gcacagggct tgggtgagga gggcggcacc ccatcccttg tctgaagacc aagcagacag  1920
tactcaggac ttgggagggg gttggggag gaggagtgca tgaaactgag aagaaccttc  1980
tagctgcctg cgccaggagg tacccgggag ctgaaggaga tggagtgccc cagagcagaa  2040 agccctgca ggtctggatg ttctaggctg gatgaggggg cgaggcaggc ctggggacct  2100
gggaagacca ggcgcagtac ctgccttgct tctgaaaatg ctgctccaac gtggaaaaac  2160

-continued

| | |
|---|---|
| actcccacca tctttctttg gagaaagcct gtaatattcc aacaccaaaa cctctcacta | 2220 |
| gaggttcccg tggagatggg ttccagatga aaagggaagg aggaggcatg ggcgctgcct | 2280 |
| aacctccatc ctccattcct taccctctc ccaccggctt ctgaagccgg ggtcagaaga | 2340 |
| aagggttaaa gccttaaaag gggaccgatt ttgcggggct ctgggggtcg gctggcacac | 2400 |
| cctgagcggc cccgcccttc tctctagtgt ccagaaccct ccctgccctg cccaggccta | 2460 |
| acggccacag ggggagggcc cccctttact gcagaccgcc actctcccac accaatatcg | 2520 |
| gaccgcctcc tcctccctct gccaccccctt ctcgctcccc actcagcctc tgattggcc | |

SEQ ID NO: 5 tctagatggg gcaactggag

SEQ ID NO: 6 ggccaatcag aggctgagtg

SEQ ID NO: 7

| | |
|---|---|
| tctagatggg gcaactggag atgatgggag aagaaagcct aagggactaa gaggaaagcc | 60 |
| acaatctgtc ggtaaatcct gccttgggta gaatcttcta aacctttccc gctttcagca | 120 |
| ctcttatcct gtcccacagg caaaggggag tttttaaatc tcctctccat caccatcttg | 180 |
| tgttccgccc tggttcctaa ttgtcttact tgagccattc actccatcca gccgagacct | 240 |
| tgttttagca gacacacaac tgcctagagt ctacacgccc ctccctttcc caaactaaag | 300 |
| tgcttaggga cccagaaaat aggccaggtc tcgtaacct tatcgaaata gcacagctag | 360 |
| gccttccacc caacaacact cagagactgg gccatagggt aggaaacagc atccagagtc | 420 |
| ttgtccagac agagcccaga catcttctgt agttaagagc cctctgggta ttctcacgtc | 480 |
| ctgccccaaa aaaggaacc aagcttatct gggggcggtg gggagaaggg ggtgtaagcc | 540 |
| aaagctaaag caactaaagc aactgtgttc tgataggaaa gatccctgga ctgagaacaa | 600 |
| gaaagctgtC ccgcaggaaa gaacacactg cgtggagtgt cagggaggag gccagcacct | 660 |
| ctggaatgcg gcaggaagat gaatgggaaa gatgaggtgg tggtggaggg cagcagccag | 720 |
| ggccttcaaa atcatcctcc agacaatgac aagcccggtc acctgatctg tgaagaggga | 780 |
| tggtctgcaa tctccaggcc ctcgagcctg tgcaaagggc aggctcaggc agctctgctg | 840 |
| ctagactaag gacatcccag gtgggcacgg agagctgcat ttctcgtaaa gcgccctagg | 900 |
| agcttctgtt gttcaccaga accacgagcc cctggactgg accgttcaca aggctcgttc | 960 |
| cagttagaaa attccatcac tctaagagct gggaggcacc taacctccaa gggagggaga | 1020 |
| gggaagtgga tctcccactt gccagcccag ggatgacttc caacagtgcc attacagtaa | 1080 |
| tggaaactgc agtgaaggtg ccaggggctga cttctgtgaa gaaagaggag gacaggagtt | 1140 |
| cccctagtgg ctcatcagaa atgaatctga ctagcatcca tgaggatgca ggttcaatcc | 1200 |
| ctggcctcat tcagtggctt aaggatccag cgttgccgag agctgtgatg taggtcacag | 1260 |
| acgcggctca gatcccgtgt tgctgttgct gtggctgtgg cataggtcag aagcgacagc | 1320 |
| tctgatttga cccctaacct gggaacctcc atatcccgct agtgcggccc ttaaaagaca | 1380 |
| aaagaagga aaagagaaga aaagacatag gcgaacagaa aggcagatga cagggtggca | 1440 |
| gggccagcct acacgatggc ccgaccagaa ttcacaaaga agccacaagg atgcaaatca | 1500 |
| atcaaataaa cctttgttca aaaaaattta tctcacctgt gagtgggaga gacaagtcac | 1560 |
| cccagggctt ctggtgactt caaattgata gggagaaaat ggttgcccca ggggattaaa | 1620 |
| agcttggtat ctgctactcc tttagagttg gcctgtctcc tccactttcc cacaattcca | 1680 |
| ccatttcccc ctcccactgg gctgggatgc agctgtggag tggctcagct ccaaggacta | 1740 |
| ggggctccac agcccaggtc cggcggccag ccctcccact tccagcctgg aagtgggatg | 1800 |

-continued

```
gggagtggga tgagatgaac ccggcagatt gtagccacag atgtggatgt gcagggtcca    1860
gcacagggct tgggtgagga gggcggcacc ccatcccttg tctgaagacc aagcagacag    1920
tactcaggac ttgggagggg gttggggggag gaggagtgca tgaaactgag aagaaccttc   1980
tagctgcctg cgccaggagg tacccgggag ctgaaggaga tggagtgccc cagagcagaa    2040
agcccctgca ggtctggatg ttctaggctg gatgagggg cgaggcaggc ctggggaccct    2100 gggaagacca ggcgcagtac ctgccttgct tctgaaaatg ctgctccaac gtggaaaaac    2160
actcccacca tctttctttg gagaaagcct gtaatattcc aacaccaaaa cctctcacta    2220
gaggttcccg tggagatggg ttccagatga aagggaagg aggaggcatg ggcgctgcct     2280
aacctccatc ctccattcct taccctctc ccaccggctt ctgaagccgg ggtcagaaga     2340
aagggttaaa gccttaaaag gggaccgatt ttgcggggct ctggggggtcg gctggcacac   2400 cctgagcggc cccgcccttc tctctagtgt ccagaaccct ccctgccctg cccaggccta    2460
acggccacag ggggagggcc cccctttact gcagaccgcc actctcccac accaatatcg    2520
gaccgcctcc tcctccctct gccacccctt ctcgctcccc actcagcctc tgattggcc
```

```
                                                              SEQ ID NO: 8
aacctccatc ctccattcct taccctctc ccaccggctt ctgaagccgg ggtcagaaga       60
aagggttaaa gccttaaaag gggaccgatt ttgcggggct ctggggggtcg gctggcacac    120 cctgagcggc cccgcccttc tctctagtgt ccagaaccct ccctgccctg cccaggccta    180
acggccacag ggggagggcc cccctttact gcagaccgcc actctcccac accaatatcg    240
gaccgcctcc tcctccctct gccacccctt ctcgctcccc actcagcctc tgattggccg    300 agccccccggg tcctccccgc ccctcctctc ccacccttgg tgaaaactgc gggtgccggg   360
cagggtgcag caactggagg cggcggcgtg tccggagcag tctgcggcgg cgagggaccg    420
gaacccaggt gggaactgga gccagggcgg ggcccggagc gccctcggtg ccctgcaag     480 ctctccagac cccaagcttc agaaaaccat ccgagggcgc tcaggaagg agcagtgcag     540 ggcctgggga ggggtctgct tcccaggcag gggcgggagc cggacgccaa ggctgcaggc    600
cgggggccgc aacgcatctt tcgcccgctc ggaggacgtt tgcctggggc ggggcgctg    660 gaggagaact gggaggaagg gcgccaagga cagttttggg ttctgctcgc cacccacaca   720
tccccaagcc ccgcttgcaa agacaggggc gggggcgac gaaactcggg ggagagaacc    780
gaggacccca aactagaggg aatctctgcc ctccgacctc gcgacaggct gggtgcgggg   840
catccaagga acgggaaacc gcagtgccgc gggcggggac tgggaggaag gcaggcagac   900 ggggggaggcg agaactggaa aaggatgaga gaggggaag gggacttca attgggaatg    960 gaggagattg gaatggggag acggaataag ggtggggtta gtcgaacgcg tgctgagagg   1020
gagggaacgc aaagcttctg cgggttctga gctgcgggga cccaggaaac gaaaacagac   1080
tgcgcctccc ctaccagctg tctaccccctc cctttggctc tccatcccct gccagcccca   1140
gccccgtttc ttccttttcta ccccttcctc tcctggatcc cgagctcaca ctcctcctct   1200
gtaactcagc gtccgctaat caaaaccaga tgtcagtccc cctttcttcc ccagcagcac    1260
ctccgggtcc ctctcggcag gggtctggga aggagttgac tgcgtccgcg ggcgccgcag   1320
taccccagcc tcgcccctcc ctccccacct ctgggagctg ggctgaacgc ctgggaccct   1380
ggaagccgcg agtcgcgcgc cctgcgcacc cggccgaccc cctcctgtg gcctctccct    1440 ggagaactcc gctgcggaca ggctaggcta cctgctctgt gtctccttgc cagaatattg    1500
attcagccta ggctgcaaaa ataagacagg gcagagaacc taggcaggga ggctatggaa    1560
gccaaactgg aaaactgcaa gcccaagaat tcctcctgga gagctagaga attggaaagg   1620
```

-continued

```
tcttggttcc aaggcagaga acacatgcac gcatttgcaa taggacagca ctgccgtttt    1680
cctcacaccc ttcgctgtgg gccaagtaca atcctacctg gggccccaca catacctgac    1740
gtcatccctg gccacacagt catctaagag aaaggaaatt aatgtttgtg gatcacttac    1800
ttacagtgcc aaatgtttgt catttttctt aatctccatc acggcccgt gttatgtatc     1860
taaagcccag tttcgttcag tatctttcag gcatctgtta tctgccagaa aggtctggcc    1920
atcggggatt ttcttctgaa tacgaaatag gaagtctttg tttaacaggt agagcgtttt    1980
agttttgcag gatgtcaaga gttctggaaa ttggttgcac cacaatgtaa atgaacttaa    2040
cacttctgaa ctgtacactt aaaaatggtt taggagagga gttccctggt ggcctgggag    2100
ttaagaacta ggcattgtca ctgctgtggc tcaggtttga ccctggctgg ggaaattctg    2160
catgccacag gcacagcccc gccaaaaatg gttataataa taaatgttat gttctgcgaa    2220
ttttactaaa aaataggaag tccctatctt cctgaaggga agaggaagtg gtaatttcaa    2280
gacacttact caaagtcacc caactagtaa gcattcagca cagataccca ccaccaaagg    2340
gtatgttctc catccctctt gctttctctg actgggaaga gccgagtgtc tgtcacattc    2400
actgagaggt gggaggggag agggctacag agaggggctt ggatgccccc catggccatt    2460
atggcatgtc tcccaggggc ccccaggcct ggcagtaaat gtgggcacac ctgccccgcc    2520
tcttggctga ttcccacc
                                                    SEQ ID NO: 9
ggcctaactg gccggtacct gagctcgcta gcctcgagga tatcaagatc tggcctcggc      60
ggccaagctt ggcaatccgg tactgttggt aaagccacca tggaagatgc caaaaacatt     120
aagaagggcc cagcgccatt ctacccactc gaagacggga ccgccggcga gcagctgcac     180
aaagccatga gcgctacgc cctggtgccc ggcaccatcg cctttaccga cgcacatatc      240
gaggtggaca ttacctacgc cgagtacttc gagatgagcg ttcggctggc agaagctatg     300
aagcgctatg gctgaatac aaaccatcgg atcgtggtgt gcagcgagaa tagcttgcag      360
ttcttcatgc ccgtgttggg tgccctgttc atcggtgtgg ctgtggcccc agctaacgac     420
atctacaacg agcgcgagct gctgaacagc atgggcatca gccagcccac cgtcgtattc     480
gtgagcaaga aagggctgca aaagatcctc aacgtgcaaa agaagctacc gatcatacaa     540
aagatcatca tcatggatag caagaccgac taccagggct tccaaagcat gtacaccttc     600
gtgacttccc atttgccacc cggcttcaac gagtacgact tcgtgcccga gagcttcgac     660
cgggacaaaa ccatcgccct gatcatgaac agtagtggca gtaccggatt gcccaagggc     720
gtagccctac cgcaccgcac cgcttgtgtc cgattcagtc atgcccgcga ccccatcttc     780
ggcaaccaga tcatccccga caccgctatc ctcagcgtgg tgccatttca ccacggcttc     840
ggcatgttca ccacgctggg ctacttgatc tgcggctttc gggtcgtgct catgtaccgc     900
ttcgaggagg agctattctt gcgcagcttg caagactata gattcaatc tgccctgctg      960
gtgcccacac tatttagctt cttcgctaag agcactctca tcgacaagta cgacctaagc    1020
aacttgcacg agatcgccag cggcggggcg ccgctcagca aggaggtagg tgaggccgtg    1080
gccaaacgct tccacctacc aggcatccgc caggcctacg gcctgacaga aacaaccagc    1140
gccattctga tcacccccga aggggacgac aagcctggcg cagtaggcaa ggtggtgccc    1200
ttcttcgagg ctaaggtggt ggacttggac accggtaaga cactgggtgt gaaccagcgc    1260
ggcgagctgt gcgtccgtgg ccccatgatc atgagcggct acgttaacaa ccccgaggct    1320
acaaacgctc tcatcgacaa ggacggctgg ctgcacagcg gcgacatcgc ctactgggac    1380
gaggacgagc acttcttcat cgtggaccgg ctgaagagcc tgatcaaata caagggctac    1440
```

-continued

```
caggtagccc cagccgaact ggagagcatc ctgctgcaac accccaacat cttcgacgcc  1500
ggggtcgccg gcctgccCga cgacgatgcc ggcgagctgc ccgccgcagt cgtcgtgctg  1560
gaacacggta aaaccatgac cgagaaggag atcgtggact atgtggccag ccaggttaca  1620
accgccaaga agctgcgcgg tggtgttgtg ttcgtggacg aggtgcctaa aggactgacc  1680
ggcaagttgg acgcccgcaa gatccgcgag attctcatta aggccaagaa gggcggcaag  1740
atcgccgtgt aataattcta gagtcggggc ggccggccgc ttcgagcaga catgataaga  1800
tacattgatg agtttggaca aaccacaact agaatgcagt gaaaaaaatg ctttatttgt  1860
gaaatttgtg atgctattgc tttatttgta accattataa gctgcaataa acaagttaac  1920
aacaacaatt gcattcattt tatgtttcag gttcaggggg aggtgtggga ggttttttaa  1980
agcaagtaaa acctctacaa atgtggtaaa atcgataagg atccgtcgac cgatgccctt  2040
gagagccttc aacccagtca gctccttccg gtgggcgcgg ggcatgacta tcgtcgccgc  2100
acttatgact gtcttcttta tcatgcaact cgtaggacag gtgccggcag cgctcttccg  2160
cttcctcgct cactgactcg ctgcgctcgg tcgttcggct gcggcgagcg gtatcagctc  2220
actcaaaggc ggtaatacgg ttatccacag aatcagggga taacgcagga agaacatgt  2280 gagcaaaagg ccagcaaaag gccaggaacc gtaaaaaggc cgcgttgctg gcgttttcc  2340 ataggctccg ccccCctgac gagcatcaca aaaatcgacg ctcaagtcag aggtggcgaa  2400
acccgacagg actataaaga taccaggcgt ttccccctgg aagctccctc gtgcgctctc  2460
ctgttccgac cctgccgctt accggatacc tgtccgcctt tctcccttcg ggaagcgtgg  2520
cgctttctca tagctcacgc tgtaggtatc tcagttcggt gtaggtcgtt cgctccaagc  2580
tgggctgtgt gcacgaaccc cccgttcagc ccgaccgctg cgccttatcc ggtaactatc  2640
gtcttgagtc caacccggta agacacgact tatcgccact ggcagcagcc actggtaaca  2700
ggattagcag agcgaggtat gtaggcggtg ctacagagtt cttgaagtgg tggcctaact  2760
acggctacac tagaagaaca gtatttggta tctgcgctct gctgaagcca gttaccttcg  2820
gaaaaagagt tggtagctct tgatccggca aacaaaccac cgctggtagc ggtggttttt  2880
ttgtttgcaa gcagcagatt acgcgcagaa aaaaaggatc tcaagaagat cctttgatct  2940
tttctacggg gtctgacgct cagtggaacg aaaactcacg ttaagggatt ttggtcatga  3000
gattatcaaa aaggatcttc acctagatcc ttttaaatta aaaatgaagt tttaaatcaa  3060
tctaaagtat atatgagtaa acttggtctg acagcggccg caaatgctaa accactgcag  3120
tggttaccag tgcttgatca gtgaggcacc gatctcagcg atctgcctat ttcgttcgtc  3180
catagtggcc tgactccccg tcgtgtagat cactacgatt cgtgagggct taccatcagg  3240
ccccagcgca gcaatgatgc cgcgagagcc gcgttcaccg gccccgatt tgtcagcaat  3300 gaaccagcca gcagggaggg ccgagcgaag aagtggtcct gctactttgt ccgcctccat  3360
ccagtctatg agctgctgtc gtgatgctag agtaagaagt tcgccagtga gtagtttccg  3420
aagagttgtg gccattgcta ctggcatcgt ggtatcacgc tcgtcgttcg gtatggcttc  3480
gttcaactct ggttcccagc ggtcaagccg ggtcacatga tcacccatat tatgaagaaa  3540
tgcagtcagc tccttagggc ctccgatcgt tgtcagaagt aagttggccg cggtgttgtc  3600
gctcatggta atggcagcac tacacaattc tcttaccgtc atgccatccg taagatgctt  3660
ttccgtgacc ggcgagtact caaccaagtc gttttgtgag tagtgtatac ggcgaccaag  3720
ctgctcttgc ccggcgtcta tacgggacaa caccgcgcca catagcagta ctttgaaagt  3780
gctcatcatc gggaatcgtt cttggggcg gaaagactca aggatcttgc cgctattgag  3840
atccagttcg atatagccca ctcttgcacc cagttgatct tcagcatctt ttactttcac  3900
```

-continued

```
cagcgtttcg gggtgtgcaa aaacaggcaa gcaaaatgcc gcaaagaagg gaatgagtgc    3960
gacacgaaaa tgttggatgc tcatactcgt ccttttcaa tattattgaa gcatttatca     4020
gggttactag tacgtctctc aaggataagt aagtaatatt aaggtacggg aggtattgga    4080
caggccgcaa taaatatct ttattttcat tacatctgtg tgttggtttt ttgtgtgaat     4140
cgatagtact aacatacgct ctccatcaaa acaaaacgaa acaaaacaaa ctagcaaaat    4200
aggctgtccc cagtgcaagt gcaggtgcca gaacatttct ct
```

SEQ ID NO: 10

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccaccca ttgacgtcaa tgggagtttg ttttggcacc aaaatcaacg     480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatccaccgt cgccaccat ggtgagcaag ggcgaggagc tgttcaccgg ggtggtgccc      720
atcctggtcg agctggacgg cgacgtaaac ggccacaagt tcagcgtgtc cggcgagggc    780
gagggcgatg ccacctacgg caagctgacc ctgaagttca tctgcaccac cggcaagctg    840
cccgtgccct ggcccaccct cgtgaccacc ctgacctacg gcgtgcagtg cttcagccgc    900
taccccgacc acatgaagca gcacgacttc ttcaagtccg ccatgcccga aggctacgtc    960
caggagcgca ccatcttctt caaggacgac ggcaactaca agacccgcgc cgaggtgaag    1020
ttcgagggcg acaccctggt gaaccgcatc gagctgaagg gcatcgactt caaggaggac    1080
ggcaacatcc tggggcacaa gctggagtac aactacaaca gccacaacgt ctatatcatg    1140
gccgacaagc agaagaacgg catcaaggtg aacttcaaga tccgccacaa catcgaggac    1200
ggcagcgtgc agctcgccga ccactaccag cagaacaccc ccatcggcga cggccccgtg    1260
ctgctgcccg acaaccacta cctgagcacc cagtccgccc tgagcaaaga ccccaacgag    1320
aagcgcgatc acatggtcct gctggagttc gtgaccgccg ccgggatcac tctcggcatg    1380
gacgagctgt acaagtaaag cggccgcgac tctagatcat aatcagccat accacatttg    1440
tagaggtttt acttgcttta aaaaacctcc cacacctccc cctgaacctg aaacataaaa    1500
tgaatgcaat tgttgttgtt aacttgttta ttgcagctta taatggttac aaataaagca    1560
atagcatcac aaatttcaca aataaagcat ttttttcact gcattctagt tgtggtttgt    1620
ccaaactcat caatgtatct taaggcgtaa attgtaagcg ttaatatttt gttaaaattc    1680
gcgttaaatt tttgttaaat cagctcattt tttaaccaat aggccgaaat cggcaaaatc    1740
ccttataaat caaagaata gaccgagata gggttgagtg ttgttccagt ttggaacaag    1800
agtccactat taaagaacgt ggactccaac gtcaaagggc gaaaaaccgt ctatcagggc    1860
gatggcccac tacgtgaacc atcaccctaa tcaagttttt tggggtcgag gtgccgtaaa    1920
gcactaaatc ggaaccctaa agggagcccc cgatttagag cttgacgggg aaagccggcg    1980
aacgtggcga gaaaggaagg gaagaaagcg aaaggagcgg gcgctagggc gctggcaagt    2040
```

-continued

```
gtagcggtca cgctgcgcgt aaccaccaca cccgccgcgc ttaatgcgcc gctacagggc    2100
gcgtcaggtg gcacttttcg gggaaatgtg cgcggaaccc ctatttgttt attttttctaa   2160 atacattcaa atatgtatcc gctcatgaga caataaccct gataaatgct tcaataatat   2220
tgaaaaagga agagtcctga ggcggaaaga accagctgtg gaatgtgtgt cagttagggt    2280
gtggaaagtc cccaggctcc ccagcaggca gaagtatgca aagcatgcat ctcaattagt    2340
cagcaaccag gtgtggaaag tccccaggct ccccagcagg cagaagtatg caaagcatgc    2400
atctcaatta gtcagcaacc atagtcccgc ccctaactcc gcccatcccg cccctaactc    2460
cgcccagttc cgcccattct ccgccccatg gctgactaat ttttttttatt tatgcagagg   2520 ccgaggccgc ctcggcctct gagctattcc agaagtagtg aggaggcttt tttggaggcc    2580
taggcttttg caaagatcga tcaagagaca ggatgaggat cgtttcgcat gattgaacaa    2640
gatggattgc acgcaggttc tccggccgct tgggtggaga ggctattcgg ctatgactgg    2700
gcacaacaga caatcggctg ctctgatgcc gccgtgttcc ggctgtcagc gcaggggcgc    2760
ccggttcttt ttgtcaagac cgacctgtcc ggtgccctga atgaactgca agacgaggca    2820
gcgcggctat cgtggctggc cacgacgggc gttccttgcg cagctgtgct cgacgttgtc    2880
actgaagcgg gaagggactg gctgctattg ggcgaagtgc cggggcagga tctcctgtca    2940
tctcaccttg ctcctgccga gaaagtatcc atcatggctg atgcaatgcg gcggctgcat    3000
acgcttgatc cggctacctg cccattcgac caccaagcga aacatcgcat cgagcgagca    3060
cgtactcgga tggaagccgg tcttgtcgat caggatgatc tggacgaaga gcatcagggg    3120
ctcgcgccag ccgaactgtt cgccaggctc aaggcgagca tgcccgacgg cgaggatctc    3180
gtcgtgaccc atggcgatgc ctgcttgccg aatatcatgg tggaaaatgg ccgcttttct    3240
ggattcatcg actgtggccg gctgggtgtg gcggaccgct atcaggacat agcgttggct    3300
acccgtgata ttgctgaaga gcttggcggc gaatgggctg accgcttcct cgtgctttac    3360
ggtatcgccg ctcccgattc gcagcgcatc gccttctatc gccttcttga cgagttcttc    3420
tgagcgggac tctggggttc gaaatgaccg accaagcgac gcccaacctg ccatcacgag    3480
atttcgattc caccgccgcc ttctatgaaa ggttgggctt cggaatcgtt ttccgggacg    3540
ccggctggat gatcctccag cgcggggatc tcatgctgga gttcttcgcc caccctaggg    3600
ggaggctaac tgaaacacgg aaggagacaa taccggaagg aacccgcgct atgacggcaa    3660
taaaaagaca gaataaaacg cacggtgttg ggtcgtttgt tcataaacgc ggggttcggt    3720
cccagggctg gcactctgtc gataccccac cgagaccccca ttggggccaa tacgcccgcg   3780
tttcttcctt ttccccaccc caccccccaa gttcgggtga aggcccaggg ctcgcagcca    3840
acgtcggggc ggcaggccct gccatagcct caggttactc atatatactt tagattgatt    3900
taaaacttca ttttttaattt aaaaggatct aggtgaagat cctttttgat aatctcatga    3960
ccaaaatccc ttaacgtgag ttttcgttcc actgagcgtc agaccccgta gaaaagatca    4020
aaggatcttc ttgagatcct ttttttctgc gcgtaatctg ctgcttgcaa acaaaaaaac    4080
caccgctacc agcggtggtt tgtttgccgg atcaagagct accaactctt tttccgaagg    4140
taactggctt cagcagagcg cagataccaa atactgtcct tctagtgtag ccgtagttag    4200
gccaccactt caagaactct gtagcaccgc ctacatacct cgctctgcta atcctgttac    4260
cagtggctgc tgccagtggc gataagtcgt gtcttaccgg gttggactca agacgatagt    4320
taccggataa ggcgcagcgg tcgggctgaa cggggggttc gtgcacacag cccagcttgg    4380
agcgaacgac ctacaccgaa ctgagatacc tacagcgtga gctatgagaa agcgccacgc    4440
```

-continued

```
ttcccgaagg gagaaaggcg gacaggtatc cggtaagcgg cagggtcgga acaggagagc    4500
gcacgaggga gcttccaggg ggaaacgcct ggtatcttta tagtcctgtc gggtttcgcc    4560
acctctgact tgagcgtcga tttttgtgat gctcgtcagg ggggcggagc ctatggaaaa    4620
acgccagcaa cgcggccttt ttacggttcc tggccttttg ctggccttt gctcacatgt    4680 tctttcctgc gttatcccct gattctgtgg ataaccgtat taccgccatg cat
```

SEQ ID NO: 11

```
tctagatggg gcaactggag atgatgggag aagaaagcct aagggactaa gaggaaagcc      60
acaatctgtc ggtaaatcct gccttgggta gaatcttcta aacctttccc gctttcagca     120
ctcttatcct gtcccacagg caaagggag ttttaaatc tcctctccat caccatcttg       180
tgttccgccc tggttcctaa ttgtcttact tgagccattc actccatcca gccgagacct    240
tgttttagca gacacacaac tgcctagagt ctacacgccc ctcccttcc caaactaaag     300 tgcttaggga cccagaaaat aggccaggtc ctcgtaacct tatcgaaata gcacagctag   360
gccttccacc caacaacact cagagactgg gccataggt aggaaacagc atccagagtc    420
ttgtccagac agagcccaga catcttctgt agttaagagc cctctgggta ttctcacgtc    480
ctgccccaaa aaaaggaacc aagcttatct gggggcggtg gggagaaggg ggtgtaagcc   540
aaagctaaag caactaaagc aactgtgttc tgataggaaa gatccctgga ctgagaacaa     600
gaaagctgtt ccgcaggaaa gaacacactg cgtggagtgt cagggaggag gccagcacct    660
ctggaatgcg gcaggaagat gaatgggaaa gatgaggtgg tggtggaggg cagcagccag   720
ggccttcaaa atcatcctcc agacaatgac aagcccggtc acctgatctg tgaagaggga    780
tggtctgcaa tctccaggcc ctcgagcctg tgcaaagggc aggctcaggc agctctgctg    840
ctagactaag gacatcccag gtgggcacgg agagctgcat ttctcgtaaa gcgccctagg    900
agcttctgtt gttcaccaga accacgagcc cctggactgg accgttcaca aggctcgttc    960
cagttagaaa attccatcac tctaagagct gggaggcacc taacctccaa gggagggaga   1020
gggaagtgga tctcccactt gccagcccag ggatgacttc caacagtgcc attacagtaa   1080
tggaaactgc agtgaaggtg ccagggctga cttctgtgaa gaaagaggag gacaggagtt   1140
cccctagtgg ctcatcagaa atgaatctga ctagcatcca tgaggatgca ggttcaatcc   1200
ctggcctcat tcagtggctt aaggatccag cgttgccgag agctgtgatg taggtcacag   1260
acgcggctca gatcccgtgt tgctgttgct gtggctgtgg cataggtcag aagcgacagc   1320
tctgatttga cccctaacct gggaaccctcc atatcccgct agtgcggccc ttaaaagaca   1380
aaaagaagga aaagagaaga aaagacatag gcgaacagaa aggcagatga cagggtggca   1440
gggccagcct acacgatggc ccgaccagaa ttcacaaaga agccacaagg atgcaaatca    1500
atcaaataaa cctttgttca aaaaaattta tctcacctgt gagtgggaga gacaagtcac    1560
cccagggctt ctggtgactt caaattgata gggagaaaat ggttgcccca ggggattaaa    1620
agcttggtat ctgctactcc tttagagttg gcctgtctcc tccactttcc cacaattcca    1680
ccatttcccc ctcccactgg gctgggatgc agctgtggag tggctcagct ccaaggacta    1740
ggggctccac agcccaggtc cggcggccag ccctcccact tccagcctgg aagtgggatg    1800
gggagtggga tgagatgaac ccggcagatt gtagccacag atgtggatgt gcagggtcca   1860
gcacagggct tgggtgagga gggcggcacc ccatcccttg tctgaagacc aagcagacag    1920
tactcaggac ttgggagggg gttggggag gaggagtgca tgaaactgag aagaaccttc     1980
tagctgcctg cgccaggagg tacccggag ctgaaggaga tggagtgccc cagagcagaa     2040
agcccctgca ggtctggatg ttctaggctg gatgaggggg cgaggcaggc ctgggaacct   2100
```

-continued

```
gggaagacca ggcgcagtac ctgccttgct tctgaaaatg ctgctccaac gtggaaaaac    2160
actcccacca tctttctttg gagaaagcct gtaatattcc aacaccaaaa cctctcacta    2220
gaggttcccg tggagatggg ttccagatga aagggaagg aggaggcatg ggcgctgcct     2280
aacctccatc ctccattcct taccectctc ccaccggctt ctgaagccgg ggtcagaaga    2340
aagggttaaa gccttaaaag gggaccgatt tgcggggct ctggggtcg gctggcacac     2400
cctgagcggc cccgcccCtc tctctagtgt ccagaaccct ccctgccctg cccaggccta    2460
acggccacag ggggagggcc cccctttact gcagaccgcc actctcccac accaatatcg    2520
gaccgcctcc tcctccctct gccaccccett ctcgctcccc actcagcctc tgattggcc
```

SEQ ID NO: 12
```
tttgaaagac cccacccgta ggtggcaagc tagcttaagt aacgccactt tgcaaggcat     60
ggaaaaatac ataactgaga atagaaaagt tcagatcaag gtcaggaaca agaaaacagc    120
tgaataccaa acaggatatc tgtggtaagc ggttcctgcc ccggctcagg gccaagaaca    180
gatgagacag ctgagtgatg ggccaaacag gatatctgtg gtaagcagtt cctgccccgg    240
ctcggggcca agaacagatg gtccccagat gcggtccagc cctcagcagt ttctagtgaa    300
tcatcagatg tttccagggt gccccaagga cctgaaaatg accctgtacc ttatttgaac    360
taaccaatca gttcgcttct cgcttctgtt cgcgcgcttc cgctctccga gctcaataaa    420
agagcccaca cccctcact cggcgcgcca gtcttccgat agactgcgtc gcccgggtac     480
ccgtattccc aataaagcct cttgctgttt gcatccgaat cgtggtctcg ctgttccttg    540
ggagggtctc ctctgagtga ttgactaccc acgacggggg tctttcatt ggggctcgt      600
ccgggatttg agaccctg cccagggacc accgacccac caccgggagg taagctggcc       660
agcaacttat ctgtgtctgt ccgattgtct agtgtctatg tttgatgtta tgcgcctgcg    720
tctgtactag ttagctaact agctctgtat ctggcggacc cgtggtggaa ctgacgagtt    780
ctgaacaccc ggccgcaacc ctgggagacg tcccagggac tttgggggcc gttttttgtgg  840
cccgacctga ggaagggagt cgatgtggaa tccgaccccg tcaggatatg tggttctggt   900
aggagacgag aacctaaaac agttcccgcc tccgtctgaa ttttttgcttt cggtttggaa  960
ccgaagccgc gcgtcttgtc tgctgcagcg ctgcagcatc gttctgtgtt gtctctgtct  1020
gactgtgttt ctgtatttgt ctgaaaatta gggccagact gttaccactc ccttaagttt  1080
gaccttaggt cactggaaag atgtcgagcg gatcgctcac aaccagtcgg tagatgtcaa  1140
gaagagacgt tgggttacct tctgctctgc agaatggcca acctttaacg tcggatggcc   1200
gcgagacggc acctttaacc gagacctcat cacccaggtt aagatcaagg tcttttcacc  1260
tggcccgcat ggacacccag accaggtccc ctacatcgtg acctgggaag ccttggcttt  1320
tgacccccct ccctgggtca agccctttgt acacctaag cctccgcctc ctcttcctcc   1380
atccgccccg tctctccccc ttgaacctcc tcgttcgacc ccgcctcgat cctcccttta    1440
tccagcctc actccttctc taggcgccgg aattccgatc tgatagcttg ccacaacccg   1500
taccaaagat ggatagatcc ggaaagcctg aactcaccgc gacgtctgtc gagaagtttc   1560
tgatcgaaaa gttcgacagc gtctccgacc tgatgcagct ctcggagggc gaagaatctc  1620
gtgctttcag cttcgatgta ggagggcgtg gatatgtcct gcgggtaaat agctgcgccg  1680
atggtttcta caaagatcgt tatgtttatc ggcactttgc atcggccgcg ctcccgattc   1740
cggaagtgct tgacattggg gaattcagcg agagcctgac ctattgcatc tcccgccgtg   1800
cacagggtgt cacgttgcaa gacctgcctg aaaccgaact gcccgctgtt ctgcagccgg   1860
tcgcggaggc catggatgcg atcgctgcgg ccgatcttag ccagacgagc gggttcggcc   1920
```

-continued

```
cattcggacc gcaaggaatc ggtcaataca ctacatggcg tgatttcata tgcgcgattg    1980
ctgatcccca tgtgtatcac tggcaaactg tgatggacga caccgtcagt gcgtccgtcg    2040
cgcaggctct cgatgagctg atgctttggg ccgaggactg ccccgaagtc cggcacctcg    2100
tgcacgcgga tttcggctcc aacaatgtcc tgacggacaa tggccgcata acagcggtca    2160
ttgactggag cgaggcgatg ttcggggatt cccaatacga ggtcgccaac atcttcttct    2220
ggaggccgtg gttggcttgt atggagcagc agacgcgcta cttcgagcgg aggcatccgg    2280
agcttgcagg atcgccgcgg ctccgggcgt atatgctccg cattggtctt gaccaactct    2340
atcagagctt ggttgacggc aatttcgatg atgcagcttg ggcgcagggt cgatgcgacg    2400
caatcgtccg atccggagcc gggactgtcg ggcgtacaca atcgcccgc agaagcgcgg    2460 ccgtctggac cgatggctgt gtagaagtac tcgccgatag tggaaaccga cgccccagca    2520
ctcgtccgag ggcaaaggaa tagagtagat gccgaccgaa caagagctga tttcgagaac    2580
gcctcagcca gcaactcgcg cgagcctagc aaggcaaatg cgagagaacg gccttacgct    2640
tggtggcaca gttctcgtcc acagttcgct aagctcgctc ggctgggtcg cgggagggcc    2700
ggtcgcagtg attcaggccc ttctggattg tgttggtccc cagggcacga ttgtcatgcc    2760
cacgcactcg ggtgatctga ctgatcccgc agattggaga tcgccgcccg tgcctgccga    2820
ttgggtgcag atctatttaa atatcaaata aacctttgtt caaaaaaatt tatctcacct    2880
gtgagtggga gagacaagtc accccagggc ttctggtgac ttcaaattga tagggagaaa    2940
atggttgccc caggggatta aaagcttggt atctgctact cctttagagt tggcctgtct    3000
cctccacttt cccacaattc caccatttcc ccctcccact gggctgggat gcagctgtgg    3060
agtggctcag ctccaaggac tagggctcc acagcccagg tccggcggcc agccctccca    3120
cttccagcct ggaagtggga tggggagtgg gatgagatga accggcagag ttgtagccac    3180
agatgtggat gtgcagggtc cagcacaggg cttgggtgag gagggcggca ccccatccct    3240
tgtctgaaga ccaagcagac agtactcagg acttgggagg gggttgggg aggaggagtg    3300 catgaaactg agaagaacct tctagctgcc tgcgccagga ggtacccggg agctgaagga    3360
gatggagtgc cccagagcag aaagcccctg caggtctgga tgttctaggc tggatgaggg    3420
ggcgaggcag gcctggggac ctgggaagac caggcgcagt acctgccttg cttctgaaaa    3480
tgctgctcca acgtggaaaa acactcccac catctttctt tggagaaagc ctgtaatatt    3540
ccaacaccaa aacctctcac tagaggttcc cgtggagatg ggttccagat gaaaagggaa    3600
ggaggaggca tgggcgctgc ctaacctcca tcctccattc cttaccccctc tcccaccggc    3660 ttctgaagcc ggggtcagaa gaaagggtta aagccttaaa aggggaccga ttttgcgggg    3720
ctctgggggt cggctggcac accctgagcg gccccgccct tctctctagt gtccagaacc    3780
ctccctgccc tgcccaggcc taacggccac aggggtaggg ccccccttta ctgcagaccg    3840
ccactctccc acaccaatat cggaccgcct cctcctccct ctgccacccc ttctcgctcc    3900
ccactcagcc tctgattggc catcgatatg ctgcccggtt tggcactgct cctgctggcc    3960
gcctggacgg ctcgggcgct ggaggtaccc actgatggta atgctggcct gctggctgaa    4020
ccccagattg ccatgttctg tggcagactg aacatgcaca tgaatgtcca gaatgggaag    4080
tgggattcag atccatcagg gaccaaaacc tgcattgata ccaaggaagg catcctgcag    4140
tattgccaag aagtctaccc tgaactgcag atcaccaatg tggtagaagc caaccaacca    4200
gtgaccatcc agaactggtg caagcggggc cgcaagcagt gcaagaccca tccccacttt    4260
gtgattccct accgctgctt agttggtgag tttgtaagtg atgcccttct cgttcctgac    4320
aagtgcaaat tcttacacca ggagaggatg gatgtttgcg aaactcatct tcactggcac    4380
```

-continued

```
accgtcgcca aagagacatg cagtgagaag agtaccaact tgcatgacta cggcatgttg      4440
ctgccctgcg gaattgacaa gttccgaggg gtagagtttg tgtgttgccc actggctgaa      4500
gaaagtgaca atgtggattc tgctgatgcg gaggaggatg actcggatgt ctggtggggc      4560
ggagcagaca cagactatgc agatgggagt gaagacaaag tagtagaagt agcagaggag      4620
gaagaagtgg ctgaggtgga agaagaagaa gccgatgatg acgaggacga tgaggatggt      4680
gatgaggtag aggaagaggc tgaggaaccc tacgaagaag ccacagagag aaccaccagc      4740
attgccacca ccaccaccac caccacagag tctgtggaag aggtggttcg agttcctaca      4800
acagcagcca gtacccctga tgccgttgac aagtatctcg agacacctgg ggatgagaat      4860
gaacatgccc atttccagaa agccaaagag aggcttgagg ccaagcaccg agagagaatg      4920
tcccaggtca tgagagaatg ggaagaggca gaacgtcaag caaagaactt gcctaaagct      4980
gataagaagg cagttatcca gcatttccag agaaagtgg  aatctttgga acaggaagca      5040
gccaacgaga gacagcagct ggtggagaca cacatggcca gagtggaagc catgctcaat      5100
gaccgccgcc gcctggccct ggagaactac atcaccgctc tgcaggctgt tcctcctcgg      5160
cctcgtcacg tgttcaatat gctaaagaag tatgtccgcg cagaacagaa ggacagacag      5220
cacaccctaa agcatttcga gcatgtgcgc atggtggatc ccaagaaagc cgctcagatc      5280
cggtcccagg ttatgacaca cctccgtgtg atttatgagc gcatgaatca gtctctctcc      5340
ctgctctaca acgtgcctgc agtggccgag agattcagg  atgaagttga tgagctgctt      5400
cagaaagagc aaaactattc agatgacgtc ttggccaaca tgattagtga accaaggatc      5460
agttacggaa acgatgctct catgccatct ttgaccgaaa cgaaaccacc cgtggagctc      5520
cttcccgtga atggagagtt cagcctggac gatctccagc cgtggcattc tttgggget       5580
gactctgtgc cagccaacac agaaaacgaa gttgagcctg ttgatgcccg ccctgctgcc      5640
gaccgaggac tgaccactcg accaggttct gggttgacaa atatcaagac ggaggagatc      5700
tctgaagtga atctggatgc agaattccga catgactcag gatatgaagt tcatcatcaa      5760
aaattggtgt tctttgcaga agatgtgggt tcaaacaaag gtgcaatcat tggactcatg      5820
gtgggcggtg ttgtcatagc gacagtggtc atcatcacct tggtgatgct gaagaagaaa      5880
cagtacacat ccattcatca tggtgtggtg gaggttgacg ccgctgtcac cccagaggag      5940
cgccacctgt ccaatctgca gcagaacggc tacgaaaatc caacctacaa gttctttgag      6000
cagatgcaga acttaattaa ggcatgcgga agcggagcta ctaacttcag cctgctgaag      6060
caggctggag acgtggagga gaaccctgga cctagatcta tggctgagcc ccgccaggag      6120
ttcgaagtga tggaagatca cgctgggacg tacgggttgg gggacaggaa agatcagggg      6180
ggctacacca tgcaccaaga ccaagagggt gacacgacg  ctggcctgaa agctgaagaa      6240
gcaggcattg agacacccc  cagcctggaa gacgaagctg ctggtcacgt gacccaagct      6300
cgcatggtca gtaaaagcaa agacgggact ggaagcgatg acaaaaaagc caaggggggct     6360
gatggtaaaa cgaagatcgc cacaccgcgg ggagcagccc ctccaggcca gaagggccag      6420
gccaacgcca ccaggattcc agcaaaaacc ccgcccgctc caaagacacc acccagctct      6480
ggtgaacctc caaaatcagg ggatcgcagc ggctacagca gccccggctc cccaggcact      6540
cccggcagcc gctcccgcac ccgtcccctt ccaaccccac ccaccccgga gcccaagaag      6600
gtggcagtgg tccgtactcc acccaagtcg ccgtcttccg ccaagagccg cctgcagaca      6660
gcccccgtgc ccatgccaga cctgaagaat gtcaagtcca gatcggctc  cactgagaac      6720
ctgaagcacc agccgggagg cgggaaggtg cagataatta ataagaagct ggatcttagc      6780
```

-continued

```
aacgtccagt ccaagtgtgg ctcaaaggat aatatcaaac acgtcctggg aggcggcagt    6840
gtgcaaatag tctacaaacc agttgacctg agcaaggtga cctccaagtg tggctcatta    6900
ggcaacatcc atcataaacc aggaggtggc caggtggaag taaaatctga gaagcttgac    6960
ttcaaggaca gagtccagtc gaagattggg tccctggaca atatcaccca cgtccctggc    7020
ggaggaaata aaagattga aacccacaag ctgaccttcc gcgagaacgc caaagccaag    7080
acagaccacg gggcggagat cgtgtacaag tcgccagtgg tgtctgggga cacgtctcca    7140
cggcatctca gcaatgtctc ctccaccggc agcatcgaca tggtagactc gccccagctc    7200
gccacgctag ctgacgaggt gtctgcctcc ctggccaagc aggtttgga attcggaagc    7260 ggagctacta acttcagcct gctgaagcag gctggagacg tggaggagaa ccctggacct    7320
ctcgagatga cagagttacc tgcaccgttg tcctacttcc agaatgcaca gatgtctgag    7380
gacaaccacc tgagcaatac tgtacgtagc cagaatgaca atagagaacg gcaggagcac    7440
aacgacagac ggagccttgg ccaccctgag ccattatcta atggacgacc ccagggtaac    7500
tcccggcagg tggtggagca agatgaggaa gaagatgagg agctgacatt gaaatatggc    7560
gccaagcatg tgatcatgct ctttgtccct gtgactctct gcatggtggt ggtcgtggct    7620
accattaagt cagtcagctt ttatacccgg aaggatgggc agctaatcta taccccattc    7680
acagaagata ccgagactgt gggccagaga gccctgcact caattctgaa tgctgccatc    7740
atgatcagtg tcattgttgt cctgactatc tccctggtgg ttctgtataa atacaggtgc    7800
tataaggtca tccatgcctg gcttattata tcatctctat tgttgctgtt cttttttca    7860 ttcatttact tggggaagt gtttaaaacc tataacgttg ctgtggacta cattactgtt    7920
gcactcctga tctggaattt tggtgtggtg ggaatgattt ccattcactg gaaaggtcca    7980
cttcgactcc agcaggcata tctcattatg attagtgccc tcatgccct ggtgtttatc    8040 aagtacctcc ctgaatggac tgcgtggctc atcttggctg tgatttcagt atatgattta    8100
gtggctgttt tgtgtccgaa aggtccactt cgtatgctgg ttgaaacagc tcaggagaga    8160
aatgaaacgc ttttccagc tgtcatttac tcctcaacaa tggtgtggtt ggtgaatatg    8220
gcagaaggag acccggaagc tcaaaggaga gtatccaaaa attccaagta taatgcagaa    8280
agcacagaaa gggagtcaca agacactgtt gcagagaatg atgatggcgg gttcagtgag    8340
gaatgggaag cccagaggga cagtcatcta gggcctcatc gctctacacc tgagtcacga    8400
gctgctgtcc aggaactttc cagcagtatc ctcgctggtg aagacccaga ggaaagggga    8460
gtaaaacttg gattgggaga tttcattttc tacagtgttc tggttggtaa agcctcagca    8520
acagccagtg gagactggaa cacaaccata gcctgtttcg tagccatatt aattggtttg    8580
tgccttacat tattactcct tgccattttc aagaaagcat tgccagctct tccaatctcc    8640
atcacctttg ggcttgtttt ctactttgcc acagattatc ttgtacagcc ttttatggac    8700
caattagcat tccatcaatt ttatatctag cctgcaggtc tagatagcta gcctccctat    8760
agtgagtcgt attacgtaga tccagacatg ataagataca ttgatgagtt tggacaaacc    8820
acaactagaa tgcagtgaaa aaatgcttt atttgtgaaa tttgtgatgc tattgcttta    8880
tttgtaacca ttataagctg caataaacaa gttaacaaca acaattgcat tcattttatg    8940
tttcaggttc aggggaggt gtgggaggtt ttttaattcg cggccgcctc gagagatccc    9000
ctcaggatat agtagtttcg cttttgcata gggaggggga aatgtagtct tatgcaatac    9060
tcttgtagtc ttgcaacatg gtaacgatga gttagcaaca tgccttacaa ggagagaaaa    9120
agcaccgtgc atgccgattg gtggaagtaa ggtggtacga tcgtgcctta ttaggaaggc    9180
aacagacggg tctgacatgg attggacgaa ccactgaatC ccgcattgca gagatattgt    9240
```

```
atttaagtgc ctagctcgat acagcaaacg ccatttgacc attcaccaca ttggtgtgca   9300
cctccaagct tgttaattca ccatgtctag actggacaag agcaaagtca taaacggcgc   9360
tctggaatta ctcaatggag tcggtatcga aggcctgacg acaaggaaac tcgctcaaaa   9420
gctgggagtt gagcagccta ccctgtactg gcacgtgaag aacaagcggg ccctgctcga   9480
tgccctgcca atcgagatgc tggacaggca tcatacccac ttctgccccc tggaaggcga   9540
gtcatggcaa gactttctgc ggaacaacgc caagtcattc cgctgtgctc tcctctcaca   9600
tcgcgacggg gctaaagtgc atctcggcac ccgcccaaca gagaaacagt acgaaaccct   9660
ggaaaatcag ctcgcgttcc tgtgtcagca aggcttctcc ctggagaacg cactgtacgc   9720
tctgtccgcc gtgggccact ttacactggg ctgcgtattg gaggaacagg agcatcaagt   9780
agcaaaagag gaaagagaga cacctaccac cgattctatg cccccacttc tgagacaagc   9840
aattgagctg ttcgaccggc agggagccga acctgccttc cttttcggcc tggaactaat   9900
catatgtggc ctgagagaaac agctaaagtg cgaaagcggc gggccggccg acgcccttga   9960
cgattttgac ttagacatgc tcccagccga tgcccttgac gactttgacc ttgatatgct  10020
gcctgctgac gctcttgacg attttgacct tgacatgctc cccgggtaac taagtaagga  10080
tcaacatcga attcgatttc tgttcctgtt aatcaacctc tggattacaa aatttgtgaa  10140
agattgactg gtattcttaa ctatgttgct ccttttacgc tatgtggata cgctgcttta  10200
atgcctttgt atcatgctat tgcttcccgt atggctttca ttttctcctc cttgtataaa  10260
tcctggttgc tgtctcttta tgaggagttg tggcccgttg tcaggcaacg tggcgtggtg  10320
tgcactgtgt ttgctgacgc aacccccact ggttggggca ttgccaccac ctgtcagctc  10380
cttccgggga ctttcgcttt ccccctccct attgccacgg cggaactcat cgccgcctgc  10440
cttgcccgct gctggacagg ggctcggctg ttgggcactg acaattccgt ggtgttgtcg  10500
gggaagctga cgtcctttcc atggctgctc gcctgtgttg ccacctggat tctgcgcggg  10560
acgtccttct gctacgtccc ttcggccctc aatccagcgg accttccttc ccgcggcctg  10620
ctgccggctc tgcggcctct tccgcgtctt cgccttcgcc ctcagacgag tcggatctcc  10680
ctttgggccg cctccccgcc tgtttcgcct cgggctcaat cactagtgaa ttcgataaaa  10740
taaaagattt tatttagtct ccagaaaaag gggggaatga agacccac ctgtaggttt  10800
ggcaagctag cttaagtaac gccattttgc aaggcatgga aaaatacata actgagaata  10860
gagaagttca gatcaaggtc aggaacagat ggaacagctg aatatgggcc aaacaggata  10920
tctgtggtaa gcagttcctg ccccggctca gggccaagaa cagatggaac agctgaatat 10980
gggccaaaca ggatatctgt ggtaagcagt tcctgccccg gctcagggcc aagaacagat  11040
ggtccccaga tgcggtccag ccctcagcag tttctagaga accatcagat gtttccaggg  11100
tgccccaagg acctgaaatg accctgtgcc ttatttgaac taaccaatca gttcgcttct  11160
cgcttctgtt cgcgcgcttc tgctccccga gctcaataaa agagcccaca cccctcact  11220
cggggcgcca gtcctccgat tgactgagtc gcccgggtac ccgtgtatcc aataaaccct  11280
cttgcagttg catccgactt gtggtctcgc tgttccttgg gagggtctcc tctgagtgat  11340
tgactacccg tcagcggggg tctttcattt gggggctcgt ccgggatcgg gagacccctg  11400
cccagggacc accgacccac caccgggagg taagctggct gcctcgcgcg tttcggtgat  11460
gacggtgaaa acctctgaca catgcagctc ccggagacgg tcacagcttg tctgtaagcg  11520
gatgccggga gcagacaagc ccgtcagggc gcgtcagcgg gtgttggcgg gtgtcggggc  11580
gcagccatga cccagtcacg tagcgatagc ggagtgtata ctggcttaac tatgcggcat  11640
```

```
cagagcagat tgtactgaga gtgcaccata tgcggtgtga ataccgcac agatgcgtaa    11700 ggagaaaata ccgcatcagg cgctcttccg cttcctcgct cactgactcg ctgcgctcgg   11760
tcgttcggct gcggcgagcg gtatcagctc actcaaaggc ggtaatacgg ttatccacag   11820
aatcagggga taacgcagga agaacatgt gagcaaaagg ccagcaaaag gccaggaacc    11880
gtaaaaaggc cgcgttgctg gcgttttttcc ataggctccg ccccctgac gagcatcaca   11940 aaaatcgacg ctcaagtcag aggtggcgaa acccgacagg actataaaga taccaggcgt   12000
ttccccctgg aagctccctc gtgcgctctc ctgttccgac cctgccgctt accggatacc   12060
tgtccgcctt tctcccttcg ggaagcgtgg cgctttctca tagctcacgc tgtaggtatc   12120
tcagttcggt gtaggtcgtt cgctccaagc tgggctgtgt gcacgaaccc cccgttcagc   12180
ccgaccgctg cgccttatcc ggtaactatc gtcttgagtc caacccggta agacacgact   12240
tatcgccact ggcagcagcc actggtaaca ggattagcag agcgaggtat gtaggcggtg   12300
ctacagagtt cttgaagtgg tggcctaact acggctacac tagaaggaca gtatttggta   12360
tctgcgctct gctgaagcca gttaccttcg gaaaaagagt tggtagctct tgatccggca   12420
aacaaaccac cgctggtagc ggtggttttt tgtttgcaa gcagcagatt acgcgcagaa    12480 aaaaggatc tcaagaagat cctttgatct tttctacggg gtctgacgct cagtggaacg   12540
aaaactcacg ttaagggatt ttggtcatga gattatcaaa aaggatcttc acctagatcc   12600 tttttaaatta aaaatgaagt tttaaatcaa tctaaagtat atatgagtaa acttggtctg   12660
acagttacca atgcttaatc agtgaggcac ctatctcagc gatctgtcta tttcgttcat   12720
ccatagttgc ctgactcccc gtcgtgtaga taactacgat acgggagggc ttaccatctg   12780
gccccagtgc tgcaatgata ccgcgagacc cacgctcacc ggctccagat ttatcagcaa   12840
taaaccagcc agccggaagg gccgagcgca gaagtggtcc tgcaacttta tccgcctcca   12900
tccagtctat taattgttgc cgggaagcta gagtaagtag ttcgccagtt aatagtttgc   12960
gcaacgttgt tgccattgct gcaggcatcg tggtgtcacg ctcgtcgttt ggtatggctt   13020
cattcagctc cggttcccaa cgatcaaggc gagttacatg atcccccatg ttgtgcaaaa   13080
aagcggttag ctccttcggt cctccgatcg ttgtcagaag taagttggcc gcagtgttat   13140
cactcatggt tatggcagca ctgcataatt ctcttactgt catgccatcc gtaagatgct   13200
tttctgtgac tggtgagtac tcaaccaagt cattctgaga atagtgtatg cggcgaccga   13260
gttgctcttg cccggcgtca cacgggata ataccgcgcc acatagcaga actttaaaag    13320
tgctcatcat tggaaaacgt tcttcggggc gaaaactctc aaggatctta ccgctgttga   13380
gatccagttc gatgtaaccc actcgtgcac ccaactgatc ttcagcatct tttactttca   13440
ccagcgtttc tgggtgagca aaaacaggaa ggcaaaatgc cgcaaaaaag gaataagggg   13500
cgacacggaa atgttgaata ctcatactct tcctttttca atattattga agcatttatc   13560
agggttattg tctcatgagc ggatacatat ttgaatgtat ttagaaaaat aaacaaatag   13620
gggttccgcg cacatttccc cgaaaagtgc cacctgacgt ctaagaaacc attattatca   13680
tgacattaac ctataaaaat aggcgtatca cgaggccctt tcgtcttcaa gaattcatac   13740
cagatcaccg aaaactgtcc tccaaatgtg tccccctcac actcccaaat tcgcgggctt   13800
ctgcctctta gaccactcta ccctattccc cacactcacc ggagccaaag ccgcggccct   13860
tccgtttctt tgct
```

What is claimed is:

1. A method of preparing a transgenic pig comprising:
providing a somatic cell from a pig;
introducing an expression vector into said somatic cell to produce a genetically modified somatic cell;
introducing said genetically modified somatic cell into an enucleated pig oocyte to produce a transgenic pig embryo;
transplanting said transgenic pig embryo into a surrogate pig to produce a transgenic pig,
wherein said expression vector is a recombinant expression vector, comprising:
a Thy1 gene promoter having a base sequence of SEQ ID NO: 1 or SEQ ID NO: 4; and
a mutant gene selected from the group consisting of: a mutant APP gene, a mutant Tau gene and a mutant PS1 gene, wherein said mutant gene is a mutant gene found in patients with familial Alzheimer's disease.

2. The method of claim 1, wherein the Thy1 gene promoter includes binding sites for PBX and CREB transcription factors.

* * * * *